(12) United States Patent
Jager Lezer et al.

(10) Patent No.: US 8,980,240 B2
(45) Date of Patent: Mar. 17, 2015

(54) EYELASH MAKEUP AND/OR CARE ASSEMBLY

(75) Inventors: Nathalie Jager Lezer, Verrieres-le-Buisson (FR); Stephane Arditty, Ballainvilliers (FR)

(73) Assignee: L'Oreal, Paris (FR)

( * ) Notice: Subject to any disclaimer, the term of this patent is extended or adjusted under 35 U.S.C. 154(b) by 653 days.

(21) Appl. No.: 12/480,859

(22) Filed: Jun. 9, 2009

(65) Prior Publication Data

US 2010/0031969 A1    Feb. 11, 2010

Related U.S. Application Data

(60) Provisional application No. 61/086,171, filed on Aug. 5, 2008.

(30) Foreign Application Priority Data

Jun. 10, 2008 (FR) ..................... 08 53853

(51) Int. Cl.
*A46B 11/00* (2006.01)
*A45D 40/26* (2006.01)
*A61K 8/04* (2006.01)
(Continued)

(52) U.S. Cl.
CPC ............. *A45D 40/262* (2013.01); *A61K 8/044* (2013.01); *A61Q 1/10* (2013.01); *A61K 8/0254* (2013.01); *A45D 2200/157* (2013.01); *A45D 2200/207* (2013.01); *A61K 2800/87* (2013.01)
USPC ............ 424/70.7; 401/1; 132/200; 424/70.11

(58) Field of Classification Search
CPC ........ A61Q 1/10; A61K 8/0254; A61K 8/044
USPC .......... 401/129; 424/70.7, 70.1, 70.31, 70.22, 424/70.11, 70.12, 70.17
See application file for complete search history.

(56) References Cited

U.S. PATENT DOCUMENTS 7,794,695 B2 * 9/2010 Lion et al. ................ 424/64
7,887,788 B2 * 2/2011 De La Poterie et al. ..... 424/70.7
(Continued)

FOREIGN PATENT DOCUMENTS

| EP | 1 785 128 | 5/2007 |
|----|-----------|--------|
| EP | 1 920 676 | 5/2008 |

(Continued)

OTHER PUBLICATIONS

Office Action issued Sep. 10, 2013 in Japanese Application No. 2009-138381 (English Translation).
(Continued)

*Primary Examiner* — David Walczak
*Assistant Examiner* — Jennifer C Chiang
(74) *Attorney, Agent, or Firm* — Oblon, McClelland, Maier & Neustadt, L.L.P.

(57) ABSTRACT

Assembly and method for making up and/or caring for keratin material, the assembly containing:
  at least one composition containing platelet-shaped particles, at least one nonionic surfactant and/or at least one ionic surfactant and/or at least one polymeric surfactant, or at least one fatty-phase rheological agent, and
  at least one applicator having an application member and a vibrating source for making the application member vibrate.

18 Claims, 1 Drawing Sheet

(51) Int. Cl.
*A61Q 1/10* (2006.01)
*A61K 8/02* (2006.01)

(56) References Cited

U.S. PATENT DOCUMENTS

| | | | |
|---|---|---|---|
| 8,317,423 B2* | 11/2012 | Marotta et al. | 401/126 |
| 2005/0142082 A1* | 6/2005 | Ferrari | 424/63 |
| 2005/0191258 A1* | 9/2005 | De La Poterie et al. | 424/70.1 |
| 2006/0032512 A1 | 2/2006 | Kress et al. | |
| 2006/0216257 A1 | 9/2006 | Pays et al. | |
| 2006/0233732 A1* | 10/2006 | Lezer | 424/70.7 |
| 2007/0246058 A1 | 10/2007 | Bodelin | |
| 2007/0292381 A1* | 12/2007 | Jacquier | 424/70.15 |
| 2008/0171009 A1* | 7/2008 | Auguste et al. | 424/70.7 |
| 2009/0053270 A1 | 2/2009 | Yoshida et al. | |
| 2010/0086507 A1* | 4/2010 | Gueret | 424/70.7 |

FOREIGN PATENT DOCUMENTS

| | | |
|---|---|---|
| JP | 2006-176513 A | 7/2006 |
| JP | 2006-265252 A | 10/2006 |
| JP | 2006-312623 A | 11/2006 |
| JP | 2007-296331 A | 11/2007 |
| JP | 2008-504945 A | 2/2008 |
| WO | WO 2006/020577 A2 | 2/2006 |

OTHER PUBLICATIONS

Appeal Decision as received in the corresponding Japanese Patent Application 2009-138381 dated Nov. 10, 2014.

* cited by examiner

EYELASH MAKEUP AND/OR CARE ASSEMBLY

This application claims priority to U.S. provisional application 61/086,171, filed Aug. 5, 2008; and to French patent application 08 53853, filed Jun. 10, 2008, both incorporated herein by reference.

FIELD OF THE INVENTION

The present invention relates to an assembly for making up and/or caring for keratin materials, especially keratin fibres, especially the eyelashes, comprising:
  at least one composition useful for making up and/or caring for the eyelashes, comprising platelet-shaped particles, at least one nonionic surfactant and/or at least one ionic surfactant and/or at least one polymeric surfactant, or at least one oil structured with at least one fatty-phase rheological agent,
  at least one applicator comprising an application member, and means for, the ability to, etc., before, simultaneously with or after its application to the fibres, making the composition vibrate.

The disclosed cosmetic composition also makes up a part of the invention.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

There is a need to obtain good makeup effects on the eyelashes and especially to have available a mascara that gives a good quality of deposit, good separation and/or a thickening effect, in order to achieve a more or less natural result according to the consumer's wishes.

There is in particular a need to provide formulations of which it is possible, prior to and/or simultaneously with application, to modify the rheology, in particular by reducing the viscosity thereof, in order to make it possible to obtain a smoother deposit and a better definition of the makeup.

It may prove difficult to obtain this result using an applicator of standard brush or comb type.

The patent application published under No. US2006/0032512 describes a vibrating system for applying mascara to the eyelashes, one of the claimed effects of which lies in the ability of the system to modify the rheology of the mascara applied. This patent application makes absolutely no mention of the features of the composition which are capable, in combination with a vibrating applicator, of resulting in such a modification of rheology. With experiments, it is found that not all mascara compositions have a vibration-sensitive rheology. In addition, in this patent application, the viscosity modifications to which reference is made, and which are generally less than 10%, cannot, given the method of measurement, be really considered to be significant.

DETAILED DESCRIPTION OF THE PREFERRED EMBODIMENTS

Figure 2:
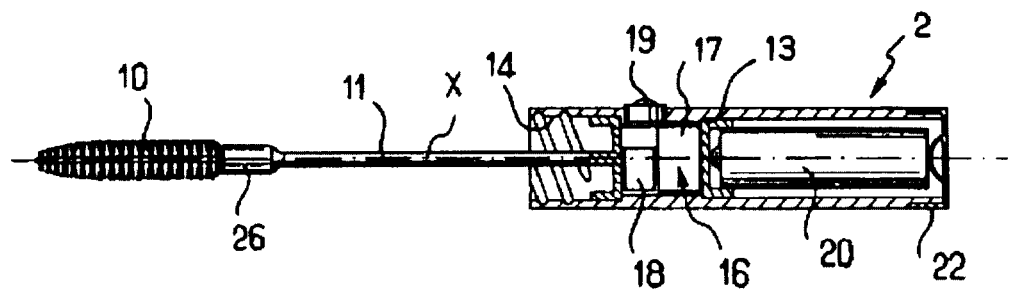
FIG. 2 shows in isolation the applicator of FIG. 1, with partial and schematic longitudinal cross section.

The inventors have now found that a more substantial makeup result, from the point of view of the definition or loading of the eyelashes, is obtained by use of the assembly according to the invention.

The invention is thus directed towards readily achieving this makeup objective.

According to one of its aspects, one subject of the present invention is thus an assembly for making up and/or caring for keratin materials, in particular keratin fibres, especially the eyelashes or the eyebrows, comprising:
  a container delimiting, defining, etc., at least one compartment containing at least one composition for making up and/or caring for a keratin material, in particular the eyelashes or the eyebrows, comprising platelet-shaped particles,
  at least one applicator comprising an application member for applying the composition to the materials, and
  a vibrator for, before, simultaneously with or after its application to the keratin materials, making the makeup composition vibrate.

A subject of the present invention is also an assembly for making up and/or caring for keratin materials, in particular keratin fibres, especially the eyelashes or the eyebrows, comprising:
  a container delimiting, defining, etc., at least one compartment containing at least one composition for making up and/or caring for the materials, in particular the eyelashes or the eyebrows, comprising at least one nonionic surfactant and/or at least one ionic surfactant and/or at least one polymeric surfactant,
  at least one applicator comprising an application member for applying the composition to the materials, and
  a vibrator for, before, simultaneously with or after its application to the keratin materials, making the makeup composition vibrate.

A subject of the present invention is also an assembly for making up and/or caring for keratin materials, in particular keratin fibres, especially the eyelashes or the eyebrows, comprising:
  a container delimiting, defining, etc., at least one compartment containing at least one composition for making up and/or caring for the materials, in particular the eyelashes or the eyebrows, comprising at least one oil structured with at least one fatty-phase rheological agent and less than 10% by weight and preferably less than 5% by weight of wax relative to the total weight of the composition,
  at least one applicator comprising an application member for applying the composition to the materials, and
  a vibrator for, before, simultaneously with or after its application to the keratin materials, making the makeup composition vibrate. Preferably, according to this alternative, the composition is free of wax.

A subject of the present invention is also an assembly for making up and/or caring for keratin materials, in particular keratin fibres, especially the eyelashes or the eyebrows, comprising:

- a container delimiting, defining, etc., at least one compartment containing at least one composition for making up and/or caring for the materials, in particular the eyelashes or the eyebrows, comprising at least one oil structured with at least one fatty-phase rheological agent, the fatty-phase rheological agent being chosen from the chemical families listed hereinbelow,
- at least one applicator comprising an application member for applying the composition to the materials, and
- a vibrator for, before, simultaneously with or after its application to the keratin materials, making the makeup composition vibrate. According to this alternative, preferably, the composition used contains less than 10% by weight and preferably less than 5% by weight of wax relative to the total weight of the composition, and is preferably free of wax.

These vibrators are preferably formed by a vibrating source which, before, simultaneously with or after the application of the composition to the fibres, makes this composition vibrate.

Advantageously, the composition is a composition to be applied to the eyelashes, especially a mascara, the composition being subjected to the vibrations during and/or after its application so as to give good definition and/or a good loading effect to the eyelashes.

According to one advantageous embodiment, the composition is made to vibrate by virtue of the application member itself, this member being coupled to a vibrating source. Thus, advantageously, the vibrating source is coupled to the application member so as to make the member vibrate before applying the composition to the fibres, during the application of the composition to the fibres, or thereafter.

Alternatively, the application of the composition to, e.g., the eyelashes and its vibration are performed by two different tools, one for applying the composition to the eyelashes or the eyebrows, and the other for vibrating the deposit thus made.

The composition is preferably a product intended to be applied to the eyelashes, for example a mascara.

The inventors have observed that, under the effect of vibration, the viscosity of the composition varies. Specifically, the composition is found to be either thicker or more fluid. In the first case, i.e. when the composition is thickened (increased viscosity), it affords good thickening of the eyelashes and thus a good loading effect. In the second case, i.e. when the composition is thinned (reduced viscosity), it affords a smoother deposit, and better definition of the makeup, and thus a better quality of deposit and better separation of the eyelashes.

Application of the composition to the eyelashes or the eyebrows, coupled with making the composition vibrate, either simultaneously with its deposition or thereafter, thus makes it possible to vary its viscosity.

In particular, the assembly according to the invention affords a smooth, uniform deposit that is easy to apply, which separates and coats the eyelashes, and/or which gives a good loading effect.

According to a second aspect, the present invention relates to a non-therapeutic process for making up and/or caring for keratin materials, in particular keratin fibres, in particular the eyelashes or the eyebrows, which consists in vibrating, simultaneously with or after its application to the keratin materials, a composition comprising:

- platelet-shaped particles, and/or
- at least one nonionic surfactant and/or at least one ionic surfactant and/or at least one polymeric surfactant, and/or
- at least one oil structured with at least one fatty-phase rheological agent.

The process according to the invention may thus comprise:
- applying to the keratin materials at least one coat of a make up and/or care composition,
- making the composition vibrate before and/or simultaneously with and/or after its application to the materials,
- the process being characterized in that the composition comprises platelet-shaped particles, and/or at least one nonionic surfactant and/or at least one ionic surfactant and/or at least one polymeric surfactant, and/or at least one oil structured with at least one fatty-phase rheological agent.

Preferably, the composition is an eyelash makeup composition, and it is subjected to the vibrations during and/or after its application to the eyelashes so as to give these eyelashes good definition and/or a good loading effect before the composition has become completely dry.

The composition thus applied and made to move by a vibrating member affords a smooth, uniform deposit that is easy to apply, which separates and coats the eyelashes, and/or which gives a good loading effect.

The compositions in accordance with the invention comprise a physiologically acceptable medium, especially a cosmetically acceptable medium, i.e. a medium that is compatible in particular with the eyelashes and the region of the eyes.

In the context of the present invention, the term "cosmetically acceptable" means a composition whose use is compatible with application to the eyelashes.

The expression "comprising one" should be considered as being synonymous with the expression "comprising at least one", and the term "between" should be considered as including the limits, unless otherwise specified.

All the contents of components are expressed as solids.

The terms "application means" and "applicator" are used without discrimination in the rest of the description. In this regard, the term "means" as used in this specification is used to generically denote a method, a course of action, or an instrument, device, etc., by which an act can be accomplished or an end achieved, and is not limited to the specific embodiments thereof shown or demonstrated herein. To the contrary, where used in the claims the term "means," when part of a phrase invoking 35 U.S.C. 112, $6^{th}$ paragraph, will have a meaning as assigned under 35 U.S.C. 112, $6^{th}$ paragraph.

According to a first preferred alternative, the composition according to the invention comprises platelet-shaped particles.

The term "platelet-shaped particle" means a particle for which one of the dimensions is very much smaller than the other two. Such platelets usually have a thickness E that is much smaller than their length L1 or their width L2.

Preferably, the ratio E/L1 and E/L2 is less than or equal to 0.5, preferably less than or equal to 0.3 and preferably less than or equal to 0.1.

These platelet-shaped particles are chosen especially from certain gelling agents and certain fillers, the fillers possibly being uncoloured or coloured (e.g. reflective particles).

They may be present in the composition in an amount ranging from 0.5% to 60% by weight, preferably in an amount ranging from 1% to 50% by weight and preferably in an amount ranging from 1.5% to 25% by weight relative to the total weight of the composition.

In particular, an amount ranging from 1% to 7% by weight and preferably 3% to 4% by weight, relative to the total weight of the composition, will be used for platelet-shaped particles with an average length L1 of less than 500 nm. This is the case especially for clays such as the hectorites, bentonites, magnesium silicates and montmorillonites described hereinbelow.

In the case of platelet-shaped particles with an average length L1 of greater than 500 nm, an amount of the particles ranging from 15% to 35% by weight and preferably from 20% to 25% by weight, relative to the total weight of the composition, will advantageously be used. This is the case especially for the fillers and reflective particles described hereinbelow, and in particular for talc, mica, kaolin, lauroyl lysine, and reflective particles comprising a synthetic mica substrate coated with titanium oxide and/or iron oxides.

Among the gelling agents that may be used, mention may be made of lipophilic or hydrophilic clays.

The term "hydrophilic clay" means a clay that is capable of swelling in water; this clay swells in water and forms after hydration a colloidal dispersion.

These clays are products that are already well known per se, which are described, for example, in the book "Minéralogie des argiles", S. Caillère, S. Hénin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites.

These clays may be of natural or synthetic origin.

Hydrophilic clays that may be mentioned include smectite products such as saponites, hectorites, montmorillonites, bentonites and beidellite.

Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion.

Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

Among the fillers that may be used, mention may be made of those that are well known to persons skilled in the art and that are commonly used in cosmetic compositions.

The fillers may be mineral or organic, and lamellar or platelet-shaped.

Mention may be made of talc, mica, barium sulfate, kaolin, lauroyllysine, starch, boron nitride, precipitated calcium carbonate, magnesium carbonate, magnesium hydrogen carbonate, hydroxyapatite, montmorillonite (for example Gel White H from Rookwood Additives), polytetrafluoroethylene (PTFE) wax particles (for instance Ceridust 9205 F from Clariant, or Fluoropure 103 C from Shamrock Technologies), calcium sulfate (for instance Prestia PR306 from Lafarge Prestia), pumice powder (for instance O-D decontaminated pumice from Eyraud), bismuth oxychloride, bismuth oxychloride and zinc oxide powder (for instance Pearl II UCR from Farmaquimia), perlite (for instance Optima 1430 OR from World Minerals), glass particles especially about 10 microns in size and about 0.4 micron thick, for instance those sold under the references MTD010FYX(6001) or MTD010FYX(6009) by Nippon Sheet Glass, about 25 microns in size and about 0.4 micron thick, for instance those sold under the references MTD025FYX(6002) or MTD025FYX(6010) by Nippon Sheet Glass, silica and titanium dioxide sol/gel particles (for instance NLT30H2WA from Nippon Sheet Glass), mica and titanium dioxide particles, for instance Blancsealer from Merck, and metal soaps derived from organic carboxylic acids containing from 8 to 22 carbon atoms and in particular from 12 to 18 carbon atoms, for example zinc, magnesium or lithium stearate, zinc laurate or magnesium myristate, or alternatively multilayer platelet-shaped reflective particles, in particular reflective particles comprising a synthetic mica substrate coated with titanium dioxide and/or black iron oxide, and mixtures thereof.

The barium sulfate particles mentioned above may be coated with an N-acylamino acid such as those comprising an acyl group containing from 8 to 22 carbon atoms, for instance a 2-ethylhexanoyl, caproyl, lauroyl, myristoyl, palmitoyl, stearoyl or cocoyl group. The amino acid may be, for example, lysine, glutamic acid or alanine. Preferably, the barium sulfate particles are coated with lauroyllysine.

The multilayer platelet-shaped reflective particles enable the reflection to be made more directional.

The reflective particles have, for example, a metallic tint and advantageously comprise at least one electrically conductive surface coat, formed from at least one metal or metal oxide.

Irrespective of their shape, the reflective particles with a metallic tint comprise, for example, at least one coat that preferably has a uniform thickness, especially of a reflective material, advantageously a metallic compound.

The reflective particles according to the invention may comprise, for example, a natural or synthetic substrate, especially a synthetic substrate at least partially coated with at least one layer of a reflective material, especially of at least one metal or metallic material. The substrate may be a mono-material, multimaterial, organic and/or mineral substrate. More particularly, the substrate may be chosen from glasses, ceramics, graphite, metal oxides, aluminas, silicas, silicates, especially aluminosilicates and borosilicates, and synthetic mica, and mixtures thereof, this list not being limiting.

Reflective particles according to the invention that may be mentioned include white nacreous pigments such as mica coated with titanium or with bismuth oxychloride, coloured nacreous pigments such as titanium mica with iron oxides, titanium mica especially with ferric blue or with chromium oxide, and nacreous pigments based on bismuth oxychloride.

As examples of reflective particles comprising a mineral substrate coated with a layer of metal, mention may be made of particles comprising a silver-coated borosilicate substrate. Particles containing a platelet-shaped silver-coated glass substrate are sold under the name Microglass Metashine REFSX 2025 PS by the company Toyal. Particles containing a glass substrate coated with nickel/chromium/molybdenum alloy are sold under the name Crystal Star GF 550 or GF 2525 by this same company. Particles containing a glass substrate coated with titanium oxide are sold under the name Metashine MC1120RY by the company Nippon Sheet Glass or Reflecks Dimensions Glittering Gold G230S by the company Engelhard. Particles containing a glass substrate coated with silver oxide having silvery tints are sold under the name Metashine MC1020RS by the company Nippon Sheet Glass or Reflecks Dimensions Luminous White G130M by the company Engelhard.

Whether they are lamellar or platelet-shaped, the reflective particles with a metallic tint may also be chosen from particles containing a synthetic substrate at least partially coated with at least one coat of at least one metal oxide, chosen, for example, from titanium oxides, especially $TiO_2$, iron oxides, especially $Fe_2O_3$, tin oxide, chromium oxide, barium sulfate and the following materials: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$ and mixtures thereof.

Examples of such particles that may be mentioned include particles comprising a synthetic mica substrate coated with titanium dioxide, or glass particles coated either with brown iron oxide, with titanium oxide, with tin oxide or with a mixture thereof, for instance the products sold under the brand name Reflecks® by the company Engelhard. Mention may also be made of mica particles covered with titanium dioxide and iron oxide, for instance Flamenco Satin Gold 260 M from Engelhard, and silica particles covered with titanium oxide, for instance Xirona Kiwi Rose from Merck.

As other examples of particles comprising a synthetic mica substrate coated with titanium dioxide and/or black iron oxide, mention may be made especially of the mica-titanium oxide-black iron oxide particles (58% CI77019+18% CI77891+24% CI77499) sold under the name Colorona Patina Silver by the company Merck; the mica-titanium oxide particles (52.5% CI77019+47.5% CI77891) sold under the name Flamenco Blue 620C by the company BASF Personal Care Ingredients; the mica-iron oxide particles (52% CI77019+48% CI77499) sold under the name Colorina Blackstar Red by the company Merck; the mica-titanium oxide-tin oxide-iron oxide particles (48% CI77019+36% CI77891+1% CI77861+15% CI77499) sold under the name Flamenco Twilight Gold 230ZB by the company BASF Personal Care Ingredients.

According to one preferred mode, the mica-titanium oxide-black iron oxide particles (58% CI77019+18% CI77891+24% CI77499) sold under the name Colorona Patina Silver by the company Merck will be used.

Advantageously, the amount of the reflective particles of mica-titanium oxide-black iron oxide type may range from 15% to 35% by weight and preferably from 20% to 25% by weight relative to the total weight of the composition of the invention.

As other examples of lamellar or platelet-shaped reflective particles with a metallic tint having at the surface a metallic compound or including at least one coated metallic compound, mention may be made of the particles sold under the names Metashine® ME 2040 PS, Metashine® MC5090 PS or Metashine® MC280GP (2523) by the company Nippon Sheet Glass, Silver Flake® JV6 or Gold Powder® A1570 by the company Engelhard, Starlight Reflections FXM® by the company Energy Strategy Associates Inc., Bright Silver® 1 E 0.008×0.008 by the company Meadowbrook Inventions, Ultramin® (Aluminium Poudre Fine Living), and Cosmetic Metallic Powder Visionaire Bright Silver Sea®, Cosmetic Metallic Powder Visionaire Natural Gold® (60314) or Cosmetic Metallic Powder Visionaire Honey® (60316) by the company Eckart, and also Xirona Silver from Merck, and Ronastar Aqua or Ronastar Red from Merck.

The reflective particles with a metallic tint may reflect the visible spectrum substantially uniformly, as is the case, for example, for particles coated with a metal such as silver or aluminium, or may not, which may then lead, for example, to a metallic tint having a yellow, pink, red, bronze, orange, brown and/or coppery non-neutral tone, depending on the nature, for example, of the metallic compound at the surface.

According to a second alternative, the composition according to the invention comprises at least one nonionic surfactant and/or at least one ionic surfactant and/or at least one polymeric surfactant.

Preferably, the composition comprises at least one nonionic surfactant. Preferably, the composition comprises at least one nonionic surfactant with an HLB of greater than or equal to 8 at 25° C. Preferably, the composition comprises, simultaneously, at least one nonionic surfactant and at least one ionic surfactant, which is preferably anionic.

According to the invention, a surfactant appropriately chosen to obtain a wax-in-water or oil-in-water emulsion is generally used. In particular, an emulsifier having at 25° C. an HLB (hydrophilic-lipophilic balance), in the Griffin sense, of greater than or equal to 8 may be used.

The HLB value according to Griffin is defined in J. Soc. Cosm. Chem. 1954 (volume 5), pages 249-256.

These surfactants may be chosen from nonionic, anionic, cationic and amphoteric surfactants or emulsifying surfactants. Reference may be made to the document "Encyclopaedia of Chemical Technology, Kirk-Othmer", volume 22, pp. 333-432, 3rd edition, 1979, Wiley, for the definition of the properties and (emulsifying) functions of surfactants, in particular pp. 347-377 of this reference, for anionic, amphoteric and nonionic surfactants.

The surfactants preferably used in the composition according to the invention are chosen from:

a) nonionic surfactants with an HLB of greater than or equal to 8 at 25° C., used alone or as a mixture; mention may be made especially of:

saccharide esters and ethers such as the mixture of cetyl-stearyl glucoside and of cetyl and stearyl alcohols, for instance Montanov 68 from SEPPIC;

oxyethylenated and/or oxypropylenated ethers (which may comprise from 1 to 150 oxyethylene and/or oxypropylene groups) of glycerol;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohol), such as oxyethylenated cetearyl alcohol ether containing 30 oxyethylene groups (CTFA name Ceteareth-30), oxyethylenated stearyl alcohol ether containing 20 oxyethylene groups (CTFA name Steareth-20) and the oxyethylenated ether of the mixture of $C_{12}$-$C_{15}$ fatty alcohols comprising 7 oxyethylene groups (CTFA name C12-15 Pareth-7) sold under the name Neodol 25-7® by Shell Chemicals;

fatty acid esters (especially of a $C_8$-$C_{24}$ and preferably $C_{16}$-$C_{22}$ acid) of polyethylene glycol (which may comprise from 1 to 150 ethylene glycol units), such as PEG-50 stearate and PEG-40 monostearate sold under the name Myrj 52P® by the company ICI Uniqema;

fatty acid esters (especially of a $C_8$-$C_{24}$ and preferably $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate sold under the name Simulsol 220 TM® by the company SEPPIC; glyceryl stearate polyethoxylated with 30 ethylene oxide groups, for instance the product Tagat S® sold by the company Goldschmidt, glyceryl oleate polyethoxylated with 30 ethylene oxide groups, for instance the product Tagat O® sold by the company Goldschmidt, glyceryl cocoate polyethoxylated with 30 ethylene oxide groups, for instance the product Varionic LI 13® sold by the company Sherex, glyceryl isostearate polyethoxylated with 30 ethylene oxide groups, for instance the product Tagat L® sold by the company Goldschmidt, and glyceryl laurate polyethoxylated with 30 ethylene oxide groups, for instance the product Tagat I® from the company Goldschmidt;

fatty acid esters (especially of a $C_8$-$C_{24}$ and preferably $C_{16}$-$C_{22}$ acid) of oxyethylenated and/or oxypropylenated sorbitol ethers (which may comprise from 1 to 150 oxyethylene and/or oxypropylene groups), for instance polysorbate 20 sold under the name Tween 20® by the company Croda, and polysorbate 60 sold under the name Tween 60® by the company Croda;

dimethicone copolyol, such as the product sold under the name Q2-5220® by the company Dow Corning;

dimethicone copolyol benzoate (Finsolv SLB 101® and 201® by the company Finetex);

copolymers of propylene oxide and of ethylene oxide, also known as EO/PO polycondensates;

and mixtures thereof.

The EO/PO polycondensates are more particularly copolymers consisting of polyethylene glycol and polypropylene glycol blocks, for instance polyethylene glycol/polypropylene glycol/polyethylene glycol triblock polycondensates. These triblock polycondensates have, for example, the following chemical structure:

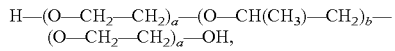

in which formula a ranges from 2 to 120 and b ranges from 1 to 100.

The EO/PO polycondensate preferably has a weight-average molecular weight ranging from 1000 to 15 000 and better still ranging from 2000 to 13 000. Advantageously, the EO/PO polycondensate has a cloud point, at 10 g/l in distilled water, of greater than or equal to 20° C. and preferably greater than or equal to 60° C. The cloud point is measured according to ISO standard 1065. As EO/PO polycondensates that may be used according to the invention, mention may be made of the polyethylene glycol/polypropylene glycol/polyethylene glycol triblock polycondensates sold under the name Synperonic®, for instance Synperonic PE/L44® and Synperonic PE/F127®, by the company ICI.

b) nonionic surfactants with an HLB of less than 8 at 25° C., optionally combined with one or more nonionic surfactants with an HLB of greater than 8 at 25° C., such as those mentioned above, such as:

saccharide esters and ethers, such as sucrose stearate, sucrose cocoate and sorbitan stearate, and mixtures thereof, for instance Arlatone 2121® sold by the company ICI;

oxyethylenated and/or oxypropylenated ethers (which may comprise from 1 to 150 oxyethylene and/or oxypropylene groups) of fatty alcohols (especially of $C_8$-$C_{24}$ and preferably $C_{12}$-$C_{18}$ alcohols) such as the oxyethylenated ether of stearyl alcohol containing two oxyethylene groups (CTFA name Steareth-2);

fatty acid esters (especially of a $C_8$-$C_{24}$ and preferably $C_{16}$-$C_{22}$ acid) of polyols, especially of glycerol or of sorbitol, such as glyceryl stearate, glyceryl stearate such as the product sold under the name Tegin M® by the company Goldschmidt, glyceryl laurate such as the product sold under the name Imwitor 312® by the company Hüls, polyglyceryl-2 stearate, sorbitan tristearate or glyceryl ricinoleate;

lecithins, such as soybean lecithins (for instance Emulmetik 100 J from Cargill, or Biophilic H from Lucas Meyer);

the mixture of cyclomethicone/dimethicone copolyol sold under the name Q2-3225C® by the company Dow Corning, c) anionic surfactants such as:

salts of $C_{16}$-$C_{30}$ fatty acids, especially those derived from amines, for instance triethanolamine stearate and/or 2-amino-2-methyl-1,3-propanediol stearate;

polyoxyethylenated fatty acid salts, especially those derived from amines or alkali metal salts, and mixtures thereof;

phosphoric esters and salts thereof, such as "DEA oleth-10 phosphate" (Crodafos N 10N from the company Croda) or monocetyl monopotassium phosphate (Amphisol K from Givaudan);

sulfosuccinates such as "Disodium PEG-5 citrate lauryl sulfosuccinate" and "Disodium ricinoleamido MEA sulfosuccinate";

alkyl ether sulfates, such as sodium lauryl ether sulfate;

isethionates;

acylglutamates such as "Disodium hydrogenated tallow glutamate" (Amisoft HS-21 R® sold by the company Ajinomoto) and sodium stearoyl glutamate (Amisoft HS-11 PF® sold by the company Ajinomoto), and mixtures thereof;

soybean derivatives, for instance potassium soyate;

citrates, for instance glyceryl stearate citrate (Axol C 62 Pellets from Degussa);

proline derivatives, for instance sodium palmitoyl proline (Sepicalm VG from SEPPIC) or the mixture of sodium palmitoyl sarcosinate, magnesium palmitoyl glutamate, palmitic acid and palmitoyl proline (Sepifeel One from SEPPIC);

lactylates, for instance sodium stearoyl lactylate (Akoline SL from Karlshamns AB);

sarcosinates, for instance sodium palmitoyl sarcosinate (Nikkol sarcosinate PN) or the 75/25 mixture of stearoyl sarcosine and myristoyl sarcosine (Crodasin SM from Croda);

sulfonates, for instance sodium $C_{14}$-$C_{17}$ alkyl sec sulfonate (Hostapur SAS 60 from Clariant);

glycinates, for instance sodium cocoyl glycinate (Amilite GCS-12 from Ajinomoto).

Triethanolamine stearate is most particularly suitable for use in the invention. This agent is generally obtained by simple mixing of stearic acid and triethanolamine.

The compositions in accordance with the invention may also contain one or more amphoteric surfactants, for instance N-acylamino acids such as N-alkylaminoacetates and disodium cocoamphodiacetate, and amine oxides such as stearamine oxide, or alternatively silicone surfactants, for instance dimethicone copolyol phosphates, such as the product sold under the name Pecosil PS 100® by the company Phoenix Chemical.

The surfactant that may be used may also be a polymeric surfactant, especially a heat-induced gelling polymer.

The heat-induced gelling polymers according to the invention are water-soluble and comprise water-soluble units and units having in water a lower critical solution temperature, LCST, the heat-induced demixing temperature in aqueous solution of the units with an LCST being from 5 to 40° C. for a mass concentration in water of 1% of the units and the concentration of the polymer in the composition being such that its gel point is in the range from 5 to 40° C.

The term "water-soluble polymer" generally means a polymer that is soluble in water, at a temperature of from 5 to 80° C., to a proportion of at least 10 g/l and preferably of at least 20 g/l. However, the term "water-soluble polymer" also means a polymer not necessarily having the solubility mentioned above, but which, in aqueous solution at 1% by weight, from 5 to 80° C., allows the production of a macroscopically homogeneous and transparent solution, i.e. a solution with a maximum light transmittance value, irrespective of the wavelength between 400 and 800 nm, through a sample 1 cm thick, of at least 85% and preferably of at least 90%. The term "water-soluble units" generally means that these units are soluble in water, at a temperature of from 5 to 80° C., to a proportion of at least 10 g/l and preferably of at least 20 g/l. However, the term "water-soluble units" also means units not necessarily having the solubility mentioned above, but which, in aqueous solution at 1% by weight, from 5 to 80° C., allow the production of a macroscopically homogeneous and transparent solution, i.e. a solution with a maximum light transmittance value, irrespective of the wavelength between 400 and 800 nm, through a sample 1 cm thick, of at least 85% and preferably of at least 90%. These water-soluble units have no heat-induced demixing temperature of LCST type.

In this respect, it is useful to recall that the expression "units with an LCST" preferably means units whose solubility in water is modified beyond a certain temperature. These are units with a heat-induced demixing temperature (or cloud point) defining their region of solubility in water. The minimum demixing temperature obtained as a function of the concentration of polymer consisting solely of units with an LCST is known as the "LCST" (Lower Critical Solution Temperature). For each concentration of polymer with an LCST, a heat-induced solution temperature is observed. It is higher than the LCST, which is the minimum point of the curve. Below this temperature, the polymer is soluble in water, and above this temperature, the polymer loses its solubility in water.

These units with an LCST of the polymer preferably have, according to the invention, a heat-induced demixing temperature of from 5 to 40° C. for a mass concentration in water of 1% by weight of the units with an LCST.

More preferentially, the heat-induced demixing temperature in aqueous solution of the units with an LCST of the polymer is from 10 to 35° C. for a mass concentration in water of 1% of the units with an LCST. More preferentially, the polymer concentration is such that the gel point is in the range from 10 to 35° C.

The polymer having the structure described above with water-soluble units and specific units with an LCST defined above has in aqueous solution gelation properties beyond a critical temperature, or heat-induced gelling properties.

These heat-induced gelling properties observed beyond the demixing temperature of the chains with an LCST are described especially in the following documents:

[1] D. Hourdet et al., Polymer, 1994, Vol. 35, No. 12, pages 2624-2630.
[2] F. L'Alloret et al., Coll. Polym. Sci., 1995, Vol. 273, No. 12, pages 1163-1173.
[3] F. L'Alloret, Revue de l'Institut Français du Pétrole [Review of the French Petroleum Institute], 1997, Vol. 52, No. 2, pages 117-128.

They are due to the combination of the chains with an LCST within hydrophobic microdomains beyond their demixing temperature, thus forming crosslinking nodes between the main chains.

These gelling properties are observed when the polymer concentration is sufficient to allow interactions between units with an LCST borne by different macromolecules. The minimum concentration required, known as the "critical aggregation concentration", or CAC, is evaluated by rheological measurements: it is the concentration at and above which the viscosity of an aqueous solution of the polymers of the invention becomes higher than the viscosity of a solution of the equivalent polymer not comprising chains with an LCST.

Beyond the CAC, the polymers of the invention have gelling properties when the temperature becomes higher than a critical value, known as the "gel point", or $T_{gel}$. According to the literature data, there is good agreement between $T_{gel}$ and the demixing temperature of the chains with an LCST, under the same concentration conditions. The gel point of an aqueous solution of a polymer of the invention is determined by rheological measurements: it is the temperature at and above which the viscosity of a solution of a polymer of the invention becomes higher than the viscosity of a solution of the equivalent polymer not comprising chains with an LCST.

The polymers of the invention are preferably characterized by a specific gel point generally of from 5 to 40° C. and preferably from 10 to 35° C., for a concentration by mass in water equal to, for example, 2% by weight.

The polymers used in the invention may be block polymers or grafted polymers, which comprise, on the one hand, water-soluble units and, on the other hand, units with an LCST as defined above.

It is pointed out that, in the present text, the water-soluble units or the units with an LCST of the polymers used according to the invention are defined as not including the groups linking together, on the one hand, the water-soluble units and, on the other hand, the units with an LCST.

The linking groups are derived from the reaction, during the preparation of the polymer, of the reactive sites borne, on the one hand, by the precursors of the water-soluble units and, on the other hand, by the precursors of the units with an LCST.

The polymers used in the context of the invention may thus be block polymers comprising, for example, blocks consisting of water-soluble units alternating with blocks with an LCST.

These polymers may also be in the form of grafted polymers whose backbone is formed from water-soluble units, the backbone bearing grafts consisting of units with an LCST.

The polymers may be partially crosslinked.

These water-soluble units may be totally or partially obtained by polymerization, especially free-radical polymerization, or by polycondensation, or may consist totally or partially of existing natural or modified natural polymers.

By way of example, the water-soluble units may be totally or partially obtained by polymerization, especially free-radical polymerization, of at least one monomer chosen from the following monomers:

(meth)acrylic acid;
vinyl monomers of formula (I) below:

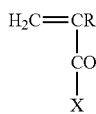

(I)

in which:

R is chosen from H, —CH$_3$, —C$_2$H$_5$ and —C$_3$H$_7$, and

X is chosen from:

alkyl oxides of —OR' type in which R' is a linear or branched, saturated or unsaturated hydrocarbon-based radical containing from 1 to 6 carbon atoms, optionally substituted with at least one halogen atom (iodine, bromine, chlorine or fluorine); a sulfonic (—SO$_3^-$), sulfate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (—N$^+$R$_1$R$_2$R$_3$) group with R$_1$, R$_2$ and R$_3$ being, independently of each other, a linear or branched, saturated or unsaturated hydrocarbon-based radical containing 1 to 6 carbon atoms, with the proviso that the sum of the carbon atoms of R'+R$_1$+R$_2$+R$_3$ does not exceed 7; and —NH$_2$, —NHR$_4$ and —NR$_4$R$_5$ groups in which R$_4$ and R$_5$ are, independently of each other, linear or branched, saturated or unsaturated hydrocarbon-based radicals containing 1 to 6 carbon atoms, with the proviso that the total number of carbon atoms of R$_4$+R$_5$ does not exceed 7, the R$_4$ and R$_5$ optionally being substituted with a halogen atom (iodine, bromine, chlorine or fluorine); a hydroxyl (—OH); sulfonic (—SO$_3^-$); sulfate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon-based radical containing 1 to 6 carbon atoms, with the proviso that the sum of the carbon atoms of R$_4$+R$_5$+R$_1$+R$_2$+R$_3$ does not exceed 7;

maleic anhydride;

itaconic acid;

vinyl alcohol of formula CH$_2$=CHOH;

vinyl acetate of formula CH$_2$=CH—OCOCH$_3$;

N-vinyllactams such as N-vinylpyrrolidone, N-vinylcaprolactam and N-butyrolactam;

vinyl ethers of formula CH$_2$=CHOR$_6$ in which R$_6$ is a linear or branched, saturated or unsaturated hydrocarbon-based radical containing from 1 to 6 carbons;

water-soluble styrene derivatives, especially styrene sulfonate;

dimethyldiallylammonium chloride; and vinylacetamide.

The polycondensates and natural or modified natural polymers which may constitute all or part of the water-soluble units are chosen from one or more of the following components:

water-soluble polyurethanes, xanthan gum, especially the product sold under the names Keltrol T and Keltrol SF by Kelco; or Rhodigel SM and Rhodigel 200 from Rhodia;

alginates (Kelcosol from Monsanto) and derivatives thereof such as propylene glycol alginate (Kelcoloid LVF from Kelco);

cellulose derivatives and especially carboxymethylcellulose (Aquasorb A500, Hercules), hydroxypropylcellulose, hydroxyethylcellulose and quaternized hydroxyethylcellulose;

galactomannans and derivatives thereof, such as Konjac gum, guar gum, hydroxypropyl guar, hydroxypropyl guar modified with sodium methylcarboxylate groups (Jaguar XC97-1, Rhodia), guar hydroxypropyl-trimethylammonium chloride.

Mention may also be made of polyethyleneimine.

The water-soluble units preferably have a molar mass ranging from 1000 g/mol to 5 000 000 g/mol when they constitute the water-soluble backbone of a grafted polymer. These water-soluble units preferably have a molar mass ranging from 500 g/mol to 100 000 g/mol when they constitute a block of a multiblock polymer.

The units with an LCST of the polymers used in the invention may be defined as being units whose water solubility is modified beyond a certain temperature. They are units with a heat-induced demixing temperature (or cloud point) defining their region of solubility in water. The minimum demixing temperature obtained as a function of the polymer concentration is referred to as the "LCST" (Lower Critical Solution Temperature). For each polymer concentration, a heat-induced demixing temperature is observed; it is higher than the LCST, which is the minimum point of the curve. Below this temperature, the polymer constituting the unit with an LCST is soluble in water; above this temperature, the polymer constituting the unit with an LCST loses its solubility in water. Some of these polymers with an LCST are especially described in the following articles:

Taylor et al., Journal of Polymer Science, part A: Polymer Chemistry, 1975, 13, 2551;

J. Bailey et al., Journal of Applied Polymer Science, 1959, 1, 56;

Heskins et al., Journal of Macromolecular Science, Chemistry A2, 1968, Vol. 8, 1441.

The expression "soluble in water at a temperature T" means that the units have a solubility at T of at least 1 g/l and preferably of at least 2 g/l.

The measurement of the LCST may be performed visually: the temperature at which the cloud point of the aqueous solution appears is determined; this cloud point is reflected by the opacification of the solution, or the loss of transparency.

In general, a transparent composition will have a maximum light transmittance value, irrespective of the wavelength between 400 and 800 nm, through a sample 1 cm thick, of at least 85% and preferably of at least 90%. The transmittance may be measured by placing a sample 1 cm thick in the light beam of a spectrophotometer working at the wavelengths of the light spectrum.

The units with an LCST of the polymers used in the invention may consist of one or more polymers chosen from the following polymers:

polyethers such as polypropylene oxide (PPO) or statistical copolymers of ethylene oxide (EO) and of propylene oxide (PO), polyvinyl methyl ethers, polymeric and copolymeric N-substituted acrylamide derivatives containing units with an LCST, such as poly-N-isopropylacrylamide (NIPAM) and poly-N-ethylacrylamide; and polyvinylcaprolactam and vinylcaprolactam copolymers.

Preferably, the units with an LCST consist of polypropylene oxide (PPO)$_n$ where n is an integer from 10 to 70, or of statistical copolymers of ethylene oxide (EO) and of propylene oxide (PO), represented by the formula:

in which m is an integer ranging from 1 to 40 and preferably from 2 to 20, and n is an integer ranging from 10 to 60 and preferably from 20 to 50.

Preferably, the molar mass of these units with an LCST is from 500 to 5300 g/mol and more preferably from 1500 to 4000 g/mol.

It has been found that the random distribution of the EO and PO units is reflected by the existence of a lower critical solution temperature, beyond which a macroscopic phase separation is observed. This behaviour is different from that of block (Eo) (PO) copolymers, which form micelles beyond a critical temperature known as the micellization temperature (microscopic aggregation).

The units with an LCST may thus especially be polypropylene oxides such as the Polyglycols P3000 and P4000 from Dow Chemical, or amino, especially monoamino, diamino or triamino, statistical copolymers of ethylene oxide and of propylene oxide. Before reaction, these polymers bear reactive sites, in this case amino groups, reacting with the reactive sites of the water-soluble polymers, for example carboxyl groups, to give the final polymer used in the invention. In the final polymer, the water-soluble units are linked to the units with an LCST via linking groups derived from the reaction of the reactive sites or groups borne, respectively, by the units with an LCST and the precursors of the water-soluble units. These linking groups will be, for example, amide, ester, ether or urethane groups.

Among these commercially available polymers with an LCST, mention may be made of the copolymers sold under the name Jeffamine by Huntsman, and especially Jeffamine XTJ-507 (M-2005), Jeffamine D-2000 and Jeffamine XTJ-509 (or T-3000).

The units with an LCST may also be derived from random EO/PO copolymers containing OH end groups, such as those sold under the name Polyglycols P41 and B11 by Clariant.

Polymeric and copolymeric N-substituted acrylamide derivatives containing units with an LCST, and also polyvinylcaprolactam and vinylcaprolactam copolymers, may also be used in the invention as units with an LCST.

As examples of polymeric and copolymeric N-substituted acrylamide derivatives containing units with an LCST, mention may be made of poly-N-isopropylacrylamide, poly-N-ethylacrylamide and copolymers of N-isopropylacrylamide (or of N-ethylacrylamide) and of a vinyl monomer chosen from the monomers having the formula (I) given above, maleic anhydride, itaconic acid, vinylpyrrolidone, styrene and its derivatives, dimethyldiallylammonium chloride, vinylacetamide, vinyl ethers and vinyl acetate derivatives.

The molar mass of these polymers is preferably from 1000 g/mol to 500 000 g/mol and preferably from 2000 to 50 000 g/mol.

These polymers may be synthesized by free-radical polymerization using a pair of initiators such as aminoethanethiol hydrochloride, in the presence of potassium persulfate, so as to obtain precursor oligomers with a reactive amino end group.

As examples of vinylcaprolactam copolymers, mention may be made of copolymers of vinylcaprolactam and of a vinyl monomer of formula (I) given above, or of a monomer chosen from maleic anhydride, itaconic acid, vinylpyrrolidone, styrene and its derivatives, dimethyldiallylammonium chloride, vinylacetamide, vinyl alcohol, vinyl acetate, vinyl ethers and vinyl acetate derivatives.

The molar mass of these vinylcaprolactam polymers or copolymers is generally from 1000 g/mol to 500 000 g/mol and preferably from 2000 to 50 000 g/mol.

These compounds may be synthesized by free-radical polymerization using a pair of initiators such as aminoethanethiol hydrochloride, in the presence of potassium persulfate, so as to obtain units with an LCST containing a reactive amino end group.

The mass proportion of the units with an LCST in the final polymer is preferably from 5% to 70%, especially from 10% to 60% and particularly from 20% to 50% by weight relative to the final polymer.

It has been seen hereinabove that the heat-induced demixing temperature of the units with an LCST of the polymer used in the invention is from 5 to 40° C. and preferably from 10 to 35° C., for a concentration by mass in water of 1% by weight of the units with an LCST.

The polymers used in the context of the invention may be readily prepared by a person skilled in the art on the basis of his general knowledge, using grafting, copolymerization or coupling reaction processes.

When the final polymer is in the form of a grafted polymer, especially having a water-soluble backbone with side chains or grafts with an LCST, it is possible to prepare it by grafting units with an LCST containing at least one reactive end group or reactive site, especially an amino end group or site, onto a water-soluble polymer forming the backbone, bearing at least 10% (on a molar basis) of reactive groups such as carboxylic acid functions. This reaction may be carried out in the presence of a carbodiimide such as dicyclohexylcarbodiimide or 1-(3-dimethylaminopropyl)-3-ethylcarbodiimide hydrochloride, in a solvent such as N-methylpyrrolidone or water.

Another possibility for preparing grafted polymers consists in copolymerizing, for example, a macromonomer with an LCST (chain with an LCST described above with a vinyl end group) and a water-soluble vinyl monomer such as acrylic acid or vinyl monomers of formula (I).

When the final polymer is in the form of a block polymer, it is possible to prepare it by coupling between water-soluble units and units with an LCST, these units having complementary reactive sites at each end.

In the case of grafting processes and coupling processes, the reactive sites of the units with an LCST may be amine functions, especially monoamine, diamine or triamine functions, and OH functions. In this case, the reactive sites of the water-soluble units may be carboxylic acid functions. The groups linking the water-soluble units and the units with an LCST will thus be, for example, amide groups or ester groups.

The heat-induced gelling polymers in accordance with the invention may be chosen from those described in the following patents and patent applications:

patent applications EP 1 307 501, EP 1 355 990, EP 1 355 625, FR 2 856 923, EP 1 493 774 and WO 04/006872, U.S. Pat. No. 6,878,754 and U.S. Pat. No. 6,689,856; patent applications EP 1 407 791, EP 1 416 044, FR 2 788 008, WO 03/008462, FR 2 694 939, EP 0 629 649, U.S. Pat. No. 6,645,476, WO 97/00275, WO 98/06438, WO 98/29487, WO 98/48768, WO 98/50005, WO 00/07603, WO 02/076392, FR 2 820 976, WO 00/35961, WO 02/032560, EP 0 692 506, U.S. Pat. No. 6,870,012, WO 03/106536, WO 00/38651, WO 00/00222, WO 01/41735, US2003/0099709, GB 2 408 510.

Heat-induced gelling polymers that are particularly advantageous may be chosen from:

(1) polyurethanes comprising polyethylene oxide/polypropylene oxide/polyethylene oxide (or PEO-PPO-PEO) groups such as those described in patent applications EP 1 407 791 (Example 1 describes a polyurethane derived from the polycondensation of Pluronic F-127 with hexamethylene diisocyanate), EP-A-692 506, FR-A-2 840 907, WO 03/106 536, US-A-2005/175 573 and U.S. Pat. No. 5,702,717.

Such polyurethanes are obtained in a known manner by polycondensation of diisocyanates and of heat-sensitive PEO-PPO-PEO triblock diols and are especially described in the abovementioned patent applications.

Diisocyanates that may be mentioned include aliphatic diisocyanates, for instance ethylene diisocyanate, hexamethylene diisocyanate, decamethylene diisocyanate, and also methylene-4,4'-bis(dicyclohexyl)diisocyanate, diphenylmethane 4,4'-diisocyanate, xylylene diisocyanate, phenylene diisocyanate, tolylene diisocyanate and dimethyl diphenylene diisocyanate.

PEO-PPO-PEO triblock diols used may correspond to formula (I) below:

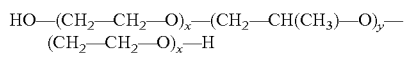

with 20<x<120 and 20<y<120
such as the Pluronic products, especially Pluronic F-127.

The polyurethane may comprise urea and/or allophanate groups, as described in patent applications WO 03/106 536 and U.S. Pat. No. 5,702,717.

The polycondensation may also be performed in the presence of other reactive compounds, for instance diols comprising one or more carboxylic acid groups or a tertiary amine group (especially aminomethyl) or alternatively such as monohydroxylated polyethylene oxides. The polycondensation may especially be performed in the presence of water. The polyurethane may be linear or branched.

(2) multiblock copolymers comprising a poly-N-isopropylacrylamide block and n-butyl acrylate randomly distributed and a polyethylene glycol block, such as those described in patent application EP-A-1 407 791. The product sold under the trade name TGP-20 by the company Mebiol may be used in particular.

(3) copolymers of acrylamidomethylpropanesulfonic acid (or AMPS) such as those described in U.S. Pat. No. 6,645,476 and U.S. Pat. No. 6,689,856, and also the salts thereof (in particular sodium or ammonium salts) and of a macromonomer of an ester of (meth)acrylic acid and of alkoxylated $C_2$-$C_4$ alkyl (in particular ethylene oxide (EO) and/or propylene oxide (PO) (especially containing 1 to 500, more preferentially from 3 to 50 and better still 7 to 30 alkoxylated alkyl units).

Such macromonomers are especially chosen from esters of (meth)acrylic acid with an ether of polyethylene and propylene glycol or alternatively an ether of polyglycol (8 to 25 EO) and of C10 to C22 fatty alcohol) especially chosen from Genapol C-080 or UD-080, or LA-070 or LA-110 or T-080 or T-150 or T-110 or T-200 or T-250 from Clariant.

Such macromonomers may also be derived from amino EO/PO statistical copolymers, especially mono-, di- or triamino copolymers of the Jeffamine type from Huntsman, and especially Jeffamine XTJ-507 (M-2005), Jeffamine D-2000 and Jeffamine XTJ-509 (or T-3000).

Such macromonomers may also be derived from EO/PO statistical copolymers with OH end groups, such as those sold under the name Polyglycols P41 and B11 by Clariant. The copolymer of polyacrylamido-2-methylpropanesulfonic acid (AMPS) neutralized with aqueous ammonia (40% by weight relative to the total weight of the polymer) and of a polyether methacrylate macromonomer (60% by weight) in which the polyether is a PEO/PPO statistical copolymer comprising 5.5 mol of ethylene oxide (EO) units and 31 mol of propylene oxide units.

(4) copolymers such as those described in patent application EP 1 307 501, consisting of a polyacrylic acid (PAA) backbone bearing side chains or grafts consisting of units with an LCST chosen from:

(i) those of the type such as statistical copolymers of ethylene oxide (EO) and of propylene oxide (PO), represented by the formula:

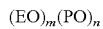

in which m is an integer ranging from 1 to 40 and preferably from 2 to 20, and n is an integer ranging from 10 to 60 and preferably from 20 to 50; the molar mass of these units with an LCST preferably being from 500 to 5300 g/mol and more preferentially from 1500 to 4000 g/mol;

(ii) poly-N-isopropylacrylamide polymers whose molar mass is preferably from 1000 g/mol to 500 000 g/mol and more preferentially from 2000 to 50 000 g/mol.

The surfactant may be present in an amount ranging from 0.1% to 30% by weight, preferably in an amount ranging from 0.5% to 20% by weight and preferably in an amount ranging from 1% to 15% by weight relative to the total weight.

According to a second alternative, the composition according to the invention comprises at least one oil structured with at least one fatty-phase rheological agent.

The fatty-phase rheological agent may be chosen from:
crystalline polymers, preferably chosen from semi-crystalline polymers, fatty acid esters of dextrin, hydrophobic modified polysaccharides, crystalline olefin copolymers and crystalline polycondensates;
mineral lipophilic structuring agents, for instance lipophilic clays and hydrophobic silicas, for instance hydrophobic-treated fumed silica;
polymers of lipophilic polyamide type;
lipophilic polyureas and polyurethanes;
silicone polymers comprising, where appropriate, at least one hydrocarbon-based unit comprising groups capable of establishing hydrogen interactions, chosen from ester, amide, sulfonamide, carbamate, thiocarbamate, urea, urethane, thiourea, oxamido, guanidino and biguanidino groups and combinations thereof, preferably amide groups;
organogelling agents;
block polymers;
cholesterol-based liquid-crystal agents;
and mixtures thereof.

Preferably, the fatty-phase rheological agent is chosen from semi-crystalline polymers, polymers of lipophilic polyamide type, and silicone polymers comprising at least one hydrocarbon-based unit comprising two groups capable of establishing hydrogen interactions, chosen from amide groups.

It is pointed out that, according to the invention, in the case of combinations of a fatty-phase rheological agent with an oil, the term "oil" means a fatty substance that is liquid at room temperature.

It is also pointed out that, for the purposes of the invention, the term "volatile compound", for example "volatile oil", means any compound (or non-aqueous medium) capable of evaporating on contact with the keratin fibres in less than one hour, at room temperature and atmospheric pressure. The volatile compound is a volatile cosmetic compound, which is liquid at room temperature, especially having a non-zero vapour pressure, at room temperature and atmospheric pressure, especially having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

In contrast, the term "non-volatile compound" means a compound that remains on the keratin fibres at room temperature and atmospheric pressure at least for several hours and that especially has a vapour pressure of less than $10^{-3}$ mmHg (0.13 Pa).

The oil may be chosen from volatile and non-volatile hydrocarbon-based oils and/or silicone oils and/or fluoro oils, and mixtures thereof. These oils may be of animal, plant, mineral or synthetic origin. The term "hydrocarbon-based oil" means an oil mainly containing carbon and hydrogen atoms and possibly one or more functions chosen from hydroxyl, ester, ether and carboxylic functions. As examples of oils that may be used in the invention, mention may be made of:

- hydrocarbon-based oils of animal origin such as perhydrosqualene;
- hydrocarbon-based oils of plant origin such as liquid triglycerides of fatty acids containing from 4 to 24 carbon atoms, for instance heptanoic or octanoic acid triglycerides, or alternatively sunflower oil, corn oil, soybean oil, marrow oil, grapeseed oil, sesame seed oil, hazelnut oil, apricot oil, macadamia oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;
- linear or branched hydrocarbons of mineral or synthetic origin, such as liquid paraffins and derivatives thereof, petroleum jelly, polydecenes, polybutenes and hydrogenated polyisobutene such as Parleam;
- synthetic esters and ethers, especially of fatty acids, for instance the oils of formula $R_1COOR_2$ in which $R_1$ represents a higher fatty acid residue containing from 1 to 40 carbon atoms and $R_2$ represents a hydrocarbon-based chain containing from 1 to 40 carbon atoms with $R_1+R_2 \geq 10$, for instance purcellin oil, isononyl isononanoate, isopropyl myristate, 2-ethylhexyl palmitate, 2-octyldodeceyl stearate, 2-octyldodecyl erucate, isostearyl isostearate or tridecyl trimellitate; hydroxylated esters, for instance isostearyl lactate, octyl hydroxystearate, octyl dodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate or diethylene glycol diisononanoate; and pentaerythritol esters, for instance pentaerythrityl tetraisostearate;
- fatty alcohols containing from 12 to 26 carbon atoms, for instance octyldodecanol, 2-butyloctanol, 2-hexyldecanol, 2-undecylpentadecanol or oleyl alcohol;
- fluoro oils which are optionally partially hydrocarbon-based and/or silicone-based;
- silicone oils, for instance volatile or non-volatile, linear or cyclic polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethyl-siloxydiphenylsiloxanes, diphenyl dimethicones, diphenylmethyldiphenyltrisiloxanes and 2-phenyl ethyl trimethyl siloxysilicates;

mixtures thereof.

Preferably, the oil has a molecular mass of greater than or equal to 250 g/mol, especially between 250 and 10 000 g/mol, preferably greater than or equal to 300 g/mol, especially between 300 and 8000 g/mol, and better still greater than or equal to 400 g/mol, especially between 400 and 5000 g/mol.

Generally, in the fatty phase, the ratio of the oil(s) to the particular compound(s) is from 10/90 to 90/10, preferably from 20/80 to 80/20 and more preferably from 30/70 to 70/30.

This oil may be chosen from:

- polybutylenes such as Indopol H-100 (molar mass or MM=965 g/mol), Indopol H-300 (MM=1340 g/mol) and Indopol H-1500 (MM=2160 g/mol), sold or manufactured by the company Amoco,
- hydrogenated polyisobutylenes such as Panalane H-300 E sold or manufactured by the company Amoco (M=1340 g/mol), Viseal 20 000 sold or manufactured by the company Synteal (MM=6000 g/mol) and Rewopal PIB 1000 sold or manufactured by the company Witco (MM=1000 g/mol),
- polydecenes and hydrogenated polydecenes such as: Puresyn 10 (MM=723 g/mol) and Puresyn 150 (MM=9200 g/mol), sold or manufactured by the company Mobil Chemicals,
- esters such as:
  - linear fatty acid esters with a total carbon number ranging from 35 to 70, for instance pentaerythrityl tetrapelargonate (MM=697.05 g/mol),
  - hydroxylated esters such as diisostearyl malate (MM=639 g/mol),
  - aromatic esters such as tridecyl trimellitate (MM=757.19 g/mol),
- esters of branched C24-C28 fatty alcohol or fatty acids, such as those described in patent application EP-A-0 955 039, and in particular triisocetyl citrate (MM=865 g/mol), pentaerythrityl tetraisononanoate (MM=697.05 g/mol), glyceryl triisostearate (MM=891.51 g/mol), glyceryl tris(2-decyl)tetradecanoate (MM=1143.98 g/mol), pentaerythrityl tetraisostearate (MM=1202.02 g/mol), polyglyceryl-2 tetraisostearate (MM=1232.04 g/mol) or pentaerythrityl tetrakis(2-decyl)tetradecanoate (MM=1538.66 g/mol),
- oils of plant origin such as sesame oil (820.6 g/mol), and mixtures thereof.

Crystalline Polymers a) Semi-Crystalline Polymers

It is pointed out that, according to the invention, in the case of the abovementioned combinations, the term "semi-crystalline polymer" means polymers comprising a crystallizable portion, a crystallizable pendent chain or a crystallizable block in the skeleton, and an amorphous portion in the skeleton, and having a first-order reversible temperature of change of phase, in particular of melting (solid-liquid transition). When the crystallizable portion is in the form of a crystallizable block of the polymer skeleton, the amorphous portion of the polymer is in the form of an amorphous block; the semi-crystalline polymer is, in this case, a block copolymer, for example of the diblock, triblock or multiblock type, comprising at least one crystallizable block and at least one amorphous block. The term "block" generally means at least five identical repeating units. The crystallizable block(s) is (are) then of different chemical nature from the amorphous block(s).

The semi-crystalline polymer according to the invention has a melting point of greater than or equal to 30° C. (especially ranging from 30° C. to 80° C.) and preferably ranging from 30° C. to 60° C. This melting point is a first-order temperature of change of state.

This melting point may be measured by any known method and in particular using a differential scanning calorimeter (DSC).

Advantageously, the semi-crystalline polymer(s) to which the invention applies have a number-average molecular mass of greater than or equal to 1000.

Advantageously, the semi-crystalline polymer(s) of the composition of the invention have a number-average molecular mass $\overline{M}n$ ranging from 2000 to 800 000, preferably from 3000 to 500 000, better still from 4000 to 150 000, especially less than 100 000 and better still from 4000 to 99 000. They preferably have a number-average molecular mass of greater than 5600, for example ranging from 5700 to 99 000.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which are pendent or lateral relative to the polymer skeleton. A "block" is a group of atoms belonging to the skeleton, this group constituting one of the repeating units of the polymer. Advantageously, the "pendent crystallizable chain" may be a chain containing at least 6 carbon atoms.

Preferably, the crystallizable block(s) or chain(s) of the semi-crystalline polymers represent at least 30% of the total weight of each polymer and better still at least 40%. The semi-crystalline polymers of the invention containing crystallizable blocks are block or multiblock polymers. They may be obtained by polymerizing a monomer containing reactive (or ethylenic) double bonds or by polycondensation. When the polymers of the invention are polymers containing crystallizable side chains, these side chains are advantageously in random or statistical form.

Preferably, the semi-crystalline polymers which may be used in the composition according to the invention are of synthetic origin. Moreover, they do not comprise a polysaccharide skeleton. In general, the crystallizable units (chains or blocks) of the semi-crystalline polymers according to the invention originate from monomer(s) containing crystallizable block(s) or chain(s), used for the manufacture of the semi-crystalline polymers.

According to the invention, the semi-crystalline polymer may be chosen from block copolymers comprising at least one crystallizable block and at least one amorphous block, and homopolymers and copolymers bearing at least one crystallizable side chain per repeating unit, and mixtures thereof.

The semi-crystalline polymers that may be used in the composition according to the invention are, in particular:
- block copolymers of polyolefins with controlled crystallization, especially those whose monomers are described in EP-A-0 951 897,
- polycondensates, especially of aliphatic or aromatic polyester type or of aliphatic/aromatic copolyester type,
- homopolymers or copolymers bearing at least one crystallizable side chain and homopolymers or copolymers bearing at least one crystallizable block in the skeleton, for instance those described in document U.S. Pat. No. 5,156,911,
- homopolymers or copolymers bearing at least one crystallizable side chain, in particular containing fluoro group(s), as described in document WO-A-01/19333, and mixtures thereof.

In the last two cases, the crystallizable side chain(s) or block(s) are hydrophobic.

A) Semi-Crystalline Polymers Containing Crystallizable Side Chains

Mention may be made in particular of those defined in documents U.S. Pat. No. 5,156,911 and WO-A-01/19333. They are homopolymers or copolymers comprising from 50% to 100% by weight of units resulting from the polymerization of one or more monomers bearing a crystallizable hydrophobic side chain.

These homopolymers or copolymers are of any nature, provided that they meet the conditions mentioned previously.

They can result:
- from the polymerization, especially the free-radical polymerization, of one or more monomers containing reactive or ethylenic double bond(s) with respect to a polymerization, namely a vinyl, (meth)acrylic or allylic group,
- from the polycondensation of one or more monomers bearing co-reactive groups (carboxylic acid, sulfonic acid, alcohol, amine or isocyanate), such as, for example, polyesters, polyurethanes, polyethers, polyureas or polyamides.

In general, these polymers are chosen especially from homopolymers and copolymers resulting from the polymerization of at least one monomer containing crystallizable chain(s) that may be represented by formula X:

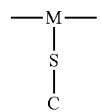

with M representing an atom of the polymer skeleton, S representing a spacer and C representing a crystallizable group.

The crystallizable chains "—S—C" may be aliphatic or aromatic, and optionally fluorinated or perfluorinated. "S" especially represents a group $(CH_2)_n$ or $(CH_2CH_2O)_n$ or $(CH_2O)_n$ which may be linear or branched or cyclic, with n being an integer ranging from 0 to 22. Preferably, "S" is a linear group. Preferably, "S" and "C" are different.

When the crystallizable chains "—S—C" are hydrocarbon-based aliphatic chains, they comprise hydrocarbon-based alkyl chains containing at least 11 carbon atoms and not more than 40 carbon atoms and better still not more than 24 carbon atoms. They are especially aliphatic chains or alkyl chains containing at least 12 carbon atoms, and they are preferably $C_{14}$-$C_{24}$ alkyl chains. When they are fluoroalkyl or perfluoroalkyl chains, they contain at least six fluorinated carbon atoms and especially at least 11 carbon atoms, at least six of which carbon atoms are fluorinated.

As examples of semi-crystalline polymers or copolymers containing crystallizable chain(s), mention may be made of those resulting from the polymerization of one or more of the following monomers: (meth)acrylates of saturated alkyl with the alkyl group being $C_{14}$-$C_{24}$, perfluoroalkyl(meth)acrylates with a $C_{11}$-$C_{15}$ perfluoroalkyl group, N-alkyl(meth)acrylamides with the alkyl group being $C_{14}$ to $C_{24}$ with or without a fluorine atom, vinyl esters containing alkyl or perfluoro (alkyl) chains with the alkyl group being $C_{14}$ to $C_{24}$ (with at least 6 fluorine atoms per perfluoroalkyl chain), vinyl ethers containing alkyl or perfluoro(alkyl) chains with the alkyl group being $C_{14}$ to $C_{24}$ and at least 6 fluorine atoms per perfluoroalkyl chain, $C_{14}$ to $C_{24}$ alpha-olefins such as, for example, octadecene, para-alkylstyrenes with an alkyl group containing from 12 to 24 carbon atoms, and mixtures thereof.

When the polymers result from a polycondensation, the hydrocarbon-based and/or fluorinated crystallizable chains as defined above are borne by a monomer that may be a diacid, a diol, a diamine or a diisocyanate.

When the polymers are copolymers, they additionally contain from 0 to 50% of groups Y or Z resulting from the copolymerization:

α) of Y which is a polar or non-polar monomer or a mixture of the two:

When Y is a polar monomer, it is either a monomer bearing polyoxyalkylenated groups (especially oxyethylenated and/or oxypropylenated groups), a hydroxyalkyl(meth) acrylate, for instance hydroxyethyl acrylate, (meth) acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, a monomer bearing at least one carboxylic acid group, for instance (meth)acrylic acid, crotonic acid, itaconic acid, maleic acid or fumaric acid, or bearing a carboxylic acid anhydride group, for instance maleic anhydride, and mixtures thereof.

When Y is a non-polar monomer, it may be an ester of the linear, branched or cyclic alkyl(meth)acrylate type, a vinyl ester, an alkyl vinyl ether, an alpha-olefin, styrene or styrene substituted with a $C_1$ to $C_{10}$ alkyl group, for instance α-methylstyrene, or a macromonomer of the polyorganosiloxane type containing vinyl unsaturation.

For the purposes of the invention, the term "alkyl" means a saturated group especially of $C_8$ to $C_{24}$, except where otherwise mentioned, and better still of $C_{14}$ to $C_{24}$.

β) of Z which is a polar monomer or a mixture of polar monomers. In this case, Z has the same definition as the "polar Y" defined above.

Preferably, the semi-crystalline polymers containing a crystallizable side chain are alkyl(meth)acrylate or alkyl (meth)acrylamide homopolymers with an alkyl group as defined above, and especially of $C_{14}$-$C_{24}$, copolymers of these monomers with a hydrophilic monomer preferably of different nature from (meth)acrylic acid, for instance N-vinylpyrrolidone or hydroxyethyl(meth)acrylate, and mixtures thereof.

B) Polymers Bearing in the Skeleton at Least One Crystallizable Block

These polymers are especially block copolymers consisting of at least two blocks of different chemical nature, one of which is crystallizable.

The block polymers defined in U.S. Pat. No. 5,156,911 may be used;

Block copolymers of olefin or of cycloolefin containing a crystallizable chain, for instance those derived from the block polymerization of:

cyclobutene, cyclohexene, cyclooctene, norbornene (i.e. bicyclo(2,2,1)-2-heptene), 5-methyl-norbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octa-hydronaphthalene, dicyclopentadiene, or mixtures thereof, with ethylene, propylene, 1-butene, 3-methyl-1-butene, 1-hexene, 4-methyl-1-pentene, 1-octene, 1-decene or 1-eicosene, or mixtures thereof, and in particular copoly(ethylene/norbornene) blocks and (ethylene/propylene/ethylidenenorbornene) block terpolymers. Those resulting from the block copolymerization of at least two $C_2$-$C_{16}$, better still $C_2$-$C_{12}$ and even better still $C_4$-$C_{12}$ α-olefins such as those mentioned above and in particular block bipolymers of ethylene and of 1-octene may also be used.

The copolymers may be copolymers containing at least one crystallizable block, the copolymer residue being amorphous (at room temperature). These copolymers may also contain two crystallizable blocks of different chemical nature. The preferred copolymers are those that simultaneously contain at room temperature a crystallizable block and an amorphous block that are both hydrophobic and lipophilic, sequentially distributed; mention may be made, for example, of polymers containing one of the crystallizable blocks and one of the amorphous blocks below:

Block that is crystallizable by nature: a) polyester, for instance poly(alkylene terephthalate), b) polyolefin, for instance polyethylenes or polypropylenes.

Amorphous and lipophilic block, for instance amorphous polyolefins or copoly(olefin)s such as poly(isobutylene), hydrogenated polybutadiene or hydrogenated poly(isoprene).

As examples of such copolymers containing a crystallizable block and a separate amorphous block, mention may be made of:

α) poly(ε-caprolactone)-b-poly(butadiene) block copolymers, preferably used hydrogenated, such as those described in the article "Melting behaviour of poly(ε-caprolactone)-block-polybutadiene copolymers" from S. Nojima, Macromolecules, 32, 3727-3734 (1999), β) the hydrogenated block or multiblock poly(butylene terephthalate)-b-poly(isoprene) block copolymers cited in the article "Study of morphological and mechanical properties of PP/PBT" by B. Boutevin et al., Polymer Bulletin, 34, 117-123 (1995), γ) the poly(ethylene)-b-copoly(ethylene/propylene) block copolymers cited in the articles "Morphology of semi-crystalline block copolymers of ethylene-(ethylene-alt-propylene)" by P. Rangarajan et al., Macromolecules, 26, 4640-4645 (1993) and "Polymer aggregates with crystalline cores: the system poly(ethylene)-poly(ethylene-propylene)" by P. Richter et al., Macromolecules, 30, 1053-1068 (1997), δ) the poly(ethylene)-b-poly(ethylethylene) block copolymers cited in the general article "Crystallization in block copolymers" by I. W. Hamley, Advances in Polymer Science, Vol. 148, 113-137 (1999).

The semi-crystalline polymers in the composition of the invention may or may not be partially crosslinked, provided that the degree of crosslinking does not interfere with their dissolution or dispersion in the liquid fatty phase optionally present in the composition by heating above their melting point. It may then be a chemical crosslinking, by reaction with a multifunctional monomer during the polymerization. It may also be a physical crosslinking which may, in this case, be due either to the establishment of bonds of hydrogen or dipolar type between groups borne by the polymer, such as, for example, the dipolar interactions between carboxylate ionomers, these interactions being of small amount and borne by the polymer skeleton; or to a phase separation between the crystallizable blocks and the amorphous blocks borne by the polymer.

Preferably, the semi-crystalline polymers in the composition according to the invention are non-crosslinked.

According to one particular embodiment of the invention, the polymer is chosen from copolymers resulting from the polymerization of at least one monomer containing a crystallizable chain chosen from saturated $C_{14}$ to $C_{24}$ alkyl(meth) acrylates, $C_{11}$ to $C_{15}$ perfluoroalkyl(meth)acrylates, $C_{14}$ to $C_{24}$ N-alkyl(meth)acrylamides with or without a fluorine atom, vinyl esters containing $C_{14}$ to $C_{24}$ alkyl or perfluoroalkyl chains, vinyl ethers containing $C_{14}$ to $C_{24}$ alkyl or perfluoroalkyl chains, $C_{14}$ to $C_{24}$ alpha-olefins, para-alkylstyrenes with an alkyl group containing from 12 to 24 carbon atoms, with at least one optionally fluorinated $C_1$ to $C_{10}$ monocarboxylic acid ester or amide, which may be represented by the following formula:

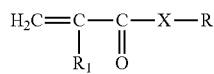

in which $R_1$ is H or $CH_3$, R represents an optionally fluorinated $C_1$-$C_{10}$ alkyl group and X represents O, NH or $NR_2$ in which $R_2$ represents an optionally fluorinated $C_1$-$C_{10}$ alkyl group.

According to one more particular embodiment of the invention, the polymer is derived from a monomer containing a crystallizable chain, chosen from saturated $C_{14}$ to $C_{22}$ alkyl (meth)acrylates.

As specific examples of the semi-crystalline polymers that may be used in the composition according to the invention, mention may be made of the products Intelimer® from the company Landec, described in the brochure "Intelimer® polymers". These polymers are in solid form at room temperature (25° C.). They bear crystallizable side chains and have the formula X above.

The semi-crystalline polymers may especially be:
those described in Examples 3, 4, 5, 7, 9 and 13 of U.S. Pat. No. 5,156,911 containing a —COOH group, resulting from the copolymerization of acrylic acid and of $C_5$ to $C_{16}$ alkyl (meth)acrylate and more particularly of the copolymerization:
of acrylic acid, of hexadecyl acrylate and of isodecyl acrylate in a 1/16/3 weight ratio,
of acrylic acid and of pentadecyl acrylate in a 1/19 weight ratio,
of acrylic acid, of hexadecyl acrylate and of ethyl acrylate in a 2.5/76.5/20 weight ratio,
of acrylic acid, of hexadecyl acrylate and of methyl acrylate in a 5/85/10 weight ratio,
of acrylic acid and of octadecyl methacrylate in a 2.5/97.5 weight ratio,
of hexadecyl acrylate, of polyethylene glycol methacrylate monomethyl ether containing 8 ethylene glycol units, and of acrylic acid in an 8.5/1/0.5 weight ratio.

It is also possible to use the structure "O" from National Starch, as described in document U.S. Pat. No. 5,736,125, with a melting point of 44° C., and also semi-crystalline polymers with crystallizable pendent chains comprising fluoro groups, as described in Examples 1, 4, 6, 7 and 8 of document WO-A-01/19333.

It is also possible to use the semi-crystalline polymers obtained by copolymerization of stearyl acrylate and of acrylic acid or NVP as described in document U.S. Pat. No. 5,519,063 or EP-A-550 745, with melting points of 40° C. and 38° C., respectively.

It is also possible to use the semi-crystalline polymers obtained by copolymerization of behenyl acrylate and of acrylic acid or NVP as described in documents U.S. Pat. No. 5,519,063 and EP-A-550 745, with melting points of 60° C. and 58° C., respectively.

Preferably, the semi-crystalline polymers do not comprise any carboxylic groups.

b) Fatty Acid Esters of Dextrin

The fatty acid esters of dextrin may be chosen especially from monoesters or polyesters of dextrin and of at least one fatty acid, and the compounds corresponding to formula (C):

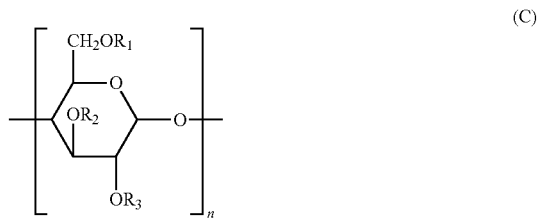

in which:
n is an integer ranging from 3 to 200, especially ranging from 20 to 150 and in particular ranging from 25 to 50,
the radicals $R_1$, $R_2$ and $R_3$, which may be identical or different, are chosen from hydrogen and an acyl group (R—CO—) in which the radical R is a linear or branched, saturated or unsaturated hydrocarbon-based group containing from 7 to 29, in particular from 7 to 21, especially from 11 to 19, more particularly from 13 to 17, or even 15, carbon atoms, with the proviso that at least one of the radicals $R_1$, $R_2$ or $R_3$ is other than hydrogen.

In particular, $R_1$, $R_2$ and $R_3$ may represent hydrogen or an acyl group (R—CO—) in which R is a hydrocarbon-based radical as defined above, with the proviso that at least two of the radicals $R_1$, $R_2$ or $R_3$ are identical and other than hydrogen.

The radicals $R_1$, $R_2$ and $R_3$ may all contain an acyl group (R—CO), which is identical or different and especially identical.

In particular, n advantageously ranges from 25 to 50 and is especially equal to 38 in the general formula (C) of the ester according to the invention.

When the radicals $R_1$, $R_2$ and/or $R_3$, which may be identical or different, contain an acyl group (R—CO), these radicals may be chosen especially from caprylic, capric, lauric, myristic, palmitic, stearic, arachic, behenic, isobutyric, isovaleric, 2-ethylbutyric, ethylmethylacetic, isoheptanoic, 2-ethylhexanoic, isononanoic, isodecanoic, isotridecanoic, isomyristic, isopalmitic, isostearic, isoarachic, isohexanoic, decenoic, dodecenoic, tetradecenoic, myristoleic, hexadecenoic, palmitoleic, oleic, elaidic, asclepinic, gondoleic, eicosenoic, sorbic, linoleic, linolenic, punicic, stearidonic, arachidonic and stearolic radicals, and mixtures thereof.

Preferably, at least one dextrin palmitate is used as fatty acid ester of dextrin. This ester may be used alone or as a mixture with other esters.

Advantageously, the fatty acid ester of dextrin has a degree of substitution of less than or equal to 2.5, especially ranging from 1.5 to 2.5, and preferably from 2 to 2.5, on the basis of one glucose unit. The weight-average molecular weight of the dextrin ester may in particular be from 10 000 to 150 000, especially from 12 000 to 100 000, or even from 15 000 to 80 000.

Dextrin esters, in particular dextrin palmitates, are commercially available under the name Rheopearl TL or Rheopearl KL by the company Chiba Flour.

c) Hydrophobic Modified Polysaccharides

The polysaccharide used in the present invention is preferably chosen from fructans.

Fructans or fructosans are oligosaccharides or polysaccharides comprising a sequence of anhydrofructose units optionally combined with one or more saccharide residues other than fructose. Fructans may be linear or branched. The fructans may be products obtained directly from a plant or microbial source, or alternatively products whose chain length has been modified (increased or reduced) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are mostly linked together via β-2-1 bonds. These are essentially linear fructans such as inulins. The second group also corresponds to linear fructoses, but the fructose units are essentially linked together via β-2-6 bonds. These products are levans. The third group corresponds to mixed fructans, i.e. fructans containing β-2-6 and β-2-1 sequences. These are essentially branched fructans such as graminans.

The fructans used in the compositions according to the invention are inulins. Inulin may be obtained, for example, from chicory, dahlia or Jerusalem artichoke. Preferably, the inulin used in the composition according to the invention is obtained, for example, from chicory.

The polysaccharides, in particular the inulins, used in the compositions according to the invention are hydrophobic-modified. In particular, they are obtained by grafting hydrophobic chains onto the hydrophilic backbone of the fructan.

The hydrophobic chains that may be grafted onto the main chain of the fructan may especially be linear or branched, saturated or unsaturated hydrocarbon-based chains containing from 1 to 50 carbon atoms, such as alkyl, arylalkyl, alkylaryl or alkylene groups; cycloaliphatic divalent groups or organopolysiloxane chains. These hydrocarbon-based or organopolysiloxane chains may especially comprise one or more ester, amide, urethane, carbamate, thiocarbamate, urea, thiourea and/or sulfonamide functions such as, especially, methylenedicyclohexyl and isophorone; or aromatic divalent groups such as phenylene.

In particular, the polysaccharide, especially the inulin, has a degree of polymerization from 2 to about 1000 and preferably from 2 to about 60, and a degree of substitution of less than 2 on the basis of one fructose unit.

According to one preferred embodiment, the hydrophobic chains contain at least one alkyl carbamate group of formula R—NH—CO— in which R is an alkyl group containing from 1 to 22 carbon atoms.

According to one more preferred embodiment, the hydrophobic chains are lauryl carbamate groups.

In particular, as non-limiting illustrations of hydrophobic modified inulins that may be used in the compositions according to the invention, mention may be made of stearoyl inulin, such as the products sold under the names Lifidrem INST by the company Engelhard and Rheopearl INS by the company Ciba; palmitoyl inulin; undecylenoyl inulin, such as the products sold under the names Lifidrem INUK and Lifidrem INUM by the company Engelhard; and inulin lauryl carbamate, such as the product sold under the name Inutec SP1 by the company orafti.

In particular, the hydrophobic-modified polysaccharide is an inulin grafted with lauryl carbamate, which is obtained especially from the reaction of lauryl isocyanate with an inulin, in particular obtained from chicory. An example of these compounds that may especially be mentioned is the product sold under the name Inutec SP1 by the company Orafti.

d) Crystalline Olefin Copolymers

The crystalline olefin copolymer used in the compositions of the present patent application may be any olefin copolymer, i.e. a copolymer comprising only olefin units, having a controlled and moderate crystalline nature, i.e. a degree of crystallinity of not more than 50%, preferably between 5% and 40% and better still between 10% and 35%.

These copolymers are generally elastomers or plastomers and may be synthesized via any known process, in particular via a radical route, via Ziegler-Natta catalysis or via metallocene catalysis, preferably via metallocene catalysis.

A first class of crystalline olefin copolymers that may be used in the compositions according to the invention is that of α-olefin copolymers, in particular of $C_2$-$C_{16}$ and better still $C_2$-$C_{12}$ α-olefin. Preferably, these copolymers are bipolymers or terpolymers and most particularly bipolymers.

Among the bipolymers that are recommended for the compositions of the invention, mention may be made of bipolymers of ethylene and of a $C_4$-$C_{16}$ and preferably $C_4$-$C_{12}$ α-olefin and bipolymers of propylene and of a $C_4$-$C_{16}$ and preferably $C_4$-$C_{12}$ α-olefin. More preferably, the α-olefin is chosen from 1-butene, 1-pentene, 1-hexene, 1-octene, 1-nonene, 1-decene, 1-undecene, 1-dodecene, 3,5,5-trimethyl-1-hexene, 3-methyl-1-pentene and 4-methyl-1-pentene.

Among these monomers, 1-butene and 1-octene are particularly preferred.

The content of α-olefin in the bipolymer is generally between 2 mol % and 40 mol %, preferably 3 mol % to 30 mol % and better still 4 mol % to 20 mol %.

The recommended ethylene-octene bipolymers are plastomers with an octene content of between 5.2 mol % and 6.2 mol % and a degree of crystallinity of between 28% and 38%, and elastomers with an octene content of between 8 mol % and 14 mol % and a degree of crystallinity of between 10% and 28%.

These bipolymers are synthesized via metallocene catalysis.

Such bipolymers are sold by the company Dow Chemical under the trade names Affinity® (plastomers) and Engage® (elastomers).

Ethylene-butene bipolymers are sold by the company Exxon under the trade name Exact Resins®.

Among the terpolymers, mention may be made of terpolymers of ethylene, propylene and a $C_4$-$C_{16}$ and preferably $C_4$-$C_{12}$ α-olefin.

In these terpolymers, the contents of $C_4$-$C_{16}$ α-olefin are as indicated previously and the preferred α-olefins are butene, hexene and octene.

A second class of olefin copolymers that are suitable for use in the compositions according to the invention is that of copolymers of ethylene or of propylene and of a cycloolefin, in particular bipolymers.

Generally, the cycloolefin content of the copolymers is less than 20 mol %.

Among the cycloolefins that may be used, mention may be made of cyclobutene, cyclohexene, cyclooctadiene, norbornene, dimethanooctahydronaphthalene (DMON), ethylidenenorbornene, vinylnorbornene and 4-vinylcyclohexene.

The recommended copolymers of this class are copolymers of ethylene and of norbornene. The norbornene content of these copolymers is generally less than 18 mol % to have the required crystalline nature, and these copolymers are synthesized via metallocene catalysis.

Suitable ethylene/norbornene copolymers are sold by the companies Mitsui Petrochemical or Mitsui-Sekka under the trade name Apel® and by the company Hoechst-Celanese under the trade name Topas®.

Other recommended ethylene/cycloolefin copolymers are ethylene/cyclobutene and ethylene/cyclohexene bipolymers with a low content of cycloolefin, generally less than 20 mol %.

A third class of suitable olefin copolymers is formed by olefin copolymers of controlled tacticity, i.e. copolymers comprising units of different tacticity.

Among these copolymers of controlled tacticity, mention may be made of isotactic propylene/atactic propylene and syndiotactic propylene/atactic propylene copolymers.

The isotactic or syndiotactic units or blocks give the copolymer the crystalline nature, whereas the amorphous atactic units or blocks prevent excessive crystallinity of the copolymer and regulate the degree of crystallinity and also the morphology and size of the crystallites.

The content of isotactic or syndiotactic units, the units which give the copolymer the crystalline nature, is thus determined so as to obtain the desired percentage of crystallinity (≤50%) in the copolymer.

The content of tactic units is generally between 10 mol % and 80 mol %. However, preferably, the content of atactic units is less than 30 mol %.

These copolymers are synthesized via metallocene catalysis.

A fourth class of olefin copolymers that is suitable for use in the present invention is formed by copolymers of monoolefin and of diene, for example ethylene/butadiene, propylene/butadiene, ethylene/isoprene and propylene/isoprene bipolymers, and ethylene/propylene/diene terpolymers, also obtained via metallocene synthesis.

The proportion of diene units in the copolymer of controlled crystallization is generally between 3 mol % and 20 mol %.

To improve the control of the crystallinity of the copolymer, crystallization-impeding additives that promote the formation of small crystals may optionally be added to the composition according to the invention. These additives, although used in small proportion, constitute numerous small germination "sites" uniformly distributed in the bulk. These additives are typically crystals of an organic or mineral substance.

In the case of an organic additive that needs to crystallize, it should have a melting point higher than the melting region of the copolymer and should preferably form small crystals.

At a temperature above its melting point, this substance is preferably soluble in the mixture of the liquid fatty phase and of the polymer melt. Thus, during cooling, the initially-dissolved additive recrystallizes in the form of numerous small crystals widely dispersed in the mixture, and the polymer then recrystallizes to give small crystal domains due to the presence of the additive crystals. This polymer recrystallization technique is standard.

The degree of crystallization, size and morphology of the olefin copolymers according to the invention may also be adjusted by mixing a first olefin copolymer according to the invention with a second crystalline polymer or copolymer, which is partially compatible with the first olefin copolymer. The second polymer or copolymer may be an olefin copolymer according to the invention, but having a degree of crystallinity different from that of the first copolymer, including a degree of crystallinity higher than the degree of crystallinity of the olefin copolymers according to the invention.

The second crystallizable polymer may also be a polymer of different nature, for example a copolyethylene/vinyl acetate obtained by radical copolymerization or even a crystallizable polyethylene such as those usually used in cosmetics.

For further details regarding this method for adjusting the degree of crystallinity, reference may be made to the articles entitled "Elastomeric blends of homogeneous ethylene-octene copolymers", S. Bensason et al., Polymer, Volume 38, No. 15, 1997, pages 3913-19, and "Blends of homogeneous ethylene-octene copolymers", S. Bensason et al., Polymer, Volume 38, No. 14, 1997, pages 3513-20.

d) Crystalline Polycondensates

The polycondensate that may be used may be obtained by reacting:

from 10% to 30% by weight, relative to the total weight of the polycondensate, of at least one polyol comprising 3 to 6 hydroxyl groups;

from 30% to 80% by weight, relative to the total weight of the polycondensate, of at least one saturated or unsaturated, linear, branched and/or cyclic non-aromatic monocarboxylic acid containing 6 to 32 carbon atoms;

from 0.1% to 10% by weight, relative to the total weight of the polycondensate, of at least one aromatic monocarboxylic acid containing 7 to 11 carbon atoms, optionally also substituted with 1 to 3 saturated or unsaturated, linear, branched and/or cyclic alkyl radicals containing 1 to 32 carbon atoms;

from 5% to 40% by weight, relative to the total weight of the polycondensate, of at least one saturated or unsaturated, or even aromatic, linear, branched and/or cyclic or polycarboxylic acid comprising at least two carboxylic groups COOH and especially 2 to 4 COOH groups; and/or a cyclic anhydride of such a polycarboxylic acid.

Preferably, the polycondensate may be obtained by reacting:

10% by weight of at least one aromatic monocarboxylic acid containing 7 to 11 carbon atoms, optionally also substituted with 1 to 3 saturated or unsaturated, linear, branched and/or cyclic alkyl radicals containing 1 to 32 carbon atoms; and from 15% to 30% by weight, relative to the total weight of the polycondensate, of at least one polyol comprising 3 to 6 hydroxyl groups; and from 30% to 40% by weight, relative to the total weight of the polycondensate, of at least one saturated or unsaturated, linear, branched and/or cyclic non-aromatic monocarboxylic acid containing 6 to 32 carbon atoms; and from 10% to 25% by weight, relative to the total weight of the polycondensate, of at least one saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid;

these conditions being cumulative, then the ratio between the number of moles of aromatic monocarboxylic acid and the number of moles of non-aromatic monocarboxylic acid is between 0.08 and 0.70.

The polycondensate may also be obtained by reacting:

from 10% to 30% by weight, relative to the total weight of the polycondensate, of at least one polyol comprising 3 to 6 hydroxyl groups;

from 45% to 80% by weight, relative to the total weight of the polycondensate, of at least one saturated, linear, branched and/or cyclic non-aromatic monocarboxylic acid containing 6 to 32 carbon atoms;

from 0.1% to 10% by weight, relative to the total weight of the polycondensate, of at least one aromatic monocarboxylic acid containing 7 to 11 carbon atoms, optionally also substituted with 1 to 3 saturated or unsaturated, linear, branched and/or cyclic alkyl radicals containing 1 to 32 carbon atoms;

from 5% to 40% by weight, relative to the total weight of the polycondensate, of at least one saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid.

One of the constituents necessary for the preparation of the polycondensates according to the invention is a compound comprising 3 to 6 hydroxyl groups (polyol), especially 3 to 4 hydroxyl groups. A mixture of such polyols may obviously be used. The polyol may especially be a linear, branched and/or cyclic, saturated or unsaturated carbon-based and especially hydrocarbon-based compound, containing 3 to 18 carbon atoms, especially 3 to 12 or even 4 to 10 carbon atoms, and 3 to 6 hydroxyl (OH) groups, and also possibly comprising one or more oxygen atoms intercalated in the chain (ether function). The polyol is preferably a linear or branched saturated hydrocarbon-based compound containing 3 to 18 carbon atoms, especially 3 to 12 or even 4 to 10 carbon atoms, and 3 to 6 hydroxyl (OH) groups. It may be chosen, alone or as a mixture, from:

triols such as 1,2,4-butanetriol, 1,2,6-hexanetriol, trimethylolethane, trimethylolpropane or glycerol;
tetraols such as pentaerythritol (tetramethylol-methane), erythritol, diglycerol or ditrimethylolpropane;
pentols such as xylitol;
hexyls such as sorbitol and mannitol; or alternatively dipentaerythritol or triglycerol.

Preferably, the polyol is chosen from glycerol, pentaerythritol, diglycerol and sorbitol, and mixtures thereof, and better still the polyol is a tetraol such as pentaerythritol. The polyol, or the polyol mixture, preferably represents 10% to 30% by weight, especially 12% to 25% by weight and better still 14% to 22% by weight relative to the total weight of the final polycondensate.

Another constituent necessary for the preparation of the polycondensates according to the invention is a saturated or unsaturated, linear, branched and/or cyclic non-aromatic monocarboxylic acid containing 6 to 32 carbon atoms, especially 8 to 28 carbon atoms and better still 10 to 24 or even 12 to 20 carbon atoms. A mixture of such non-aromatic monocarboxylic acids may obviously be used. The term "non-aromatic monocarboxylic acid" means a compound of formula RCOOH, in which R is a saturated or unsaturated, linear, branched and/or cyclic hydrocarbon-based radical containing 5 to 31 carbon atoms, especially 7 to 27 carbon atoms and better still 9 to 23 carbon atoms or even 11 to 19 carbon atoms. Preferably, the radical R is saturated. Better still, the radical R is linear or branched, and is preferably of C5-C31 or even of C11-C21.

In one particular embodiment of the invention, the non-aromatic monocarboxylic acid has a melting point of greater than or equal to 25° C., preferably greater than or equal to 28° C., or even 30° C.; the reason for this is that it has been found that, when such an acid is used, in particular in large amount, it is possible firstly to obtain good gloss and good staying power of the gloss, and secondly to reduce the amount of waxes usually present in the intended composition.

Among the non-aromatic monocarboxylic acids that may be used, mention may be made, alone or as a mixture, of:

saturated monocarboxylic acids such as caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid;
unsaturated but non-aromatic monocarboxylic acids, such as caproleic acid, obtusilic acid, undecylenic acid, dodecylenic acid, linderic acid, myristoleic acid, physeteric acid, tsuzunic acid, palmitoleic acid, oleic acid, petroselinic acid, vaccenic acid, elaidic acid, gondoic acid, gadoleic acid, erucic acid, ketoleic acid, nervonic acid, linoleic acid, linolenic acid or arachidonic acid.

Among the non-aromatic monocarboxylic acids mentioned above with a melting point of greater than or equal to 25° C., mention may be made, alone or as a mixture, of:
among the saturated monocarboxylic acids: decanoic (capric) acid, lauric acid, tridecanoic acid, myristic acid, palmitic acid, stearic acid, arachidic acid, behenic acid, cerotic (hexacosanoic) acid;
among the unsaturated but non-aromatic monocarboxylic acids: petroselinic acid, vaccenic acid, elaidic acid, gondoic acid, gadoleic acid, erucic acid, nervonic acid.

2-Ethylhexanoic acid, isooctanoic acid, lauric acid, myristic acid, isoheptanoic acid, isononanoic acid, nonanoic acid, palmitic acid, isostearic acid, stearic acid or behenic acid, and mixtures thereof, and better still isostearic acid alone or stearic acid alone, may preferably be used.

The non-aromatic monocarboxylic acid, or the mixture of the acids, preferably represents 30% to 80% by weight, especially 40% to 75% by weight, or even 45% to 70% by weight and better still 50% to 65% by weight, relative to the total weight of the final polycondensate.

Another constituent necessary for the preparation of the polycondensates according to the invention is an aromatic monocarboxylic acid containing 7 to 11 carbon atoms, also optionally substituted with 1 to 3 saturated or unsaturated, linear, branched and/or cyclic alkyl radicals containing 1 to 32 carbon atoms, especially 2 to 12 or even 3 to 8 carbon atoms. A mixture of such aromatic monocarboxylic acids may obviously be used.

The term "aromatic monocarboxylic acid" means a compound of formula R'COOH in which R' is an aromatic hydrocarbon-based radical containing 6 to 10 carbon atoms, and in particular benzoic and naphthoic radicals. The radical R' may also be substituted with 1 to 3 saturated or unsaturated, linear, branched and/or cyclic alkyl radicals containing 1 to 32 carbon atoms, especially 2 to 12 or even 3 to 8 carbon atoms; and especially chosen from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl and isooctyl. Among the aromatic monocarboxylic acids that may be used, mention may be made, alone or as a mixture, of benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid. Benzoic acid, 4-tert-butylbenzoic acid, o-toluic acid, m-toluic acid or 1-naphthoic acid, alone or as mixtures, and better still benzoic acid alone, may preferably be used. The aromatic monocarboxylic acid, or the mixture of the acids, preferably represents from 0.1% to 10% by weight, especially 0.5% to 9.95% by weight, better still from 1% to 9.5% by weight or even 1.5% to 8% by weight, relative to the total weight of the final polycondensate.

Another constituent necessary for the preparation of the polycondensates according to the invention is a saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid. A mixture of such polycarboxylic acids and/or anhydrides may obviously be used. The polycarboxylic acid may especially be chosen from linear, branched and/or cyclic, saturated or unsaturated, or even aromatic, polycarboxylic acids containing 2 to 50 carbon atoms, especially 2 to 40 and in particular 3 to 36 carbon atoms, or even 3 to 18 and better still 4 to 12 carbon atoms, or even 4 to 10 carbon atoms; the acid comprises at least two carboxylic groups COOH and preferably from 2 to 4 COOH groups.

Preferably, the polycarboxylic acid is aliphatic and contains 3 to 36 carbon atoms, especially 3 to 18 carbon atoms or even 4 to 12 carbon atoms; or alternatively is aromatic and contains 8 to 12 carbon atoms. It preferably comprises 2 to 4 COOH groups. The cyclic anhydride of such a polycarboxylic acid may especially correspond to one of the following formulae:

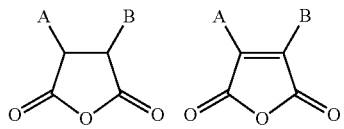

in which the groups A and B are, independently of each other:
- a hydrogen atom;
- a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl;
- or alternatively A and B, taken together, form a saturated or unsaturated, or even aromatic, ring containing in total 5 to 7 and especially 6 carbon atoms.

Preferably, A and B represent a hydrogen atom or together form an aromatic ring containing in total 6 carbon atoms.

Among the polycarboxylic acids or anhydrides thereof that may be used, mention may be made, alone or as a mixture, of:
- dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, tetrahydrophthalic acid, hexahydrophthalic acid, pimelic acid, sebacic acid, azelaic acid, glutaric acid, adipic acid, fumaric acid, maleic acid, itaconic acid, and fatty acid dimers (especially of C36) such as the products sold under the names Pripol 1006, 1009, 1013 and 1017 by Uniqema;
- tricarboxylic acids such as cyclohexanetricarboxylic acid, trimellitic acid, 1,2,3-benzenetricarboxylic acid or 1,3,5-benzenetricarboxylic acid;
- tetracarboxylic acids such as butanetetracarboxylic acid and pyromellitic acid;
- cyclic anhydrides of these acids and especially phthalic anhydride, trimellitic anhydride, maleic anhydride and succinic anhydride.

Adipic acid, phthalic anhydride and/or isophthalic acid, and better still isophthalic acid alone, may preferably be used.

The polycarboxylic acid and/or the cyclic anhydride thereof preferably represents 5% to 40% by weight, especially 10% to 30% by weight and better still 40% to 25% by weight relative to the total weight of the final polycondensate.

The polycondensate according to the invention may also comprise a silicone containing hydroxyl (OH) and/or carboxylic (COOH) functions.

It may comprise 1 to 3 hydroxyl and/or carboxylic functions, and preferably comprises two hydroxyl functions or two carboxylic functions.

These functions may be located at the end of a chain or in the chain, but advantageously at the end of the chain.

Silicones with a weight-average molecular mass (Mw) of between 300 and 20 000, especially 400 and 10 000 or even 800 and 4000, are preferably used.

This silicone may be of the formula:

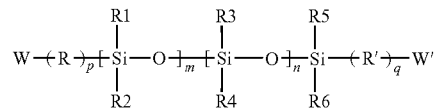

in which:
- W and W' are, independently of each other, OH or COOH; preferably, W=W';
- p and q are, independently of each other, equal to 0 or 1;
- R and R' are, independently of each other, a saturated or unsaturated, or even aromatic, linear, branched and/or cyclic carbon-based and especially hydrocarbon-based divalent radical; containing 1 to 12 carbon atoms and especially 2 to 8 carbon atoms, and optionally also comprising one or more heteroatoms chosen from O, S and N, especially O (ether);
- R and/or R' may especially be of formula $-(CH_2)_a-$ with a=1-12, and especially methylene, ethylene, propylene or phenylene;
  or alternatively of formula $-[(CH_2)_xO]_z-$ with x=1, 2 or 3 and z=1-10; in particular x=2 or 3 and z=1-4; and better still x=3 and z=1;
- R1 to R6 are, independently of each other, a linear, branched and/or cyclic, saturated or unsaturated, or even aromatic, carbon-based radical containing 1 to 20 carbon atoms and especially 2 to 12 carbon atoms; preferably, R1 to R6 are saturated or aromatic, and may be chosen especially from alkyl radicals, in particular methyl, ethyl, propyl, isopropyl, butyl, pentyl, hexyl, octyl, decyl, dodecyl and octadecyl radicals, cycloalkyl radicals, in particular the cyclohexyl radical, aryl radicals, especially phenyl and naphthyl, arylalkyl radicals, especially benzyl and phenylethyl, and also tolyl and xylyl radicals;
- m and n are, independently of each other, integers between 1 and 140, and are such that the weight-average molecular mass (Mw) of the silicone is between 300 and 20 000, especially between 400 and 10 000 or even between 800 and 4000.

Mention may be made especially of α,ω-diol or α,ω-dicarboxylic polyalkylsiloxanes and especially α,ω-diol polydimethylsiloxanes and α,ω-dicarboxylic polydimethylsiloxanes; α,ω-diol or α,ω-dicarboxylic polyarylsiloxanes and especially α,ω-diol or α,ω-dicarboxylic polyphenylsiloxanes; polyarylsiloxanes containing silanol functions such as polyphenyl-siloxane; polyalkylsiloxanes containing silanol functions such as polydimethylsiloxane; polyaryl/alkyl-siloxanes containing silanol functions such as polyphenyl/methylsiloxane or polyphenyl/propylsiloxane.

α,ω-Diol polydimethylsiloxanes with a weight-average molecular mass (Mw) of between 400 and 10 000 or even between 500 and 5000 and especially between 800 and 4000 will be used most particularly.

When it is present, the silicone may preferably represent 0.1% to 15% by weight, especially 1% to 10% by weight or even 2% to 8% by weight relative to the weight of the polycondensate.

In one preferred embodiment of the invention, the aromatic monocarboxylic acid is present in a molar amount greater than or equal to that of the non-aromatic monocarboxylic acid; in particular, the ratio between the number of moles of aromatic monocarboxylic acid and the number of moles of non-aromatic monocarboxylic acid is preferably between 0.08 and 0.70, especially between 0.10 and 0.60 and in particular between 0.12 and 0.40.

Preferably, the polycondensate according to the invention may be obtained by reacting:
 at least one polyol chosen, alone or as a mixture, from 1,2,6-hexanetriol, trimethylolethane, trimethylolpropane, glycerol; pentaerythritol, erythritol, diglycerol, ditrimethylolpropane; xylitol, sorbitol, mannitol, dipentaerythritol and/or triglycerol;
 preferably present in an amount of 10% to 30% by weight, especially 12% to 25% by weight and better still 14% to 22% by weight, relative to the total weight of the final polycondensate;
 at least one non-aromatic monocarboxylic acid chosen, alone or as a mixture, from caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid;
 preferably present in an amount of 30% to 80% by weight, especially 40% to 75% by weight and better still 45% to 70% by weight relative to the total weight of the final polycondensate;
 at least one aromatic monocarboxylic acid chosen, alone or as a mixture, from benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid;
 preferably present in an amount of 0.1% to 10% by weight, especially 1% to 9.5% by weight and better still 1.5% to 8% by weight relative to the total weight of the final polycondensate; and
 at least one polycarboxylic acid or an anhydride thereof, chosen, alone or as a mixture, from decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid; cyclohexanetricarboxylic acid, trimellitic acid, 1,2,3-benzenetricarboxylic acid, 1,3,5-benzenetricarboxylic acid; butanetetracarboxylic acid, pyromellitic acid, phthalic anhydride, trimellitic anhydride, maleic anhydride and succinic anhydride;
 preferably present in an amount of 5% to 40% by weight, especially 10% to 30% by weight and better still 14% to 25% by weight relative to the total weight of the final polycondensate.

Preferentially, the polycondensate according to the invention may be obtained by reacting:
 at least one polyol chosen, alone or as a mixture, from glycerol, pentaerythritol and sorbitol, and mixtures thereof, and better still pentaerythritol alone; present in an amount of 10% to 30% by weight, especially 12% to 25% by weight and better still 14% to 22% by weight relative to the total weight of the final polycondensate;
 at least one non-aromatic monocarboxylic acid chosen, alone or as a mixture, from 2-ethylhexanoic acid, isooctanoic acid, lauric acid, palmitic acid and isostearic acid, and mixtures thereof, and better still isostearic acid alone; present in an amount of 30% to 80% by weight, especially 40% to 75% by weight and better still 45% to 70% by weight relative to the total weight of the final polycondensate;
 at least one aromatic monocarboxylic acid chosen, alone or as a mixture, from benzoic acid, o-toluic acid, m-toluic acid and 1-naphthoic acid, and better still benzoic acid alone; present in an amount of 0.1% to 10% by weight, especially 1% to 9.5% by weight, or even 1.5% to 8% by weight, relative to the total weight of the final polycondensate; and
 at least one polycarboxylic acid or an anhydride thereof, chosen, alone or as a mixture, from phthalic anhydride and isophthalic acid, and better still isophthalic acid alone; present in an amount of 5% to 40% by weight, especially 10% to 30% by weight and better still 14% to 25% by weight relative to the total weight of the final polycondensate.

The polycondensate according to the invention may be prepared via the esterification/polycondensation processes usually used by those skilled in the art. By way of illustration, a general preparation process consists in:
 mixing the polyol and the aromatic and non-aromatic monocarboxylic acids,
 heating the mixture under an inert atmosphere, first to the melting point (generally 100-130° C.) and then to a temperature of between 150 and 220° C. until the monocarboxylic acids have been totally consumed (achieved when the acid number is less than or equal to 1), preferably while gradually distilling off the water formed, then
 optionally cooling the mixture to a temperature of between 90 and 150° C.,
 adding the polycarboxylic acid and/or the cyclic anhydride, and optionally the silicone containing hydroxyl or carboxylic functions, in a single portion or sequentially, and then
 heating again to a temperature of less than or equal to 220° C., especially between 170 and 220° C., preferably while continuing to remove the water formed, until the required characteristics in terms of acid number, viscosity, hydroxyl number and solubility are obtained.

It is possible to add conventional esterification catalysts, for example of sulfonic acid type (especially in a weight concentration of between 1% and 10%) or of titanate type (especially in a weight concentration of between 5 and 100 ppm).

It is also possible to perform the reaction, totally or partly, in an inert solvent such as xylene and/or under reduced pressure, to facilitate the removal of the water. Advantageously, neither catalyst nor solvent is used.

The preparation process may also comprise a step of adding at least one antioxidant to the reaction medium, especially in a weight concentration of between 0.01% and 1% relative to the total weight of monomers, so as to limit the possible degradation associated with prolonged heating.

The antioxidant may be of primary type or secondary type, and may be chosen from hindered phenols, aromatic secondary amines, organophosphorus compounds, sulfur compounds, lactones and acrylic bisphenols; and mixtures thereof.

Mineral Lipophilic Structuring Agents

The fatty-phase rheological agent may be a mineral lipophilic structuring agent.

Mention may be made especially of lipophilic clays, for instance optionally modified clays, for instance hectorites modified with a $C_{10}$ to $C_{22}$ ammonium chloride, for instance hectorite modified with distearyldimethylammonium chloride.

Mention may also be made of hydrophobic silicas, for instance fumed silica optionally subjected to a hydrophobic surface treatment, the particle size of which is less than 1 µm. Specifically, it is possible to chemically modify the surface of the silica, by chemical reaction generating a reduced number of silanol groups present at the surface of the silica. It is especially possible to substitute silanol groups with hydrophobic groups: a hydrophobic silica is then obtained. The hydrophobic groups may be:

- trimethylsiloxyl groups, which are obtained especially by treating fumed silica in the presence of hexamethyldisilazane. Silicas thus treated are known as "silica silylate" according to the CTFA (86th edition, 1995). They are sold, for example, under the references Aerosil R812® by the company Degussa, and Cab-O-Sil TS-530® by the company Cabot;
- dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

Lipophilic Polyamide Polymers

For the purposes of the invention, the term "polymer" means a compound containing at least two repeating units, preferably at least three repeating units and better still 10 repeating units.

As preferred lipophilic structuring polyamide polymers that may be used in the invention, mention may be made of polyamides branched with pendent fatty chains and/or terminal fatty chains containing from 12 to 120 carbon atoms and especially from 12 to 68 carbon atoms, the terminal fatty chains being bonded to the polyamide backbone via ester groups. These polymers are more especially those disclosed in document U.S. Pat. No. 5,783,657 from the company Union Camp. Each of these polymers in particular satisfies formula (I) below:

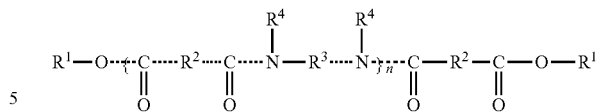

in which n denotes a whole number of amide units such that the number of ester groups represents from 10% to 50% of the total number of ester and amide groups; $R^1$ is, independently in each case, an alkyl or alkenyl group containing at least 4 carbon atoms and in particular from 4 to 24 carbon atoms; $R^2$ represents, independently in each case, a saturated or unsaturated $C_4$ to $C_{42}$ hydrocarbon-based group, on condition that 50% of the groups $R^2$ represent a saturated or unsaturated $C_{30}$ to $C_{42}$ hydrocarbon-based group; $R^3$ represents, independently in each case, an organic group containing at least 2 carbon atoms, hydrogen atoms and optionally one or more oxygen or nitrogen atoms; and $R^4$ represents, independently in each case, a hydrogen atom, a saturated or unsaturated $C_1$ to $C_{10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R^4$ representing a hydrogen atom.

In particular, the ester groups of formula (I), which form part of the terminal and/or pendent fatty chains for the purposes of the invention, represent from 15% to 40% of the total number of ester and amide groups and better still from 20% to 35%. Furthermore, n advantageously represents an integer ranging from 1 to 5. Preferably, $R^1$ is a saturated or unsaturated $C_{12}$ to $C_{22}$ and preferably $C_{16}$ to $C_{22}$ alkyl group. Advantageously, $R^2$ can be a $C_{10}$ to $C_{42}$ hydrocarbon-based (alkylene) group. Preferably, at least 50% and better still at least 75% of the groups $R^2$ are groups containing from 30 to 42 carbon atoms. The other groups $R^2$ are $C_4$ to $C_{19}$ and better still $C_4$ to $C_{12}$ hydrogen-containing groups. Preferably, $R^3$ represents a $C_2$ to $C_{36}$ hydrocarbon-based group or a polyoxyalkylene group and $R^4$ represents a hydrogen atom. Preferably, $R^3$ represents a saturated or unsaturated $C_2$ to $C_{12}$ hydrocarbon-based group. The hydrocarbon-based groups may be linear, cyclic or branched, and saturated or unsaturated groups. Moreover, the alkyl and alkylene groups may be linear or branched groups.

Advantageously, the polymer in the composition of the invention has a weight-average molecular mass ranging from 2000 to 20 000 and better still from 2000 to 10 000.

According to the invention, the structuring of the oil is obtained with the aid of one or more polymers of formula (I). In general, the polymers of formula (I) are in the form of mixtures of polymers, these mixtures also possibly containing a synthetic product such that n is 0, i.e. a diester.

As examples of structuring polymers that can be used in the composition according to the invention, mention may be made of the commercial products manufactured and/or sold by the company Bush Boake Allen under the names Uniclear 80 and Uniclear 100. They are sold, respectively, in the form of an 80% (in terms of active material) gel in a mineral oil and a 100% (in terms of active material) gel. They have a softening point of from 88 to 94° C. These commercial products are a mixture of copolymers of a $C_{36}$ diacid coupled with ethylenediamine, having a weight-average molecular mass of about 6000. The remaining acid end groups are also esterified with cetylstearyl alcohol.

As structuring polymers which can be used in the invention, mention may also be made of polyamide resins resulting from the condensation of an aliphatic dicarboxylic acid and a diamine (including compounds containing, respectively, more than 2 carboxyl groups and more than 2 amine groups), the carboxyl and amine groups of adjacent individual units being condensed in the form of an amide bond. These polyamide resins are, in particular, those sold under the brand name Versamid® by the companies General Mills, Inc. and Henkel Corp. (Versamid 930, 744 or 1655) or by the company Olin Mathieson Chemical Corp. under the brand name Onamid®, in particular Onamid S or C. These resins have a weight-average molecular mass ranging from 6000 to 9000. For further information regarding these polyamides, reference may be made to the documents U.S. Pat. No. 3,645,705 and U.S. Pat. No. 3,148,125. More especially, Versamid® 930 or 744 is used.

The polyamides sold by the company Union Camp Corp. under the references Uni-Rez (2658, 2931, 2970, 2621, 2613, 2624, 2665, 1554, 2623 and 2662) and the product sold under the reference Macromelt 6212 by the company Henkel may also be used. For further information regarding these polyamides, reference may be made to document U.S. Pat. No. 5,500,209.

The structuring polymers in the composition of the invention advantageously have a softening point of greater than 70° C., which may be up to 190° C. They preferably have a softening point ranging from 80 to 130° C. These polymers are, in particular, non-waxy polymers.

Lipophilic Polyurea or Polyurethane Polymers

As fatty-phase rheological agents, mention may also be made of polyurethanes and polyureas that are soluble or dispersible in hydrocarbon-based oil(s), and comprising:
  at least two urethane groups, at least two urea groups, or at least one urethane group and one urea group in the chain,
  at least one hydrocarbon-based long-chain, preferably branched, aliphatic polyester or hydrocarbon-based block or graft.

The expression "hydrocarbon-based long chain" means a linear or branched hydrocarbon-based chain containing at least 8 carbon atoms and preferably 10 to 500 carbon atoms.

The polymers that are preferred according to the invention are defined by one of the following three formulae:

2) a graft

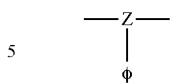

in which Z is a hydrocarbon-based trivalent radical which may contain one or more heteroatoms, and φ is a linear, branched or cyclic aliphatic chain, or 3) mixtures of the blocks 1) and grafts 2).

The monovalent hydrocarbon-based radicals $A_1$ and $A_2$ are preferably chosen from saturated or unsaturated, aliphatic, cycloaliphatic and aromatic radicals. The radicals $A_1$ and $A_2$ are obtained from monoalcohols and/or monoamines optionally used to consume the isocyanate groups that are residual at the end of polymerization.

When D is a saturated or unsaturated, aliphatic and/or cycloaliphatic hydrocarbon-based block, it is obtained:
  from a natural or synthetic oil,
  from the product of addition (dimer, trimer or polymer) of at least two unsaturated aliphatic chains, such as aliphatic radicals derived from "dimeric" fatty acids, such as, for example, the products of addition between oleic chains, or
  from polyenes, which are preferably hydrogenated, such as polybutadiene, hydrogenated polyisoprene, or polyolefins or copolyolefins.

When D is a hydrocarbon-based long-chain aliphatic polyester block, it is preferably obtained from hydrocarbon-based long-chain branched polyesters such as, for example, poly(12-hydroxystearate).

When D is a graft, φ is a saturated or unsaturated, linear, branched or cyclic aliphatic chain containing from 8 to 40 carbon atoms. The optional heteroatoms in the trivalent radical Z are preferably —O—, —N— and —S—.

The structuring polyurethanes and/or polyureas according to the invention result from the polymerization reaction between:

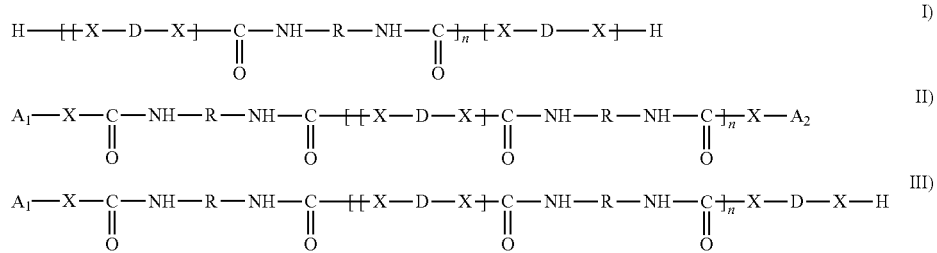

in which:
n denotes an integer from 1 to 10,000 and preferably from 1 to 1000,
X represents, separately or in combination, —O— or —NH—, R is a divalent radical chosen from alkylene, cycloalkylene and aromatic radicals, and mixtures thereof, which are optionally functionalized,
$A_1$ and $A_2$, which may be identical or different, denote linear, branched or cyclic monovalent hydrocarbon-based radicals, which are saturated or which may contain unsaturations, containing from 1 to 80 carbon atoms,
D is
1) a saturated or unsaturated, aliphatic and/or cycloaliphatic hydrocarbon-based divalent block, and/or a hydrocarbon-based long-chain aliphatic polyester, 1) at least one aliphatic, cycloaliphatic and/or aromatic diisocyanate of general formula O═C═N—R—N═C═O, in which R is as defined above,
2) at least one difunctional derivative HX-D-XH, having two active hydrogens which can each react with an isocyanate group, in which
  X denotes —O— or —NH—, and
  D is as defined above, and
3) optionally, a monofunctional derivative $A_1$-XH, or two monofunctional derivatives $A_1$-XH and $A_2$-XH, having only one active hydrogen which can react with an isocyanate group, to consume the residual isocyanate groups that have not fully reacted with the difunctional reagents H—X-D-X—

H, the monofunctional derivatives A$_1$-XH and A$_2$-XH possibly being identical or different, and A$_1$ and A$_2$ being as defined above.

The isocyanates used in the polymerization reaction may be aliphatic, cycloaliphatic or aromatic. Hexamethylene diisocyanate, isophorone diisocyanate, toluene diisocyanate or 4,4'-dicyclohexylmethane diisocyanate will be advantageously used.

The difunctional derivatives H—X-D-X—H may be chosen from diol dimers and derivatives thereof, alkanediols, polydienes with hydroxyl ends, which are preferably hydrogenated, polyolefins with hydroxyl ends, long-alkyl-chain branched polyesters bearing at least two reactive groups, natural or synthetic oils bearing two or three hydroxyl groups, and finally long-aliphatic-chain diamines and diamine dimers.

The diol dimers are branched C$_{36}$ aliphatic and/or alicyclic diols, and/or a mixture of the dimers. These diols are prepared from the "corresponding dimeric fatty acids".

The expression "corresponding dimeric fatty acids" means dimeric fatty acids which have the same structure as these diols, but which have two carboxylic acid ends instead of diol ends. The conversion of the dimeric fatty acids into diol dimers may be carried out either by hydrogenation of methyl esters of the dimeric fatty acids or by direct dimerization of oleyl alcohol. Mention will be made in particular of the diol dimers sold by the company Cognis under the trade names Sovermol 908 (at 97% purity) and Sovermol 650 NS (at 68% purity).

It is also possible to use polyether diol oligomers and polycarbonate diol oligomers, prepared by subsequent etherification or esterification of these same branched C$_{36}$ diol dimers. These oligomers generally have a number-average molecular mass in the region of from 500 to 2000, and contain two hydroxyl functions.

The polydienes with hydroxyl ends are, for example, those defined in French patent FR-2 782 723. They are chosen from the group comprising the homopolymers and copolymers of polybutadiene, of polyisoprene and of poly(1,3-pentadiene). These oligomers have a number-average molecular mass of less than 7000 and preferably from 1000 to 5000. They have a chain-end functionality of from 1.8 to 3 and preferably in the region of 2. These polydienes with hydroxyl ends are, for example, the hydroxylated polybutadienes sold by the company Elf Atochem under the brand names Poly BD-45H® and Poly BD R-20 LM®. These products are preferably used hydrogenated.

It is also possible to use polyolefin homopolymers or copolymers with α,ω-hydroxyl ends, such as, for example:
polyisobutylene oligomers with α,ω-hydroxyl ends, or
the copolymers sold by the company Mitsubishi under the brand name Polytail®, in particular those of structure:

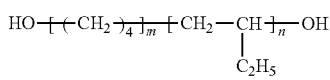

with a melting point of 60 to 70° C.

It is possible to use as difunctional derivative H—X-D-X—H, a long-alkyl-chain branched polyester comprising at least two reactive groups, such as, for example, poly(12-hydroxystearate) containing hydroxyl ends. This polyester is obtained by self-condensation of 1,2-hydroxystearic acid, followed by reaction with a polyol to consume the residual acid groups. This oligomer of structure

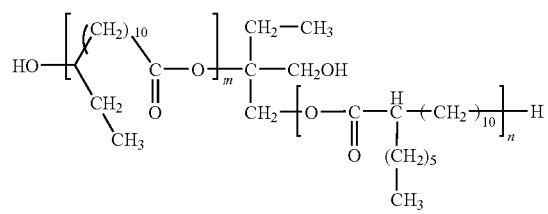

in which the sum m+n is such that the oligomer has a number-average molecular mass in the region of 2000 and a hydroxyl functionality in the region of 1.8.

Natural or synthetic oils bearing 2 or 3 hydroxyl groups may also be used as difunctional derivative H—X-D-X—H.

In one particular embodiment of the invention, the oils used will be those bearing two hydroxyl groups per chain, and preferably the monoglycerides of structure:

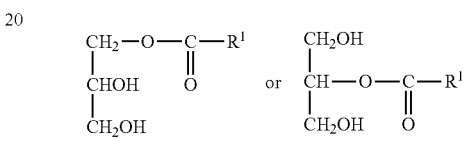

R$^1$ being a linear or branched C$_8$ to C$_{30}$ alkyl chain such as, for example, glyceryl monostearate.

Such glyceryl monostearates correspond, for example, to the difunctional derivatives H—X-D-X—H, in which:
D represents

X represents —O—, and

represents

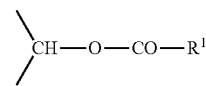

in which R$^1$ is defined as above.

When these glycerol monoesters are reacted with a diisocyanate, a solubilizing graft is introduced into the polymer chain rather than a block, as was the case with the difunctional derivatives mentioned above.

In one variant, a difunctional derivative H—X-D-X—H chosen from oils bearing three hydroxyl groups per chain, such as, for example, hydrogenated or non-hydrogenated castor oil, will be used.

In this case, the polymerization reaction is carried out with a deficit of diisocyanate relative to the reaction stoichiometry, to avoid the crosslinking of the polymer and to conserve good solubility thereof.

Long-aliphatic-chain diols may also be used. Advantageously, diols of structure HO-D-OH in which D is a linear or branched alkyl chain containing from 8 to 40 carbon atoms will be used. These diols are sold by the company Atochem under the name Vikinol®. Mention will also be made of 1,12-dodecanediol and 1,10-decanediol, the latter being sold by the company Cognis under the trade name Sovermol 110®.

It is also possible to use diols of structure

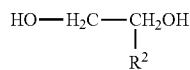

in which $R^2$ is an alkyl chain containing from 8 to 40 carbon atoms.

These long-aliphatic-chain diols are preferably used with any one of the H—X-D-X—H derivatives mentioned above, to serve as chain couplers during the synthesis of polyurethanes and/or polyureas.

Finally, long-aliphatic-chain diamines or diamine dimers may be used as difunctional derivative H—X-D-X—H.

The use of such reagents in the polymerization reaction makes it possible to introduce into the polymer urea groups rather than urethane groups.

According to one particular embodiment of the invention, diamine dimers having the same structure as the diol dimers mentioned above will be used, that is to say diamine dimers comprising two primary amine functions instead of hydroxyl groups.

These diamine dimers may be obtained from the conversion of dimeric fatty acids, like the diol dimers.

In one variant, diamines of structure $H_2N$-D-$NH_2$ in which D is a linear or branched alkyl chain containing from 8 to 40 carbon atoms may be used. These diamines are preferably used as a mixture with a difunctional derivative H—X-D-X—H chosen from diol dimers and derivatives thereof, polydienes and polyolefins with hydroxyl ends, long-alkyl-chain branched polyesters, and oils bearing 2 or 3 hydroxyl groups, mentioned above.

Among these diamines, mention may be made of:
1,10-diaminodecane and 1,12-diaminododecane, and
the following diamino oils sold by the company Akzo Nobel: cocopropylene diamine (distilled or undistilled) Duomeen® C or CD, hydrogenated tallowpropylene diamine Duomeen® HT, $C_{16-22}$ alkylpropylene diamine Duomeen® M, oleylpropylene diamine Duomeen® O, tallowpropylene diamine Duomeen® T.

As regards the monofunctional derivatives $A_1$-XH and $A_2$-XH, they are advantageously chosen from monoalcohols and monoamines with linear or branched alkyl chains containing from 1 to 80 carbon atoms, natural or synthetic oils bearing a single hydroxyl group per chain, such as, for example, glycerol diesters or citric acid triesters of a fatty alcohol.

The polycondensation reactions envisaged are conventionally carried out in an organic solvent capable of dissolving the reagents and the polymer formed. This solvent is preferably readily removable at the end of the reaction, in particular by distillation, and does not react with the isocyanate groups.

Generally, each of the reagents is dissolved in some of the organic solvent before the polymerization reaction.

It is occasionally desired to use a catalyst to activate the polymerization. This catalyst will generally be chosen from the catalysts commonly used in polyurethane and polyurea chemistry, such as, for example, tin 2-ethylhexanoate.

The molar proportion between the main reagents of the polymerization reaction depends on the chemical structure and on the molecular weight of the polymers (polyurethanes and/or polyureas) which it is desired to obtain, as is conventionally the case in polyurethane and polyurea chemistry. Similarly, the order of introduction of the reagents will be adapted to this chemistry.

Thus, the reaction of two moles of functional derivative H—X-D-X—H with one mole of diisocyanate gives, after total consumption of the reagents, a polymer defined by formula I:

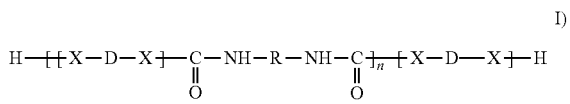

For this reaction, the process will advantageously be performed in the following manner:
the initial medium is a solution comprising two moles of derivative H—X-D-X—H, for example two moles of diol dimer, in a solvent, for example tetrahydrofuran,
a solution comprising one mole of diisocyanate dissolved in the same solvent, such as, for example, toluene diisocyanate dissolved in tetrahydrofuran, is added dropwise to this initial solution.

Moreover, the equimolar reaction of a difunctional derivative H—X-D-X—H with a diisocyanate, with consumption of the residual isocyanates by a monofunctional compound $A_1$-XH, gives a polymer defined by formula III:

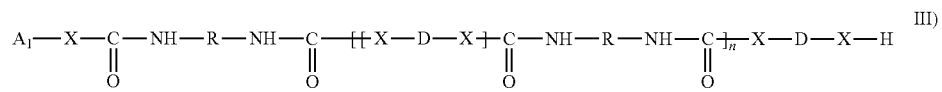

This reaction will then preferably be carried out by simultaneous addition, into a reactor, of an organic solution of one mole of H—X-D-X—H, such as, for example, a Polytail® described above, and of an organic solution of one mole of diisocyanate, such as, for example, 4,4'-dicyclohexylmethane diisocyanate. The simultaneous addition of these two organic solutions is also known as "double addition". At the end of the double addition, the reaction mixture is heated at 60° C. for 5 hours. A sample of the reaction medium is then taken to assay the residual isocyanates using a method known to those skilled in the art. Finally, a solution of a chosen monofunctional compound $A_1$-X—H is added to the reaction medium, in an amount which is sufficient to consume the residual isocyanates, this amount having been estimated from the assay of the residual isocyanates. 1-Decanol will advantageously be used as monofunctional derivative $A_1$-X—H.

Finally, the reaction between
one mole of compound H—X-D-X—H, such as, for example, a diol dimer,
three moles of diisocyanate such as, for example, 4,4'-dicyclohexylmethane diisocyanate, and
two moles of coupler of structure

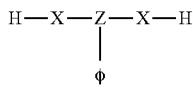

in which φ is a linear, branched or cyclic aliphatic chain containing from 8 to 20 carbon atoms, leads to the formation of a polymer which is both blocked and grafted, of structure:

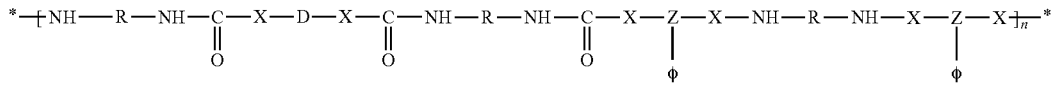

Any residual isocyanates may be consumed by adding a suitable amount of monofunctional reagent $A_1$-X—H.

To obtain such a polymer, the process is performed in the following manner:

the initial reaction medium consists of a solution comprising one mole of a difunctional derivative H—X-D-X—H, a solution of three moles of diisocyanate is added dropwise to this medium, the mixture is then left to react for 3 hours at 60° C., next, an organic solution comprising two moles of a coupler defined by the formula:

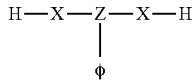

is added to this medium, any residual isocyanates possibly being consumed by adding a suitable amount of monofunctional reagent $A_1$-XH.

Lipophilic Silicone Polymers

The silicone polymeric lipophilic structuring agents are, for example, polymers of the polyorganosiloxane type, for instance those described in documents U.S. Pat. No. 5,874,069, U.S. Pat. No. 5,919,441, U.S. Pat. No. 6,051,216 and U.S. Pat. No. 5,981,680. According to the invention, the polymers used as structuring agent may belong to the following two families:

1) polyorganosiloxanes comprising at least two groups capable of establishing hydrogen interactions, these two groups being located in the polymer chain, and/or 2) polyorganosiloxanes comprising at least two groups capable of establishing hydrogen interactions, these two groups being located on grafts or branches.

The groups capable of establishing hydrogen interactions may be chosen from ester, amide, sulfonamide, carbamate, thiocarbamate, urea, urethane, thiourea, oxamido, guanidino and biguanidino groups, and combinations thereof.

According to a first variant, the silicone polymers are polyorganosiloxanes as defined above in which the units capable of establishing hydrogen interactions are located in the polymer chain.

The silicone polymers may be more particularly polymers comprising at least one unit corresponding to the general formula I:

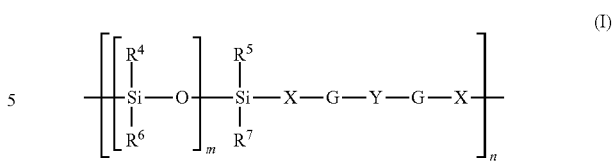

in which:

1) $R^4$, $R^5$, $R^6$ and $R^7$, which may be identical or different, represent a group chosen from:

linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulfur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulfur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups; or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_1$ to $C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

5) the groups G, which may be identical or different, represent divalent groups chosen from:

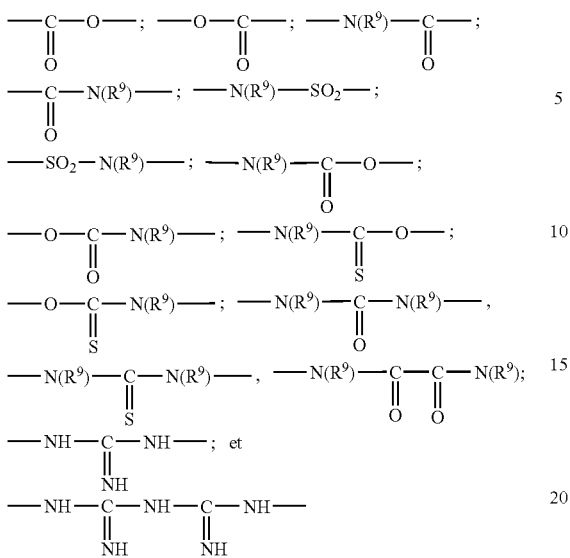

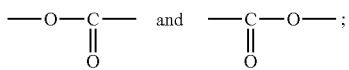

in which $R^9$ represents a hydrogen atom or a linear or branched $C_1$ to $C_{20}$ alkyl group, on condition that at least 50% of the groups $R^9$ of the polymer represent a hydrogen atom and that at least two of the groups G of the polymer are a group other than:

—O—C(=O)— and —C(=O)—O—;

6) n is an integer ranging from 2 to 500 and preferably from 2 to 200, and m is an integer ranging from 1 to 1000, preferably from 1 to 700 and better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other units of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

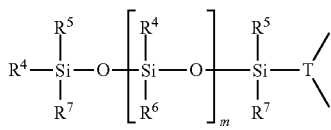

in which $R^4$, $R^5$, $R^6$, $R^7$, T and m are as defined above, and h) polyorganosiloxane chains of formula:

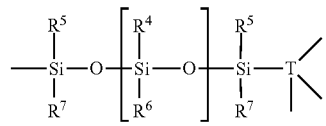

According to the second variant, the polyorganosiloxanes may be polymers comprising at least one unit corresponding to formula (II):

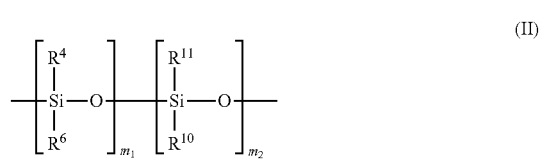

(II)

in which $R^4$ and $R^6$, which may be identical or different, are as defined above for formula (I), $R^{10}$ represents a group as defined above for $R^4$ and $R^6$, or represents a group of formula —X-G-$R^{12}$ in which X and G are as defined above for formula (I) and $R^{12}$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^{11}$ represents a group of formula —X-G-$R^{12}$ in which X, G and $R^{12}$ are as defined above, $m_1$ is an integer ranging from 1 to 998, and $m_2$ is an integer ranging from 2 to 500.

According to the invention, the silicone polymer used as structuring agent may be a homopolymer, that is to say a polymer comprising several identical units, in particular units of formula (I) or of formula (II).

According to the invention, it is also possible to use a silicone polymer formed from a copolymer comprising several different units of formula (I), that is to say a polymer in which at least one of the groups $R^4$, $R^5$, $R^6$, $R^7$, X, G, Y, m and n is different in one of the units. The copolymer may also be formed from several units of formula (II), in which at least one of the groups $R^4$, $R^6$, $R^{10}$, $R^{11}$, $m_1$ and $m_2$ is different in at least one of the units.

It is also possible to use a polymer comprising at least one unit of formula (I) and at least one unit of formula (II), the units of formula (I) and the units of formula (II) possibly being identical to or different from each other.

According to one variant of the invention, it is also possible to use a polymer furthermore comprising at least one hydrocarbon-based unit comprising two groups capable of establishing hydrogen interactions, chosen from ester, amide, sulfonamide, carbamate, thiocarbamate, urea, urethane, thiourea, oxamido, guanidino and biguanidino groups, and combinations thereof.

These copolymers may be block polymers or grafted polymers.

According to a first advantageous embodiment of the invention, the groups capable of establishing hydrogen interactions are amide groups of formulae —C(O)NH— and —HN—C(O)—. In this case, the structuring agent may be a polymer comprising at least one unit of formula (III) or (IV):

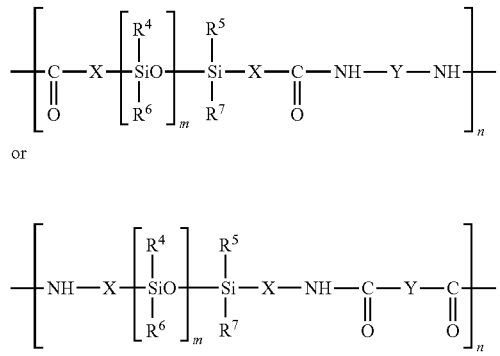

(III)

or

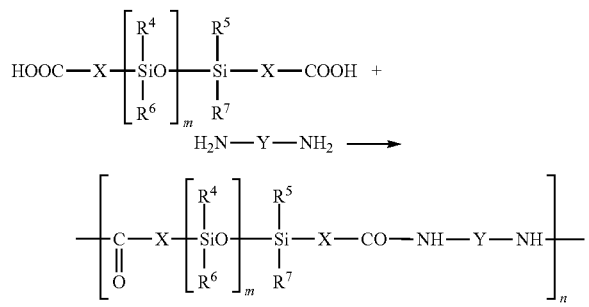

(IV)

in which $R^4$, $R^5$, $R^6$, $R^7$, X, Y, m and n are as defined above.

Such a unit may be obtained:
either by a condensation reaction between a silicone containing α,ω-carboxylic acid ends and one or more diamines, according to the following reaction scheme:

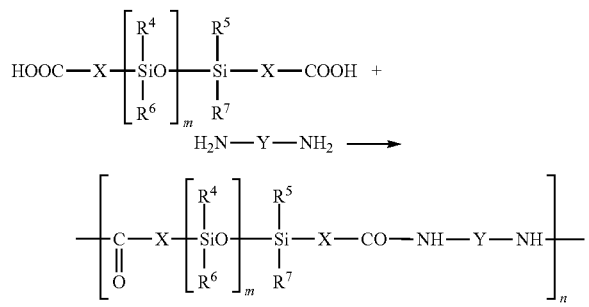

or by reaction of two molecules of α-unsaturated carboxylic acid with a diamine according to the following reaction scheme:

CH$_2$=CH—X$^1$—COOH+H$_2$N—Y—NH$_2$→CH$_2$=CH—X$^1$—CO—NH—Y—NH—CO—X$^1$—CH=CH$_2$ followed by the addition of a siloxane to the ethylenic unsaturations, according to the following scheme:

CH$_2$=CH—X$^1$—CO—NH—Y—NH—CO—X$^1$—CH=CH$_2$ +

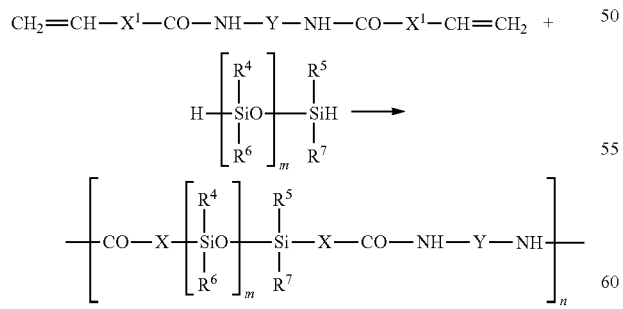

in which X$^1$—(CH$_2$)$_2$— corresponds to X defined above and Y, $R^4$, $R^5$, $R^6$, $R^7$ and m are as defined above;
or by reaction of a silicone containing α,ω-NH$_2$ ends and a diacid of formula HOOC—Y—COOH according to the following reaction scheme:

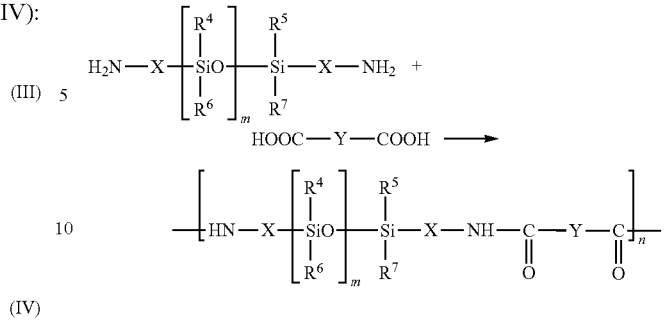

In these polyamides of formula (III) or (IV), m is in the range from 1 to 700, in particular from 15 to 500 and especially from 50 to 200, and n is in particular in the range from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following members:
1) 1 to 5 amide, urea, urethane or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one member chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^8$ represents a polyorganosiloxane chain and T represents a group of formula:

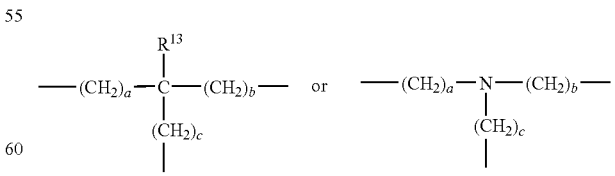

in which a, b and c are, independently, integers ranging from 1 to 10, and $R^{13}$ is a hydrogen atom or a group such as those defined for $R^4$, $R^5$, $R^6$ and $R^7$.

In formulae (III) and (IV), $R^4$, $R^5$, $R^6$ and $R^7$ preferably represent, independently, a linear or branched $C_1$ to $C_{40}$ alkyl group, preferably a $CH_3$, $C_2H_5$, $n-C_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Thus, the polymer may be a polyamide containing several units of formula (III) or (IV) of different lengths, i.e. a polyamide corresponding to formula (V):

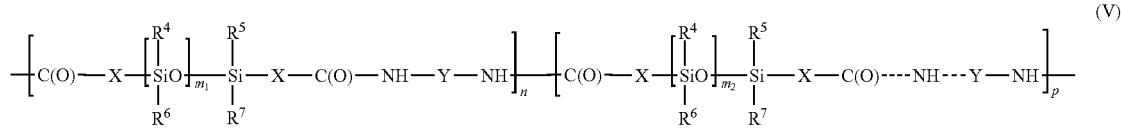

(V)

in which X, Y, n and $R^4$ to $R^7$ have the meanings given above, $m_1$ and $m_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula VI:

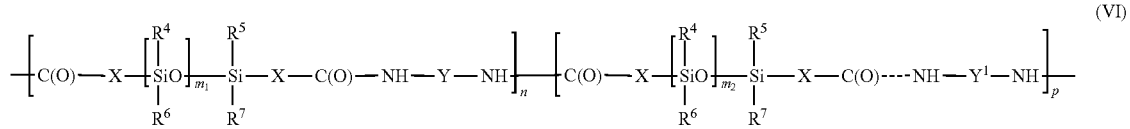

(VI)

in which $R^4$ to $R^7$, X, Y, $m_1$, $m_2$, n and p have the meanings given above and $Y^1$ is different from Y but chosen from the groups defined for Y. As previously, the various units may be structured to form either a block copolymer, or a random copolymer or an alternating copolymer.

In this first embodiment of the invention, the structuring agent may also consist of a grafted copolymer. Thus, the polyamide containing silicone units may be grafted and optionally crosslinked with silicone chains containing amide groups. Such polymers may be synthesized with trifunctional amines.

In this case, the polymer may comprise at least one unit of formula (VII):

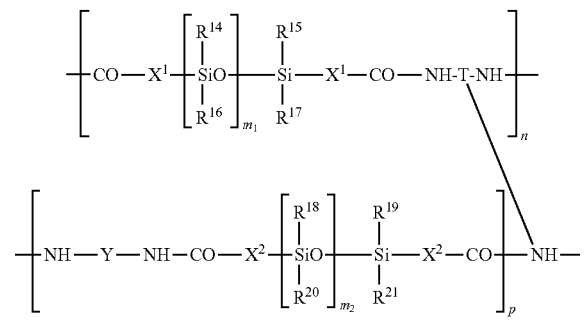

(VII)

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as $R^4$ to $R^7$, $m_1$ and $m_2$ are numbers in the range from 1 to 1000, and p is an integer ranging from 2 to 500.

In formula (VII), it is preferred that:
p is in the range from 1 to 25 and better still from 1 to 7,
$R^{14}$ to $R^{21}$ are methyl groups,
T corresponds to one of the following formulae:

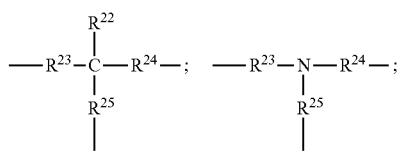

-continued

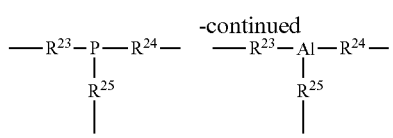

in which $R^{22}$ is a hydrogen atom or a group chosen from the groups defined for $R^4$ to $R^7$, and $R^{23}$, $R^{24}$ and $R^{25}$ are, independently, linear or branched alkylene groups, and more preferably correspond to the formula:

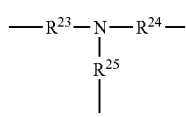

in particular with $R^{23}$, $R^{24}$ and $R^{25}$ representing —$CH_2$— $CH_2$—,
$m_1$ and $m_2$ are in the range from 15 to 500 and better still from 15 to 45,
$X^1$ and $X^2$ represent —$(CH_2)_{10}$—, and
Y represents —$CH_2$—.

These polyamides containing a grafted silicone unit of formula (VII) may be copolymerized with polyamide-silicones of formula (II) to form block copolymers, alternating copolymers or random copolymers. The weight percentage of grafted silicone units (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (III) or (IV) and hydrocarbon-based polyamide units, may be used. In this case, the polyamide-silicone units may be located at the ends of the hydrocarbon-based polyamide.

Advantageously, the composition according to the invention comprises at least one polydimethylsiloxane block polymer of general formula (I) with an m value of about 15.

More preferably, the composition according to the invention comprises at least one polymer comprising at least one unit of formula (III) in which m ranges from 5 to 100, in particular from 10 to 75 and is more particularly about 15; preferably also, $R^4$, $R^5$, $R^6$ and $R^7$ independently represent, in formula (III), a linear or branched $C_1$-$C_{40}$ alkyl group, preferably a $CH_3$, $C_2H_5$, n-$C_3H_7$ or isopropyl group.

As examples of silicone polymers that may be used, mention may be made of one of the silicone polyamides obtained in accordance with Examples 1 to 3 of document U.S. Pat. No. 5,981,680.

According to one embodiment variant of the invention, the polymer consists of a homopolymer or copolymer comprising urethane or urea groups. These polymers are described in detail in patent application WO 2003/106 614 published on Dec. 24, 2003, the content of which is incorporated into the present patent application by reference.

As previously, such a polymer may comprise polyorganosiloxane units containing two or more urethane and/or urea groups, either in the backbone of the polymer or on side chains or as pendent groups. The polymers comprising at least two urethane and/or urea groups in the backbone may be polymers comprising at least one unit corresponding to the following formula (VIII):

$$\left[\begin{array}{c} R^4 \\ | \\ -Si-O \\ | \\ R^6 \end{array}\right]_m \begin{array}{c} R^5 \\ | \\ Si-X-U-C-NH-Y-NH-C-U-X \\ | \quad\quad\quad \| \quad\quad\quad\quad\quad\quad\quad \| \\ R^7 \quad\quad\quad O \quad\quad\quad\quad\quad\quad\quad O \end{array}\Big]_n \quad (VIII)$$

in which $R^4$, $R^5$, $R^6$, $R^7$, X, Y, m and n have the meanings given above for formula (I), and U represents —O— or —NH—, such that:

$$-U-C-NH-$$
$$\quad\;\|$$
$$\quad\;O$$

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4'-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to formula (IX):

$$-\left[B^1-NH-\underset{\underset{O}{\|}}{C}-U-B^2-U-\underset{\underset{O}{\|}}{C}-NH\right]_d B^1-\quad (IX)$$

in which $B^1$ is a group chosen from the groups given above for Y, U is —O— or —NH— and $B^2$ is chosen from:

linear or branched $C_1$ to $C_{40}$ alkylene groups, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

$$R^8-T\diagdown$$

in which T is a hydrocarbon-based trivalent radical possibly containing one or more heteroatoms such as oxygen, sulfur and nitrogen and $R^8$ is a polyorganosiloxane chain or a linear or branched $C_1$ to $C_{50}$ alkyl chain.

T can represent, for example:

$$-(CH_2)_w-CH-CH_2- \quad \text{or}$$
$$\quad\quad\quad\quad\quad |$$

$$-(CH_2)_w-O-CH-CH_2-$$
$$\quad\quad\quad\quad\quad\quad\quad |$$

with w being an integer ranging from 1 to 10 and $R^8$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or a group:

$$\diagdown_{T-R^8}$$
$$\diagup$$

with $R^8$ being a polyorganosiloxane chain.

As previously, the silicone polymer may be formed from silicone urethane and/or silicone urea units of different length and/or constitution, and may be in the form of block or random copolymers.

The polymers of formula (VIII) comprising urea or urethane groups in the chain of the silicone polymer may be obtained by reaction between a silicone containing α,ω-NH$_2$ or —OH end groups, of formula:

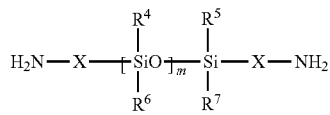

in which m, $R^4$, $R^5$, $R^6$, $R^7$ and X are as defined for formula (I), and a diisocyanate OCN—Y—NCO in which Y has the meaning given in formula (I); and optionally a diol or diamine coupling agent of formula H$_2$N—B$^2$—NH$_2$ or HO—B$^2$—OH, in which B$^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (IV), (II) or (III), it is possible to use in the invention polyurethane or polyurea silicones containing units of different length and structure, in particular units whose lengths differ by the number of silicone units. In this case, the copolymer may correspond, for example, to the formula:

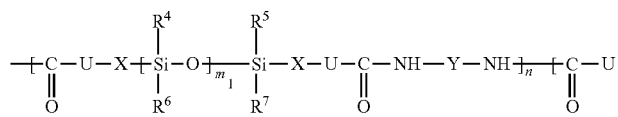

in which $R^4$, $R^5$, $R^6$, $R^7$, X, Y and U are as defined for formula (VIII) and $m_1$, $m_2$, n and p are as defined for formula (V).

According to the invention, the silicone may also comprise urethane and/or urea groups no longer in the backbone but as side branches.

In this case, the polymer may comprise at least one unit of formula:

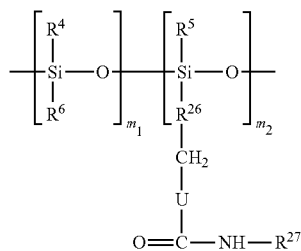

in which $R^4$, $R^6$, $R^5$, $m_1$ and $m_2$ have the meanings given above for formula (II), and $R^5$ for formula (I), U represents O or NH, $R^{26}$ represents a C$_1$ to C$_{40}$ alkylene group, optionally comprising one or more heteroatoms chosen from O and N, or a phenylene group, and $R^{27}$ is chosen from linear, branched or cyclic, saturated or unsaturated C$_1$ to C$_{50}$ alkyl groups, and phenyl groups optionally substituted with one to three C$_1$ to C$_3$ alkyl groups.

The polymers comprising at least one unit of formula (X) contain siloxane units and urea or urethane groups, and they may be used as structuring polymer in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups per branch, by reacting these polysiloxanes with monoisocyanates.

As examples of starting polymers of this type containing amino and diamino branches, mention may be made of the polymers corresponding to the following formulae:

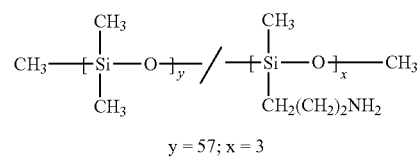

y = 57; x = 3

-continued

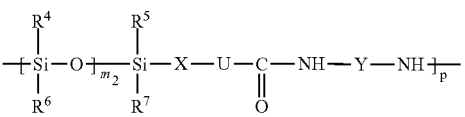

y = 56; x = 4

In these formulae, the symbol " / " indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

(XIII)

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

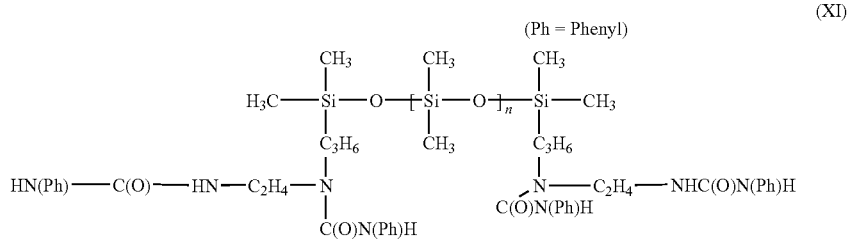

(XI)

in which Ph is a phenyl group and n is a number from 0 to 300 and in particular from 0 to 100, for example 50.

This polymer is obtained by reacting the following polysiloxane containing amino groups:

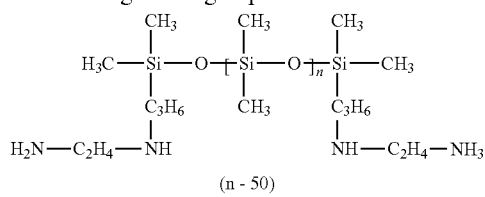

with phenyl isocyanate.

Branched polyurethane or polyurea silicones may also be obtained by using, instead of the diisocyanate OCN—Y—NCO, a triisocyanate of formula:

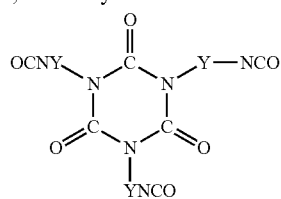

A polyurethane or polyurea silicone containing branches comprising an organosiloxane chain with groups capable of establishing hydrogen interactions is thus obtained. Such a polymer comprises, for example, a unit corresponding to the formula:

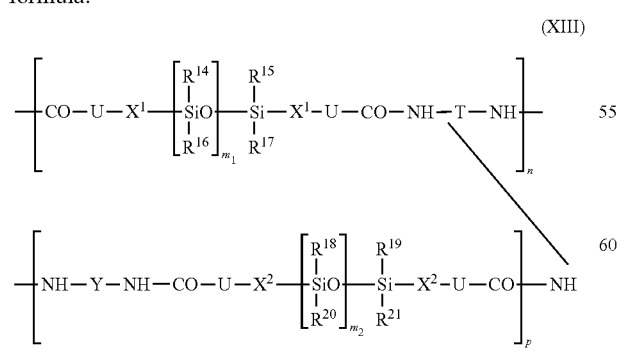

(XIII)

in which $X^1$ and $X^2$, which are identical or different, have the meaning given for X in formula (I), n is as defined in formula (I), Y and T are as defined in formula (I), $R^{14}$ to $R^{21}$ are groups chosen from the same group as $R^4$ to $R^7$, $m_1$ and $m_2$ are numbers in the range from 1 to 1000, and p is an integer ranging from 2 to 500.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, the copolymers of the invention may contain siloxane units in the main chain of the polymer and groups capable of establishing hydrogen interactions, either in the main chain of the polymer or at the ends thereof, or on side chains or branches of the main chain. This may correspond to the following five arrangements:

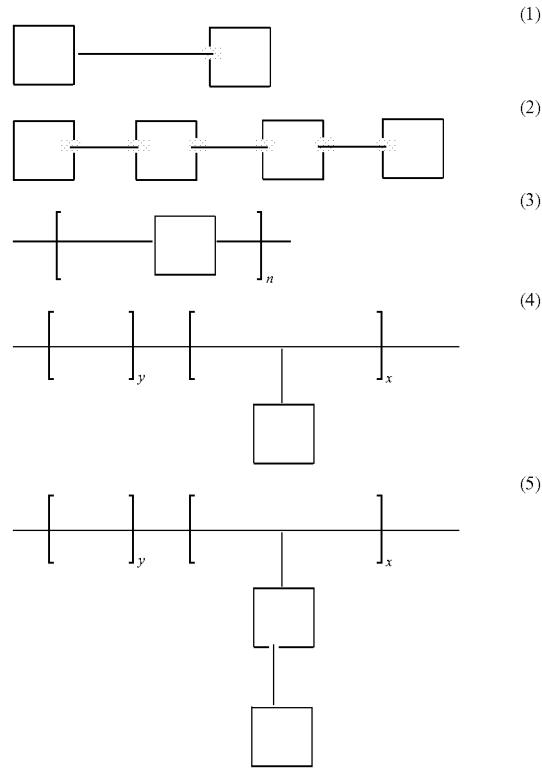

in which the continuous line is the main chain of the siloxane polymer and the squares represent the groups capable of establishing hydrogen interactions.

In case (1), the groups capable of establishing hydrogen interactions are located at the ends of the main chain. In case (2), two groups capable of establishing hydrogen interactions are located at each of the ends of the main chain.

In case (3), the groups capable of establishing hydrogen interactions are located within the main chain in repeating units.

In cases (4) and (5), these are copolymers in which the groups capable of establishing hydrogen interactions are located on branches of the main chain of a first series of units that are copolymerized with units not comprising groups capable of establishing hydrogen interactions.

The polymers and copolymers used in the composition of the invention advantageously have a transition temperature from the solid state to the liquid state ranging from 45° C. to 190° C. They preferably have a transition temperature from the solid state to the liquid state ranging from 70 to 130° C. and better still from 80° C. to 105° C.

Organogelling Agents

The oily structuring agent may also be chosen from non-polymeric molecular organic gelling agents, also known as organogelling agents, which are compounds whose molecules are capable of establishing between themselves physical interactions leading to self-aggregation of the molecules with formation of a supramolecular 3D network that is responsible for the gelation of the oil(s) (also known as the liquid fatty phase).

The supramolecular network may result from the formation of a network of fibrils (caused by the stacking or aggregation of organogelling molecules), which immobilizes the molecules of the liquid fatty phase.

The ability to form this network of fibrils, and thus to gel, depends on the nature (or chemical class) of the organogelling agent, on the nature of the substituents borne by its molecules for a given chemical class, and on the nature of the liquid fatty phase.

The physical interactions are of diverse nature but exclude co-crystallization. These physical interactions are in particular interactions of self-complementary hydrogen interaction type, π interactions between unsaturated rings, dipolar interactions, coordination bonds with organometallic derivatives, and combinations thereof. In general, each molecule of an organogelling agent can establish several types of physical interaction with a neighbouring molecule. Thus, advantageously, the molecules of the organogelling agents according to the invention comprise at least one group capable of establishing hydrogen bonds and better still at least two groups, at least one aromatic ring and better still at least two aromatic rings, at least one or more ethylenically unsaturated bonds and/or at least one or more asymmetric carbons. Preferably, the groups capable of forming hydrogen bonds are chosen from hydroxyl, carbonyl, amine, carboxylic acid, amide, urea and benzyl groups, and combinations thereof.

The organogelling agent(s) according to the invention is (are) soluble in the liquid fatty phase after heating to obtain a transparent uniform liquid phase. They may be solid or liquid at room temperature and atmospheric pressure.

The molecular organogelling agent(s) that may be used in the composition according to the invention is (are) especially those described in the document "Specialist Surfactants" edited by D. Robb, 1997, pp. 209-263, Chapter 8 by P. Terech, European patent applications EP-A-1 068 854 and EP-A-1 086 945, or alternatively in patent application WO-A-02/47031.

Mention may be made especially, among these organogelling agents, of amides of carboxylic acids, in particular of tricarboxylic acids, for instance cyclohexanetricarboxamides (see European patent application EP-A-1 068 854), diamides with hydrocarbon-based chains each containing from 1 to 22 carbon atoms, for example from 6 to 18 carbon atoms, the chains being unsubstituted or substituted with at least one substituent chosen from ester, urea and fluoro groups (see patent application EP-A-1 086 945) and especially diamides resulting from the reaction of diaminocyclohexane, in particular diaminocyclohexane in trans form, and of an acid chloride, for instance N,N'-bis-(dodecanoyl)-1,2-diaminocyclohexane, N-acylamino acid amides, for instance the diamides resulting from the action of an N-acylamino acid with amines containing from 1 to 22 carbon atoms, for instance those described in document WO-93/23008 and especially N-acylglutamic acid amides in which the acyl group represents a $C_8$ to $C_{22}$ alkyl chain, such as N-lauroyl-L-glutamic acid dibutylamide, manufactured or sold by the company Ajinomoto under the name GP-1, and mixtures thereof.

It is also possible to use, as organogelling agents, compounds of bis-urea type having the following general formula:

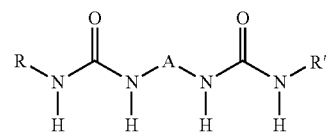

(1)

in which:

A is a group of formula (II):

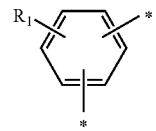

with $R_1$ being a linear or branched $C_1$-$C_4$ alkyl radical, and the *s symbolizing the points of attachment of the group A to each of the two nitrogen atoms of the rest of the compound of general formula (I), and R and R', which may be identical or different, are chosen from:

i) the radicals of formula (III):

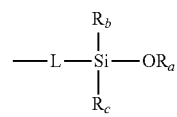

(III)

in which:

L is a single bond or a divalent carbon-based radical, especially a linear, branched and/or cyclic, saturated or unsaturated hydrocarbon-based radical (alkylene), containing 1 to 18 carbon atoms, and possibly comprising 1 to 4 heteroatoms chosen from N, O and S;

$R_a$ is:

a) a carbon-based radical, especially a linear, branched and/or cyclic, saturated or unsaturated hydrocarbon-based radical (alkyl), containing 1 to 18 carbon atoms, and possibly comprising 1 to 8 heteroatoms chosen from N, O, Si and S; or b) a silicone radical of formula:

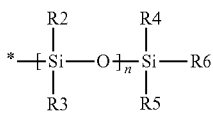

with n being between 0 and 100, especially between 1 and 80, or even 2 to 20;
and $R_2$ to $R_6$ being, independently of each other, carbon-based radicals, especially linear or branched hydrocarbon-based radicals (alkyl) containing 1 to 12 and especially 1 to 6 carbon atoms, and possibly comprising 1 to 4 heteroatoms, especially O;

$R_b$ and $R_c$ are, independently of each other, chosen from:
a) carbon-based radicals, especially linear, branched and/or cyclic, saturated or unsaturated hydrocarbon-based radicals (alkyl), containing 1 to 18 carbon atoms, and possibly comprising 1 to 4 heteroatoms chosen from N, O, Si and S;
b) the radicals of formula:

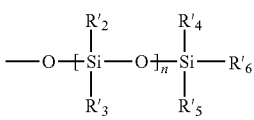

with n being between 0 and 100, especially between 1 and 80, or even 2 to 20;
and $R'_2$ to $R'_6$ being, independently of each other, carbon-based radicals, especially linear or branched hydrocarbon-based radicals (alkyl), containing 1 to 12 and especially 1 to 6 carbon atoms, and possibly comprising 1 to 4 heteroatoms, especially O;
and
ii) linear, branched and/or cyclic, saturated or unsaturated $C_1$-$C_{30}$ alkyl radicals, optionally comprising 1 to 3 heteroatoms chosen from O, S, F and N;
it being understood that at least one of the radicals R and/or R' is of formula (III).
The group A may especially be of formula:

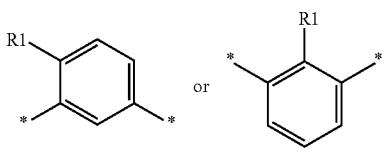

with $R_1$ and the *s being as defined above.
In particular, $R_1$ may be a methyl group, which leads to a group A of formula:

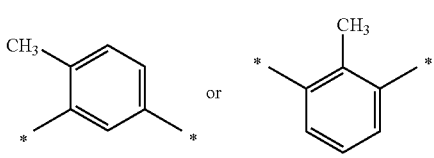

in which the *s are as defined above.
In particular, the compounds according to the invention may be in the form of a mixture linked to the fact that A may be a mixture of 2,4-tolylene and 2,6-tolylene, especially in (2,4 isomer)/(2,6 isomer) proportions ranging from 95/5 to 80/20.

According to the invention, at least one of the radicals R and/or R' should be of formula (III):

In this formula, L is preferably a divalent carbon-based radical, especially a linear, branched and/or cyclic, saturated or unsaturated hydrocarbon-based radical (alkylene), containing 1 to 18 carbon atoms, and possibly comprising 1 to 4 heteroatoms chosen from N, O and S. In the radical L, the carbon-based chain may be interrupted with the heteroatom(s) and/or may comprise a substituent comprising the heteroatom(s).

In particular, L may have the structure —$(CH_2)_n$- with n=1 to 18, especially 2 to 12 or even 3 to 8. Preferably, L is chosen from methylene, ethylene, propylene and butylene radicals and especially n-butylene or octylene.

The radical L may also be branched, for example of the type —$CH_2$—$CH(CH_3)$—, which leads to the radical of formula (III) below:

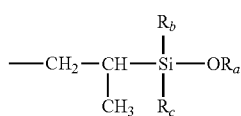

The radical $R_a$ may be a carbon-based radical, especially a linear, branched and/or cyclic, saturated or unsaturated hydrocarbon-based radical (alkyl), containing 1 to 18 carbon atoms, and possibly comprising 1 to 8 heteroatoms chosen from N, O, Si and S. The carbon-based chain may be interrupted with the heteroatom(s) and/or may comprise a substituent comprising the heteroatom(s); the heteroatoms may especially form one or more —SiO— (or —OSi—) groups.

Thus, the radical $R_a$ may have the structure —$(CH_2)_{n'}$-$CH_3$ with n'=0 to 17, especially 1 to 12 or even from 1 to 6. In particular, $R_a$ may be methyl, ethyl, propyl or butyl.

It may also have the structure —$(CH_2)_x$-O—$(CH_2)_z$-$CH_3$ or —$(CH_2)_x$-O—$(CH_2)_y$-O—$(CH_2)_z$-$CH_3$, with x=1 to 10, preferably 2; y=1 to 10, preferably 2, and z=0 to 10, preferably 0 or 1.

The radical $R_a$ may also have the structure —$SiR_4R_5R_6$ (in the case where n=0), in which $R_4$, $R_5$ and $R_6$ are, independently of each other, preferably alkyl radicals containing 1 to 12 carbon atoms and especially 1 to 6 carbon atoms; in particular, $R_4$, $R_5$ and/or $R_6$ may be chosen from methyl, ethyl, propyl and butyl.

The radical $R_a$ may also be a silicone radical of formula:

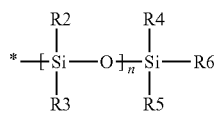

in which $R_2$ to $R_6$ are, independently of each other, preferably alkyl radicals containing 1 to 12 carbon atoms and especially 1 to 6 carbon atoms; in particular, $R_2$ to $R_6$ may be chosen from methyl, ethyl, propyl and butyl;

and in particular a radical:

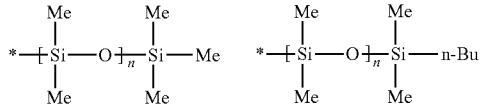

with n=1 to 100; and even more particularly a radical:

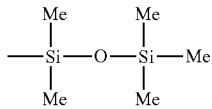

The radicals $R_b$ and $R_c$, which may be identical or different, may be carbon-based radicals, especially linear, branched and/or cyclic, saturated or unsaturated hydrocarbon-based radicals (alkyl), containing 1 to 18 carbon atoms, and possibly comprising 1 to 8 heteroatoms chosen from N, O, Si and S. In these radicals, the carbon-based chain may be interrupted with the heteroatom(s) and/or may comprise a substituent comprising the heteroatom(s); the heteroatoms may especially form one or more —SiO— (or —OSi—) groups.

Thus, they may have the structure —$(CH_2)$m-$CH_3$ with m=0 to 17, especially 1 to 12 or even 2 to 5; in particular, $R_b$ and/or $R_c$ may be methyl, ethyl, propyl or butyl.

They may also have the structure —O—$(CH_2)$m'-$CH_3$ with m'=0 to 5, especially 1 to 4 and in particular methoxy or ethoxy.

They may also have the structure —O—$(CH_2)$x-O—$(CH_2)$z-$CH_3$ or —O—$(CH_2)$x-O—$(CH_2)$y-O—$(CH_2)$z-$CH_3$, with x=1 to 10, preferably 2; y=1 to 10, preferably 2, and z=0 to 10, preferably 0 or 1.

They may also have the structure:

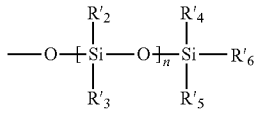

with n being between 0 and 100, especially between 1 and 80 or even 2 to 20;

and $R'_2$ to $R'_6$ being, independently of each other, preferably alkyl radicals containing 1 to 12 carbon atoms and especially 1 to 6 carbon atoms; in particular, $R'_2$ to $R'_6$ may be chosen from methyl, ethyl, propyl and butyl.

When they are of formula (III), the radicals R and/or R' are preferably chosen from the following radicals:

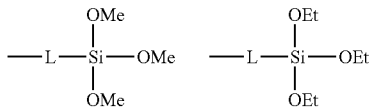

-continued

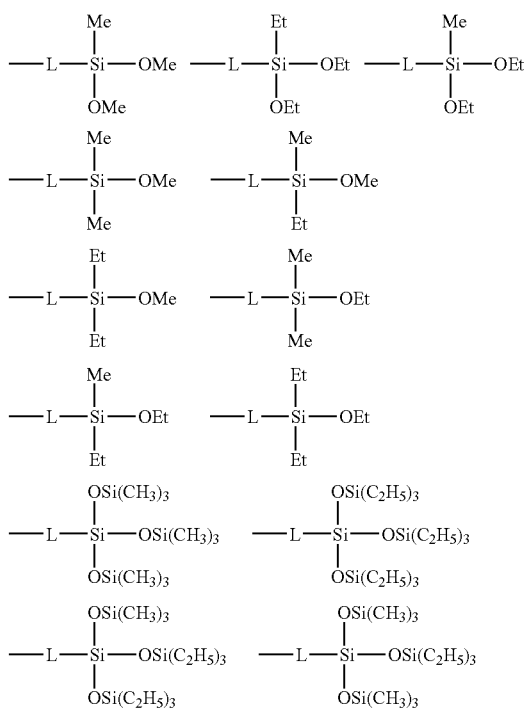

and also those of formula:

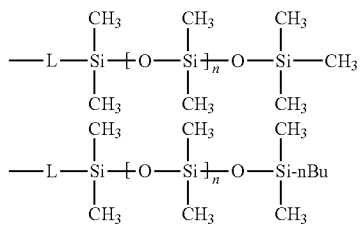

with n ranging from 0 to 100, and in particular

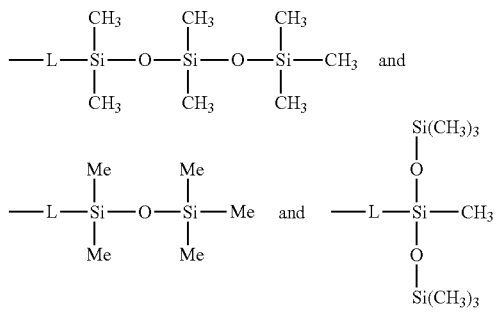

or alternatively

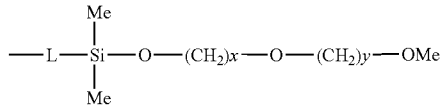

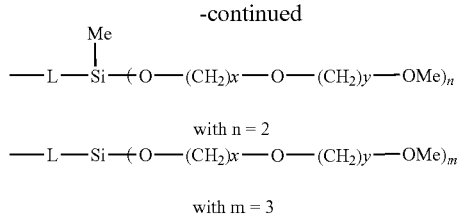

with n = 2 with m = 3 in which x=1 to 10, preferably 2; and y=1 to 10, preferably 2;

and L being as defined above.

Preferably, in these formulae, L is a linear or branched $C_1$-$C_8$ alkylene radical, especially methylene, ethylene, propylene or butylene and especially n-butylene or octylene, or of formula —$CH_2$—$CH(CH_3)$—.

In one particular embodiment, R and R', which may be identical or different, are both of formula (III).

In another embodiment, one of the radicals R or R' represents a linear, branched and/or cyclic, saturated or unsaturated $C_1$-$C_{30}$ alkyl radical, optionally comprising 1 to 3 heteroatoms chosen from O, S, F and N.

This proves to be particularly advantageous for giving the compounds of formula (I) a universal nature, i.e. enabling them to texture, simultaneously, polar or apolar carbon-based media, linear or cyclic silicone media, and mixed oils, i.e. partially silicone-based carbon-based oils, and also mixtures thereof.

The carbon chain may be interrupted with the heteroatom(s) and/or may comprise a substituent comprising the heteroatom(s), especially in the form of a carbonyl group (—CO—), one or more hydroxyl radicals (—OH), and/or an ester radical —COOR" with R"=linear or branched alkyl radical containing 1 to 8 carbon atoms.

Thus, the radical R or R' may be a group chosen from:

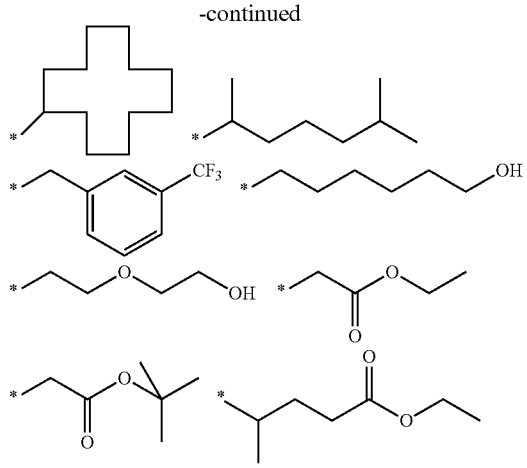

with * having the definition given above.

In one preferred embodiment, R or R' represents a branched, especially mono-branched, preferably acyclic, saturated or unsaturated alkyl radical containing 3 to 16 carbon atoms, especially 4 to 12 or even 4 to 8 carbon atoms, and optionally comprising 1 to 3 heteroatoms chosen from O, S, F and/or N, preferably O and/or N.

In particular, R or R' may be tert-butyl or 2-ethylhexyl radicals or of formula:

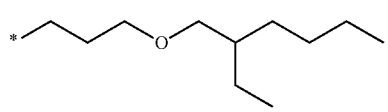 [SMILES: *CCCOCC(CC)CCCC]

When the compound of formula (I) comprises a radical R that is an alkyl radical, and thus a radical R' that is of formula (III), the ratio between $n_R$ and $n_{R'}$ is preferably between 5/95 and 95/5, for example between 10/90 and 90/10, in particular between 40/60 and 85/15, especially between 50/50 and 80/20, or even between 60/40 and 75/25;

with $n_R$ being the number of moles of amine $NH_2$—R and $n_{R'}$ being the number of moles of amine $NH_2$—R' used to prepare the compound of formula (I).

The compounds according to the invention may be in the form of salts and/or of isomers of compounds of formula (I).

In general, the compounds of general formula (I) according to the invention may be prepared as described in patent application FR 2 910 809.

The compounds of silicone bis-urea type described above may be mixed with other non-silicone bis-urea compounds. According to a first aspect, the non-silicone bis-urea compounds may correspond to the general formula (II) below:

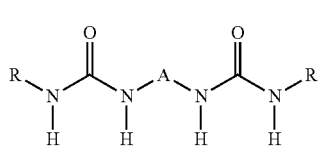

(II)

in which:

A is a group of formula:

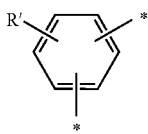

with R' being a linear or branched $C_1$ to $C_4$ alkyl radical and the *s symbolizing the points of attachment of the group A to each of the two nitrogen atoms of the rest of the compound of general formula (II), and R is a saturated or unsaturated, non-cyclic, mono-branched $C_6$ to $C_{15}$ alkyl radical whose hydrocarbon-based chain is optionally interrupted with 1 to 3 heteroatoms chosen from O, S and N, or a salt or isomer thereof.

According to one preferred embodiment of the invention, the group represented by A is a group of formula:

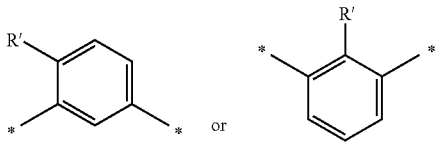

with R' and the *s being as defined above.

In particular, R' may be a methyl group, and the group A is then more particularly a group of formula:

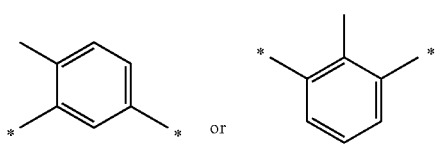

with the *s being as defined above.

According to a first embodiment of the invention, R may be chosen from the mono-branched radicals of general formula $C_nH_{2n+1}$, n being an integer ranging from 6 to 15, in particular from 7 to 9 or even equal to 8.

Thus, the two groups R of the compound of formula (I) may represent, respectively, a group:

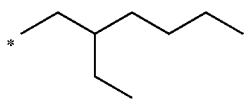

with * symbolizing the point of attachment of each of the groups R to each of the nitrogen atoms of the rest of the compound of general formula (I).

According to a second embodiment of the invention, R may be chosen from the mono-branched radicals of general formula $C_{m-p}H_{2m+1-2p}X_p$, p being equal to 1, 2 or 3, preferably equal to 1, m being an integer ranging from 6 to 15, preferably from 10 to 14, in particular from 10 to 12, or even equal to 11, and X representing sulfur and/or oxygen atoms, in particular oxygen atoms.

More particularly, R may be a radical of formula $C_mH_{2m}X$—$(C_{p'}H_{2p'}X')_r$—$C_xH_{2x+1}$, in which X and X' are, independently of each other, an oxygen or sulfur atom, preferably oxygen, r is 0 or 1, m', p' and x are integers such that their sum ranges from 6 to 15, in particular from 10 to 12, or even is equal to 11, and it being understood that at least one of the carbon-based chains $C_mH_{2m}$, $C_{p'}H_{2p'}$, or $C_xH_{2x+1}$ is branched.

Preferably, it is the chain $C_xH_{2x+1}$ that is branched, preferably r is equal to 0, preferably m' is an integer ranging from 1 to 10, especially from 2 to 6, in particular is equal to 3, and/or preferably x is an integer ranging from 4 to 16, especially from 6 to 12 and in particular is equal to 8.

Thus, the two groups R of the compound of formula (I) may represent, respectively, a group:

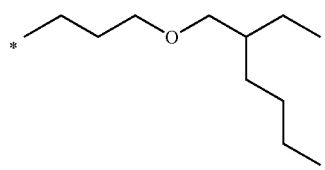

with * symbolizing the point of attachment of each of the groups R to each of the nitrogen atoms of the rest of the compound of general formula (I).

Such compounds may be present in the compositions according to the invention as mixtures with isomers, especially positional isomers on the group A, especially in 95/5 or 80/20 proportions.

As emerges from the examples below, the presence of one or the other of these radicals in the molecule of general formula (II) proves to be particularly advantageous for giving a universal nature, within the meaning of the invention, to the corresponding bis-urea derivatives.

As non-limiting representations of the compounds that are most particularly suitable for the invention, mention may be made more particularly of the following compounds, used pure or as a mixture:

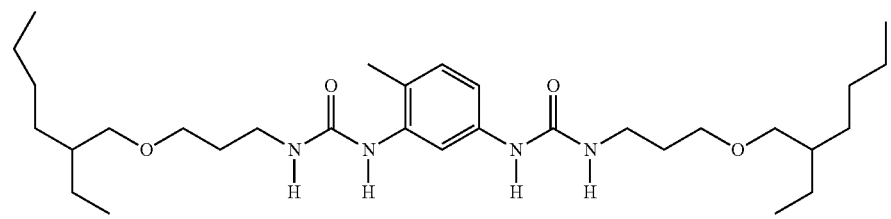

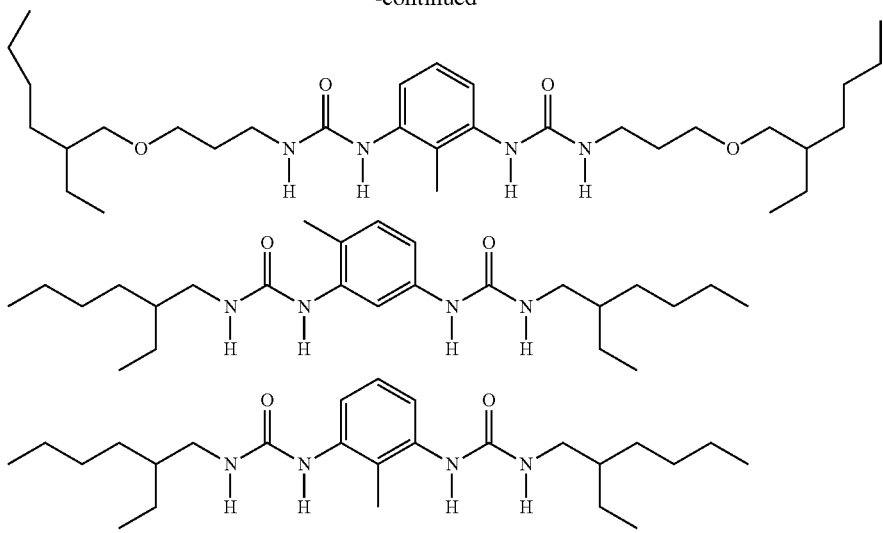

and the salts thereof.

According to another aspect of the invention, the non-silicone bis-urea derivatives of formula (III) below:

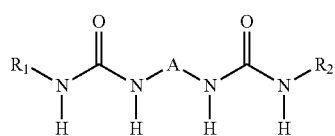

in which:

A is a group of formula:

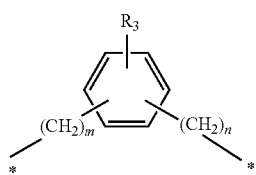

with $R_3$ being a hydrogen atom or a linear or branched $C_1$ to $C_4$ alkyl radical, n and m being, independently of each other, equal to 0 or 1, and

* symbolizing the point of attachment of the group A to the two nitrogen atoms of the residue of the compound of general formula (III), $R_1$ is a saturated or unsaturated, non-cyclic branched $C_3$ to $C_{15}$ carbon-based radical optionally containing from 1 to 3 heteroatoms chosen from O, S, F and N and/or a carbonyl, and combinations thereof, $R_2$ is different from $R_1$ and is chosen from linear, branched or cyclic, saturated or unsaturated $C_1$-$C_{24}$ alkyl radicals optionally containing from 1 to 3 heteroatoms chosen from O, S, F and N, and optionally substituted with:
1, 2 or 3 hydroxyl radicals,
an ester radical (—COOR$_4$), with $R_4$ being a linear or branched alkyl radical containing from 1 to 8, especially 1 to 6 or even 2 to 4 carbon atoms;
a saturated, unsaturated or aromatic cyclic radical containing from 5 to 12 carbon atoms, in particular a phenyl radical optionally substituted with one or more radicals, which may be identical or different, chosen from $C_1$-$C_4$ alkyl and trifluoromethyl radicals, or a morpholine derivative, and/or
one or more linear or branched $C_1$-$C_4$ alkyl radicals,
or a salt or isomer thereof.

In particular, n and m are equal, and more particularly equal to zero, and $R_3$ is a radical $R'_3$ as defined below. Thus, preferably, A represents a group

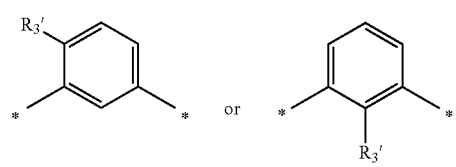

with $R_3'$ being a linear or branched $C_1$ to $C_4$ alkyl radical and * symbolizing the points of attachment of the group A to the two nitrogen atoms of the residue of the compound of general formula (III).

According to one variant of the invention, the compound of general formula (III) comprises, as A, at least one group chosen from:

with $R_3'$ and * being as defined above.

In particular, $R_3'$ may be a methyl group, and in this case the group A represents a group

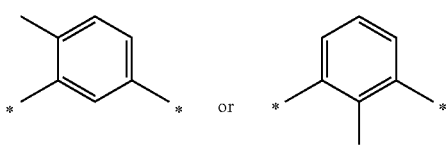

* being as defined above.

In particular, the compounds are such that A is a mixture of 2,4-tolylene and 2,6-tolylene, especially in (2,4 isomer)/(2,6 isomer) proportions ranging from 95/5 to 80/20.

According to one embodiment of the invention, the compound of general formula (III) comprises, as $R_1$, a branched $C_6$-$C_{15}$ radical.

According to one embodiment of the invention, the compound of general formula (III) comprises, as $R_1$, a group chosen from:

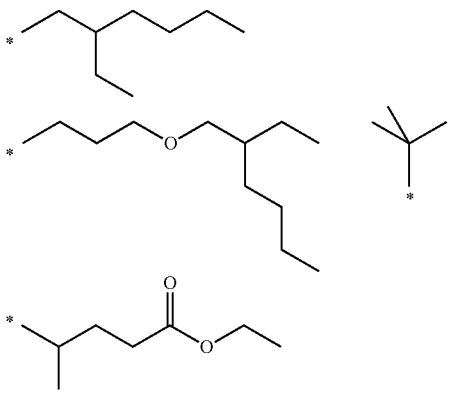

with * symbolizing the point of attachment of the group $R_1$ to the nitrogen of the residue of the compound of general formula (III).

As emerges from the examples below, the presence of one and/or another of the two radicals in the molecule of general formula (III) proves to be particularly advantageous for giving a universal nature within the meaning of the invention to the corresponding asymmetric bis-urea derivatives.

As regards $R_2$, which is different from $R_1$, it may be advantageously chosen from the following groups:

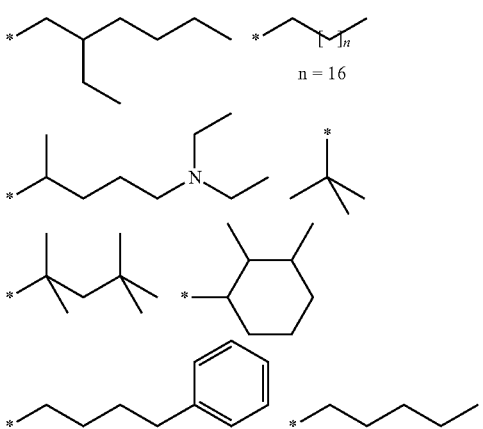

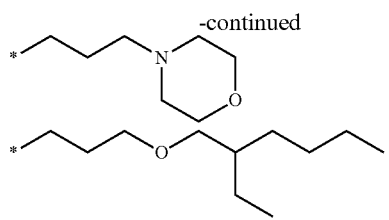

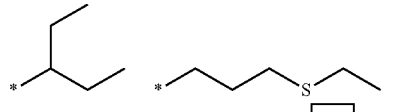

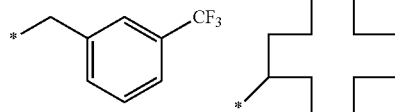

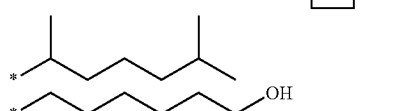

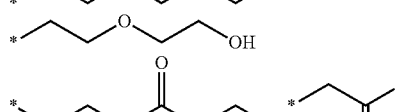

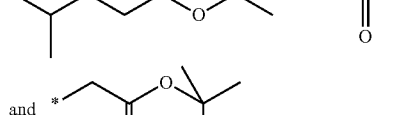

and 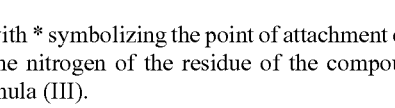

with * symbolizing the point of attachment of the group $R_2$ to the nitrogen of the residue of the compound of general formula (III).

In general, the compounds described may be prepared as described in patent application FR 2 910 809.

Block Polymers

It is also possible to use, as fatty-phase rheological agent, grafted-block or block polymers.

It is especially possible to use grafted or block copolymers comprising at least one block of polyorganosiloxane type and at least one block of a free-radical polymer, for instance grafted copolymers of acrylic/silicone type, which may be used especially when the non-aqueous medium is a silicone phase.

It is also possible to use grafted-block or block copolymers comprising at least one block of polyorganosiloxane type and at least one block of a polyether. The polyorganopolysiloxane block may especially be a polydimethylsiloxane or a poly($C_2$-$C_{18}$)alkylmethylsiloxane; the polyether block may be a poly ($C_2$-$C_{18}$)alkylene, in particular polyoxyethylene and/or polyoxypropylene. In particular, dimethicone copolyols or ($C_2$-$C_{18}$)alkyl dimethicone copolyols such as those sold under the name "Dow Corning 3225C" by the company Dow Corning, and lauryl methicones such as those sold under the name "Dow Corning Q2-5200" by the company Dow Corning, may be used.

Grafted-block or block copolymers that may also be mentioned include those comprising at least one block resulting from the polymerization of at least one ethylenic monomer containing one or more optionally conjugated ethylenic bonds, for instance ethylene or dienes such as butadiene and isoprene, and of at least one block of a vinyl polymer and better still a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of an ethylene-propylene block, and the polymerization of butadiene leads, after hydrogenation, to the formation of an ethylene-butylene block. Among these polymers that may be mentioned are block copolymers, especially of "diblock" or "triblock" type such as polystyrene/polyisoprene (SI), polystyrene/polybutadiene (SB) such as those sold under the name "Luvitol HSB" by BASF, of the type such as polystyrene/copoly(ethylene-propylene) (SEP) such as those sold under the name "Kraton" by Shell Chemical Co. or of the type such as polystyrene/copoly(ethylene-butylene) (SEB). Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS) and Kraton D-1107 (SIS) may be used in particular. The polymers are generally known as hydrogenated or non-hydrogenated diene copolymers.

Gelled Permethyl 99A-750, 99A-753-59 and 99A-753-58 (mixture of triblock and of star polymer), Versagel 5960 from Penreco (triblock+star polymer); OS129880, OS129881 and OS84383 from Lubrizol (styrene/methacrylate copolymer) may also be used.

As grafted-block or block copolymers comprising at least one block resulting from the polymerization of at least one ethylenic monomer containing one or more ethylenic bonds and of at least one block of an acrylic polymer, mention may be made of poly(methyl methacrylate)/polyisobutylene diblock or triblock copolymers or grafted copolymers containing a poly(methyl methacrylate) skeleton and polyisobutylene grafts.

As grafted-block or block copolymers comprising at least one block resulting from the polymerization of at least one ethylenic monomer containing one or more ethylenic bonds and of at least one block of a polymer such as a $C_2$-$C_{18}$ polyalkylene (especially polyoxyethylene and/or polyoxypropylene), mention may be made of polyoxyethylene/polybutadiene or polyoxyethylene/polyisobutylene diblock or triblock copolymers.

Cholesterol-Based Liquid-Crystal Agents

The term "liquid-crystal agents" means compounds that generate a mesomorphic state, i.e. a state for which melting of the crystals affords liquids that have optical properties comparable to those of certain crystals. These compounds are more specifically defined in the chapter Liquid Crystals in Ullmann's encyclopaedia.

These liquid-crystal agents are described in particular in the patents or patent applications EP 545 409, WO 94/109 086, EP 709 445, GB 2 282 145, GB 2 276 883, WO 95/132247, WO 95/132248, EP 686 674 and EP 711 780.

These liquid-crystal agents may react in response to the vibrations by a change in viscosity and/or by a change in colour.

More particularly, the compounds that generate a mesomorphic state are compounds containing a cholesterol-based function, the structure of which is as follows:

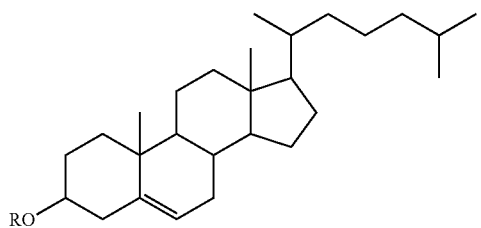

R is an alkyl or alkylcarbonyl group containing from 1 to 30 carbon atoms optionally substituted with cyclic, aromatic groups, halogens, branched or unbranched.

As non-limiting examples of liquid-crystal agents that satisfy this definition, mention may be made of: cholesteryl erucyl carbonate, cholesteryl methyl carbonate, cholesteryl oleyl carbonate, cholesteryl para-nonyl phenyl carbonate, cholesteryl phenyl carbonate, cholesteryl acetate, cholesteryl benzoate, cholesteryl butyrate, cholesteryl isobutyrate, cholesteryl chloride, cholesteryl chloroacetate, cholesteryl cinnamate, cholesteryl crotonate, cholesteryl decanoate, cholesteryl erucate, cholesteryl heptanoate, cholesteryl hexanoate, cholesteryl myristate, cholesteryl nonanoate, cholesteryl octanoate, cholesteryl oleate, cholesteryl propionate, cholesteryl valerate and dicholesteryl carbonate.

The composition according to the invention may comprise an aqueous continuous phase or an oily continuous phase.

The term "composition with an aqueous continuous phase" means that the composition has a conductivity, measured at 25° C., of greater than or equal to 23 µS/cm (microSiemens/cm), the conductivity being measured, for example, using an MPC227 conductimeter from Mettler Toledo and an Inlab730 conductivity measuring cell. The measuring cell is immersed in the composition so as to remove the air bubbles that might be formed between the two electrodes of the cell. The conductivity reading is taken once the conductimeter value has stabilized. A mean is determined on at least three successive measurements.

The term "composition with an oily continuous phase" means that the composition has a conductivity, measured at 25° C., of less than 23 µS/cm (microSiemens/cm), the conductivity being measured, for example, using an MPC227 conductimeter from Mettler Toledo and an Inlab730 conductivity measuring cell. The measuring cell is immersed in the composition so as to remove the air bubbles that might be formed between the two electrodes of the cell. The conductivity reading is taken once the conductimeter value has stabilized. A mean is determined on at least three successive measurements.

The compositions may contain from 1% to 60% of fatty-phase rheological agent. Preferably, the composition contains from 2% to 50% and better still from 5% to 40% by weight of fatty-phase rheological agent.

When the composition comprises a fatty-phase rheological agent, it comprises an oily continuous phase.

Aqueous Phase

The composition in accordance with the invention may comprise an aqueous phase comprising water and/or at least one water-soluble solvent.

In the present invention, the term "water-soluble solvent" denotes a compound that is liquid at room temperature and water-miscible (miscibility in water of greater than 50% by weight at 25° C. and atmospheric pressure).

The water-soluble solvents that may be used in the compositions according to the invention may also be volatile.

Among the water-soluble solvents that may be used in the compositions in accordance with the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in a content ranging from 1% to 95% by weight, preferably ranging from 5% to 80% by weight and preferentially ranging from 10% to 60% by weight relative to the total weight of the composition.

The aqueous phase according to the invention may also comprise at least one hydrophilic film-forming polymer and/or at least one hydrophilic thickeners and/or at least one surfactant, such as those listed previously.

Hydrophilic Film-Forming Polymer

In the present invention, the term "film-forming polymer" means a polymer that is capable, by itself or in the presence of an auxiliary film-forming agent, of forming a macroscopically continuous film that adheres to the eyelashes, and preferably a cohesive film, and better still a film whose cohesion and mechanical properties are such that the film can be isolated and manipulated in isolation, for example when the film is made by pouring onto a non-stick surface, for instance a Teflon-coated or silicone-coated surface.

In general, the solids content of "film-forming polymer" in the composition may range from 0.1% to 40%, preferably from 0.5% to 30% and better still from 1% to 10% by weight relative to the total weight of the composition. The hydrophilic film-forming polymer may be a water-soluble polymer or may be in dispersion in an aqueous medium.

Among the film-forming polymers that may be used in the composition of the present invention, mention may be made of synthetic polymers, of free-radical type or of polycondensates type, and polymers of natural origin, and mixtures thereof.

Examples of water-soluble film-forming polymers that may be mentioned include:
  proteins, for instance proteins of plant origin such as wheat or soybean proteins; proteins of animal origin such as keratins, for example keratin hydrolysates and sulfonic keratins;
  cellulose polymers such as hydroxyethylcellulose, hydroxypropylcellulose, methylcellulose, ethylhydroxyethylcellulose and carboxymethylcellulose, and also quaternized cellulose derivatives;
  acrylic polymers or copolymers, such as polyacrylates or polymethacrylates;
  vinyl polymers, for instance polyvinyl-pyrrolidones, copolymers of methyl vinyl ether and of maleic anhydride, the copolymer of vinyl acetate and of crotonic acid, copolymers of vinylpyrrolidone and of vinyl acetate; copolymers of vinylpyrrolidone and of caprolactam; polyvinyl alcohol;
  anionic, cationic, amphoteric or nonionic chitin or chitosan polymers;
  gum arabics, guar gum, xanthan derivatives and karaya gum;
  alginates and carrageenans;
  glycoaminoglycans, and hyaluronic acid and derivatives thereof;
  shellac resin, sandarac gum, dammar resins, elemi gums and copal resins;
  deoxyribonucleic acid;
  mucopolysaccharides such as chondroitin sulfates;
  and mixtures thereof.

The film-forming polymer may also be present in the composition in the form of particles dispersed in an aqueous phase, which is generally known as a latex or pseudolatex. The techniques for preparing these dispersions are well known to those skilled in the art.

Aqueous dispersions of film-forming polymer that may be used include the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® or Daitosol 5000 SJ® by the company Daito Kasey Kogyo; Syntran 5760® by the company Interpolymer, Allianz Opt® by the company Rohm & Haas or the aqueous polyurethane dispersions sold under the names Neorez R-981® and Neorez R-974® by the company Avecia-Neoresins, Avalure UR-405®, Avalure UR-410®, Avalure UR-425®, Avalure UR-450®, Sancure 875®, Avalure UR-445® and Sancure 2060® by the company Noveon, Impranil 85® by the company Bayer, Aquamere H-1511® by the company Hydromer; the sulfopolyesters sold under the brand name Eastman AQ® by the company Eastman Chemical Products, vinyl dispersions, for instance Mexomer PAM®, aqueous polyvinyl acetate dispersions, for instance Vinybran® from the company Nisshin Chemical or those sold by the company Union Carbide, aqueous dispersions of vinylpyrrolidone, dimethylaminopropylmethacrylamide and lauryldimethylpropylmethacrylamidoammonium chloride terpolymer, such as Styleze W from ISP, aqueous dispersions of polyurethane/polyacrylic hybrid polymers such as those sold under the references Hybridur® by the company Air Products or Duromer® from National Starch, and dispersions of core/shell type: for example those sold by the company Atofina under the reference Kynar (core: fluoro; shell: acrylic) or alternatively those described in document U.S. Pat. No. 5,188,899 (core: silica; shell: silicone), and mixtures thereof.

According to one preferred embodiment, the acrylic polymers or copolymers, such as polyacrylates or polymethacrylates, will be used in particular in contents ranging from 1% to 40%, in particular from 5% to 30%, preferably from 8% to 15% and better still from 8% to 12% by weight relative to the total weight of the composition.

According to one particular embodiment, the composition in accordance with the invention comprises, as hydrophilic film-forming polymers, at least a combination of a cationic polymer and an anionic polymer.

The cationic polymer may be chosen from quaternary cellulose ether derivatives, copolymers of cellulose with a water-soluble quaternary ammonia monomer, cyclopolymers, cationic polysaccharides, cationic silicone polymers, vinylpyrrolidone/dialkylaminoalkyl acrylate or methacrylate quaternized or non-quaternized copolymers, quaternary polymers of vinylpyrrolidone and of vinylimidazole, and polyaminoamides, and mixtures thereof.

Preferably, the cationic polymer is a hydroxy($C_1$-$C_4$)alkylcellulose comprising quaternary ammonium groups.

The anionic polymer is advantageously chosen from:
  A) homopolymers or copolymers of acrylic or methacrylic acid or salts thereof, copolymers of acrylic acid and of acrylamide and salts thereof, and the sodium salts of polyhydroxycarboxylic acids such as the copolymers of acrylic acid and of acrylamide sold in the form of their sodium salt under the names Reten® by the company Hercules, sodium polymethacrylate sold under the name Darvan No. 7® by the company Vanderbilt, and the sodium salts of polyhydroxycarboxylic acids sold under the name Hydagen F® by the company Henkel;

B) copolymers of acrylic or methacrylic acid with a monoethylenic monomer such as ethylene, styrene, vinyl esters, acrylic or methacrylic acid esters, optionally grafted onto a polyalkylene glycol such as polyethylene glycol; copolymers of this type comprising in their chain an optionally N-alkylated and/or hydroxyalkylated acrylamide unit, copolymers of acrylic acid and of a $C_1$-$C_4$ alkyl methacrylate, and terpolymers of vinylpyrrolidone, of acrylic acid and of a $C_1$-$C_{20}$ alkyl methacrylate;

C) copolymers derived from crotonic acid, such as those comprising in their chain vinyl acetate or propionate units and optionally other monomers such as allylic or methallylic esters, a vinyl ether or vinyl ester of a linear or branched saturated carboxylic acid with a long hydrocarbon-based chain, such as those comprising at least 5 carbon atoms, these polymers possibly being grafted;

D) polymers derived from maleic, fumaric or itaconic acid or anhydride with vinyl esters, vinyl ethers, vinyl halides, phenylvinyl derivatives or acrylic acid and esters thereof; copolymers of maleic, citraconic or itaconic anhydride and of an allylic or methallylic ester optionally comprising an acrylamide or methacrylamide group, an α-olefin, acrylic or methacrylic esters, acrylic or methacrylic acid or vinylpyrrolidone in their chain, the anhydride functions being monoesterified or monoamidated;

E) polyacrylamides comprising carboxylate groups,

F) deoxyribonucleic acid;

G) copolymers of at least one dicarboxylic acid, of at least one diol and of at least one difunctional aromatic monomer bearing a group —$SO_3M$ with M representing a hydrogen atom, an ammonium ion $NH_4^+$ or a metal ion;

and mixtures thereof.

The anionic polymers that are more particularly preferred are chosen from non-crosslinked anionic polymers such as the methyl vinyl ether/monoesterified maleic anhydride copolymers sold under the name Gantrez ES 425 by the company ISP, the acrylic acid/ethyl acrylate/N-tert-butylacrylamide terpolymers sold under the name Ultrahold Strong by the company BASF, the copolymers of methacrylic acid and of methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer MAEX or MAE by the company BASF, the vinylpyrrolidone/acrylic acid/lauryl methacrylate terpolymers sold under the name Acrylidone LM by the company ISP and the acrylic or methacrylic acid homopolymers sold, for example, under the name Versicol E 5 or poly(sodium methacrylate) sold under the name Darvan 7 by the company Vanderbilt, and mixtures thereof.

The anionic polymer is preferably a sodium polymethacrylate.

The composition in accordance with the invention may comprise a plasticizer that promotes the formation of a film with the film-forming polymer. Such a plasticizer may be chosen from any of the compounds known to those skilled in the art as being capable of filling the desired function.

Hydrophilic Thickener

The composition according to the invention may comprise at least one hydrophilic thickener.

These thickeners may be used alone or in combination. These thickeners may be chosen especially from cellulose polymers and gums.

The term "hydrophilic thickener" means a thickener that is soluble or dispersible in water.

Hydrophilic thickeners that may be mentioned in particular include water-soluble or water-dispersible thickening polymers. These may be chosen especially from:

modified or unmodified carboxyvinyl polymers, such as the products sold under the name Carbopol (CTFA name: carbomer) by the company Goodrich;

homopolymers or copolymers of acrylic or methacrylic acids or the salts thereof and the esters thereof and in particular the products sold under the names Versicol F® or Versicol K® by the company Allied Colloid, Ultrahold 8® by the company Ciba-Geigy, polyacrylates and polymethacrylates such as the products sold under the names Lubragel and Norgel by the company Guardian or under the name Hispagel by the company Hispano Chimica, and polyacrylic acids of the type such as Synthalen K;

polyacrylamides;

copolymers of acrylic acid and of acrylamide sold in the form of the sodium salt thereof under the names Reten® by the company Hercules, the sodium polymethacrylates sold under the name Darvan 7® by the company Vanderbilt, and the sodium salts of polyhydroxycarboxylic acids sold under the name Hydagen F® by the company Henkel;

optionally crosslinked and/or neutralized 2-acrylamido-2-methylpropanesulfonic acid polymers and copolymers, for instance poly(2-acrylamido-2-methylpropanesulfonic acid) sold by the company Clariant under the name Hostacerin AMPS (CTFA name: ammonium polyacryldimethyltauramide);

crosslinked anionic copolymers of acrylamide and of AMPS, which are in the form of a W/O emulsion, such as those sold under the name Sepigel 305 (CTFA name: Polyacrylamide/C13-14 isoparaffin/Laureth-7) and under the name Simulgel 600 (CTFA name: acrylamide/sodium acryloyldimethyltaurate copolymer/isohexadecane/polysorbate 80) by the company SEPPIC;

polyacrylic acid/alkyl acrylate copolymers of Pemulen type;

polysaccharide biopolymers, for instance xanthan gum, guar gum, gum arabic, locust bean gum, acacia gum, scleroglucans, chitin and chitosan derivatives, carrageenans, gellans, alginates, celluloses such as microcrystalline cellulose, carboxymethylcellulose, hydroxymethylcellulose, hydroxyethylcellulose and hydroxypropylcellulose;

hydrophilic fumed silicas obtained by high-temperature hydrolysis of a volatile silicon compound in an oxhydric flame, producing a finely divided silica. Hydrophilic silicas have a large number of silanol groups at their surface. Such hydrophilic silicas are sold, for example, under the names Aerosil 130®, Aerosil 200®, Aerosil 255®, Aerosil 300® and Aerosil 380® by the company Degussa, Cab-O-Sil HS-5®, Cab-O-Sil EH-5®, Cab-O-Sil LM-130®, Cab-O-Sil MS-55® and Cab-O-Sil M-5® by the company Cabot. They preferably have a particle size that may be nanometric to micrometric, for example ranging from about 5 to 200 nm;

associative polymers, for instance PEG-150/stearyl alcohol/SMDI Copolymer sold under the name Aculyn 46 by Rohm & Haas, or Steareth-100/PEG-136/HDI copolymer sold under the name Rheolate FX 1100 by Elementis);

and mixtures thereof.

The hydrophilic thickener may be chosen from associative polymers. For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Among the associative anionic polymers that may be mentioned are those comprising at least one hydrophilic unit and at least one fatty-chain allyl ether unit, more particularly from those in which the hydrophilic unit consists of an ethylenic unsaturated anionic monomer, more particularly a vinylcarboxylic acid and most particularly an acrylic acid, a methacrylic acid or mixtures thereof, and in which the fatty-chain allyl ether unit corresponds to the monomer of formula (I) below:

$$CH_2=C(R')CH_2OB_nR \qquad (I)$$

in which R' denotes H or $CH_3$, B denotes an ethylenoxy radical, n is 0 or denotes an integer ranging from 1 to 100, and R denotes a hydrocarbon-based radical chosen from alkyl, arylalkyl, aryl, alkylaryl and cycloalkyl radicals containing from 8 to 30 carbon atoms, preferably 10 to 24 and even more particularly from 12 to 18 carbon atoms.

Anionic amphiphilic polymers of this type are described and prepared, according to an emulsion polymerization process, in patent EP-0 216 479.

Associative anionic polymers that may also be mentioned include anionic polymers comprising at least one hydrophilic unit of olefinic unsaturated carboxylic acid type, and at least one hydrophobic unit exclusively of $(C_{10}-C_{30})$alkyl ester of unsaturated carboxylic acid type. Examples that may be mentioned include the anionic polymers described and prepared according to U.S. Pat. Nos. 3,915,921 and 4,509,949.

Cationic associative polymers that may be mentioned include quaternized cellulose derivatives and polyacrylates containing amine side groups.

The nonionic associative polymers may be chosen from:
  celluloses modified with groups comprising at least one fatty chain, for instance hydroxyethyl-celluloses modified with groups comprising at least one fatty chain, such as alkyl groups, especially of $C_8$-$C_{22}$, arylalkyl and alkylaryl groups, such as Natrosol Plus Grade 330 CS($C_{16}$ alkyls) sold by the company Aqualon,
  celluloses modified with polyalkylene glycol alkylphenyl ether groups,
  guars such as hydroxypropyl guar, modified with groups comprising at least one fatty chain such as an alkyl chain,
  copolymers of vinylpyrrolidone and of fatty-chain hydrophobic monomers,
  copolymers of $C_1$-$C_6$ alkyl methacrylates or acrylates and of amphiphilic monomers comprising at least one fatty chain,
  copolymers of hydrophilic methacrylates or acrylates and of hydrophobic monomers comprising at least one fatty chain, for instance the polyethylene glycol methacrylate/lauryl methacrylate copolymer,
  associative polyurethanes,
  mixtures thereof.

Preferably, the associative polymer is chosen from associative polyurethanes. Associative polyurethanes are nonionic block copolymers comprising in the chain both hydrophilic blocks usually of polyoxyethylene nature, and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendant chains or chains at the end of a hydrophilic block. In particular, it is possible for one or more pendant chains to be provided. In addition, the polymer may comprise a hydrocarbon-based chain at one or both ends of a hydrophilic block. The associative polyurethanes may be blocked in triblock or multiblock form. The hydrophobic blocks may thus be at each end of the chain (for example: triblock copolymer with a hydrophilic central block) or distributed both at the ends and within the chain (for example multiblock copolymer). These polymers may also be graft polymers or starburst polymers. Preferably, the associative polyurethanes are triblock copolymers in which the hydrophilic block is a polyoxyethylene chain containing from 50 to 1000 oxyethylene groups. In general, the associative polyurethanes comprise a urethane bond between the hydrophilic blocks, whence the name.

By way of example, among the associative polymers that may be used in the invention, mention may be made of the polymer $C_{16}$-$OE_{120}$-$C_{16}$ from the company Servo Delden (under the name SER AD FX1100, which is a molecule containing a urethane function and having a weight-average molecular weight of 1300), OE being an oxyethylene unit. An associative polymer that may also be used is Rheolate 205 containing a urea function, sold by the company Rheox, or Rheolate 208 or 204. These associative polyurethanes are sold in pure form. The product DW 1206B from Rohm & Haas containing a $C_{20}$ alkyl chain with a urethane bond, sold at a solids content of 20% in water, may also be used.

It is also possible to use solutions or dispersions of these polymers, especially in water or in aqueous-alcoholic medium. Examples of such polymers that may be mentioned include SER AD FX1010, SER AD FX1035 and SER AD 1070 from the company Servo Delden, and Rheolate 255, Rheolate 278 and Rheolate 244 sold by the company Rheox. It is also possible to use the product DW 1206F and DW 1206J, and also Acrysol RM 184 or Acrysol 44 from the company Rohm & Haas, or alternatively Borchigel LW 44 from the company Borchers.

Oily Phase

The composition according to the invention may also comprise an oily phase.

This oily phase may comprise at least one oil as listed above, and/or at least one wax, and/or at least one lipophilic film-forming polymer and/or at least one fatty-phase rheological agent as mentioned previously.

Waxes

For the purposes of the present invention, the term "wax" means a lipophilic compound, which is solid at room temperature (25° C.), with a reversible solid/liquid change of state, which has a melting point of greater than or equal to 30° C., which may be up to 120° C.

The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes and may be of plant, mineral, animal and/or synthetic origin. In particular, the waxes have a melting point of greater than 25° C. and better still greater than 45° C.

The wax is present in a content at least equal to 15% by weight. Preferably, it is present in a content ranging from 15% to 40% by weight, better still from 16% to 35% and even better still from 16% to 30% by weight relative to the total weight of the composition.

Hydrocarbon-based waxes, for instance beeswax, lanolin wax or Chinese insect wax; rice wax, carnauba wax, candelilla wax, ouricury wax, esparto grass wax, cork fibre wax, sugarcane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched C8-C32 fatty chains.

Among these waxes that may especially be mentioned are hydrogenated jojoba oil, isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane)tetrabehenate sold under the name Hest 2T-4B by the company Heterene.

Mention may also be made of silicone waxes, for instance alkyl or alkoxy dimethicones containing from 16 to 45 carbon atoms, and fluoro waxes.

The wax obtained by hydrogenation of olive oil esterified with stearyl alcohol, sold under the name Phytowax Olive 18L57 or else the waxes obtained by hydrogenation of castor oil esterified with cetyl alcohol sold under the names Phytowax ricin 16L64 and 22L73 by the company Sophim may also be used. Such waxes are described in patent application FR-A-2 792 190.

According to one particular embodiment, the compositions in accordance with the invention may comprise at least one "tacky" wax, i.e. a wax with a tack of greater than or equal to 0.7 N·s and a hardness of less than or equal to 3.5 MPa.

The use of a tacky wax may especially allow the production of a cosmetic composition that is easy to apply to the eyelashes, that attaches well to the eyelashes and that leads to the formation of a smooth, uniform and thickening makeup.

The tacky wax used may especially have a tack ranging from 0.7 N·s to 30 N·s, in particular greater than or equal to 1 N·s, especially ranging from 1 N·s to 20 N·s, in particular greater than or equal to 2N·s, especially ranging from 2 N·s to 10 N·s and in particular ranging from 2 N·s to 5 N·s.

The tack of the wax is determined by measuring the change in force (compression force or stretching force) as a function of time, at 20° C., using the texturometer sold under the name TA-TX2i® by the company Rheo, equipped with a conical acrylic polymer spindle forming an angle of 45°.

The measuring protocol is as follows:

The wax is melted at a temperature equal to the melting point of the wax +10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the tack.

The texturometer spindle is displaced at a speed of 0.5 mm/s then penetrates the wax to a penetration depth of 2 mm. When the spindle has penetrated the wax to a depth of 2 mm, the spindle is held still for 1 second (corresponding to the relaxation time) and is then withdrawn at a speed of 0.5 mm/s.

During the relaxation time, the force (compression force) decreases greatly until it becomes zero, and then, during the withdrawal of the spindle, the force (stretching force) becomes negative and then rises again to the value 0. The tack corresponds to the integral of the curve of the force as a function of time for the part of the curve corresponding to negative values of the force (stretching force). The tack value is expressed in N·s.

The tacky wax that may be used generally has a hardness of less than or equal to 3.5 MPa, in particular ranging from 0.01 MPa to 3.5 MPa, especially ranging from 0.05 MPa to 3 MPa or even ranging from 0.1 MPa to 2.5 MPa.

The hardness is measured according to the protocol described previously.

A tacky wax that may be used is a $C_{20}$-$C_{40}$ alkyl(hydroxystearyloxy)stearate (the alkyl group containing from 20 to 40 carbon atoms), alone or as a mixture, in particular a $C_{20}$-$C_{40}$ alkyl 12-(12'-hydroxystearyloxy)-stearate, of formula (II):

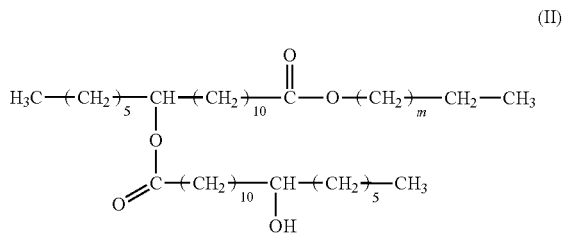

in which m is an integer ranging from 18 to 38, or a mixture of compounds of formula (II).

Such a wax is especially sold under the names Kester Wax K 82 P® and Kester Wax K 80 P® by the company Koster Keunen.

The waxes mentioned above generally have a starting melting point of less than 45° C.

The microcrystalline wax sold under the reference SP18 by the company Strahl & Pitsch, which has a hardness of about 0.46 MPa and a tack value of about 1N·s, may also be used.

The wax(es) may be in the form of an aqueous microdispersion of wax. The expression "aqueous microdispersion of wax" means an aqueous dispersion of wax particles in which the size of the wax particles is less than or equal to about 1 μm.

Wax microdispersions are stable dispersions of colloidal wax particles, and are described especially in "Microemulsions Theory and Practice", L. M. Prince Ed., Academic Press (1977) pages 21-32.

In particular, these wax microdispersions may be obtained by melting the wax in the presence of a surfactant, and optionally of a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained.

The wax microdispersions may also be obtained by stirring the mixture of wax, surfactant and water using stirring means such as ultrasound, high-pressure homogenizers or turbomixers.

The particles of the wax microdispersion preferably have mean sizes of less than 1 μm (especially ranging from 0.02 μm to 0.99 μm) and preferably less than 0.5 μm (especially ranging from 0.06 μm to 0.5 μm).

These particles consist essentially of a wax or a mixture of waxes. However, they may comprise a small proportion of oily and/or pasty fatty additives, a surfactant and/or a common liposoluble additive/active agent.

Lipophilic Film-Forming Polymer

The composition according to the invention may comprise at least one lipophilic film-forming polymer, which may be liposoluble (i.e. soluble in a liquid fatty phase comprising oils or organic solvents such as those described previously) or may be present in the composition in the form of particles dispersed in a non-aqueous solvent phase with which it is compatible, which may be the oily phase of the composition according to the invention.

Examples of liposoluble polymers that may be mentioned are copolymers of vinyl ester (the vinyl group being directly linked to the oxygen atom of the ester group and the vinyl ester containing a saturated, linear or branched hydrocarbon-based radical of 1 to 19 carbon atoms, linked to the carbonyl of the ester group) and of at least one other monomer, which may be a vinyl ester (other than the vinyl ester already present), an α-olefin (containing from 8 to 28 carbon atoms), an alkyl vinyl ether (in which the alkyl group comprises from 2 to 18 carbon atoms) or an allylic or methallylic ester (containing a saturated, linear or branched hydrocarbon-based radical of 1 to 19 carbon atoms, linked to the carbonyl of the ester group).

These copolymers may be crosslinked with the aid of crosslinking agents, which may be either of the vinyl type or of the allylic or methallylic type, such as tetraallyloxyethane, divinylbenzene, divinyl octanedioate, divinyl dodecanedioate and divinyl octadecanedioate.

Examples of these copolymers that may be mentioned are the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl-propionate/vinyl stearate, allyl dimethylpropionate/vinyl stearate, vinyl propionate/vinyl stearate, crosslinked with 0.2% divinylbenzene, vinyl dimethyl-propionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of liposoluble film-forming polymers that may also be mentioned are liposoluble copolymers, and in particular those resulting from the copolymerization of vinyl esters containing from 9 to 22 carbon atoms or of alkyl acrylates or methacrylates, and alkyl radicals containing from 10 to 20 carbon atoms.

Such liposoluble copolymers may be chosen from polyvinyl stearate, polyvinyl stearate crosslinked with the aid of divinylbenzene, of diallyl ether or of diallyl phthalate, polystearyl(meth)acrylate, polyvinyl laurate and polylauryl(meth)acrylate, it being possible for these poly(meth)acrylates to be crosslinked with the aid of ethylene glycol dimethacrylate or tetraethylene glycol dimethacrylate.

The liposoluble copolymers defined above are known and are described in particular in patent application FR-A-2 232 303; they may have a weight-average molecular weight ranging from 2000 to 500 000 and preferably from 4000 to 200 000.

As liposoluble film-forming polymers that may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Mention may also be made of silicone resins, which are generally soluble or swellable in silicone oils, which are crosslinked polyorganosiloxane polymers. The nomenclature of silicone resins is known under the name "MDTQ", the resin being described as a function of the various siloxane monomer units it comprises, each of the letters "MDTQ" characterizing a type of unit.

Examples of commercially available polymethyl-silsesquioxane resins that may be mentioned include those sold by the company Wacker under the reference Resin MK, such as Belsil PMS MK, or by the company Shin-Etsu under the reference KR-220L.

Siloxysilicate resins that may be mentioned include trimethyl siloxysilicate (TMS) resins such as those sold under the reference SR 1000 by the company General Electric or under the reference TMS 803 by the company Wacker. Mention may also be made of the trimethyl siloxysilicate resins sold in a solvent such as cyclomethicone, sold under the name KF-7312J by the company Shin-Etsu, and DC 749 and DC 593 by the company Dow Corning.

Mention may also be made of copolymers of silicone resins such as those mentioned above with polydimethylsiloxanes, for instance the pressure-sensitive adhesive copolymers sold by the company Dow Corning under the reference Bio-PSA and described in document U.S. Pat. No. 5,162,410, or the silicone copolymers derived from the reaction of a silicone resin, such as those described above, and a diorganosiloxane as described in document WO 2004/073 626.

The lipophilic or liposoluble film-forming polymer may also be present in the composition in the form of particles dispersed in a non-aqueous solvent phase, which may be that of the composition according to the invention. The techniques for preparing these dispersions are well known to those skilled in the art.

As examples of non-aqueous dispersions of film-forming polymer, mention may be made of the dispersions described, for example, in document EP 749 746 and especially acrylic polymer particles, surface-stabilized with a stabilizer, as a dispersion in a fatty phase (for example isododecane), for instance Mexomer PAP® from the company Chimex, dispersions of particles of a grafted ethylenic polymer, preferably an acrylic polymer, in a liquid fatty phase, the ethylenic polymer advantageously being dispersed in the absence of additional stabilizer at the surface of the particles, as described especially in document WO 04/055 081.

Additives
Dyestuff

The compositions in accordance with the invention may also comprise at least one dyestuff, for instance pulverulent dyestuffs, liposoluble dyes and water-soluble dyes.

The pulverulent dyestuffs may be chosen from pigments and nacres.

The pigments may be white or coloured, mineral and/or organic, and coated or uncoated. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments that may be mentioned are carbon black, pigments of D & C type, and lakes based on cochineal carmine or on barium, strontium, calcium or aluminium.

The nacres may be chosen from those listed above.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

These dyestuffs may be present in a content ranging from 0.01% to 30% by weight relative to the total weight of the composition.

According to one particular embodiment, the iron oxides will be present in a content ranging from 0.01% to 15% by weight and preferably from 0.01% to 10% by weight relative to the total weight of the composition.

Fibres

The compositions in accordance with the invention may also comprise fibres that allow an improvement in the lengthening effect.

The term "fibre" should be understood as meaning an object of length L and diameter D such that L is very much greater than D, D being the diameter of the circle in which the cross section of the fibre is inscribed. In particular, the ratio L/D (or shape factor) is chosen in the range from 3.5 to 2500, especially from 5 to 500 and in particular from 5 to 150.

The fibres that may be used in the composition of the invention may be mineral or organic fibres of synthetic or natural origin. They may be short or long, individual or organized, for example braided, and hollow or solid. They may have any shape, and may especially have a circular or polygonal (square, hexagonal or octagonal) cross section, depending on the intended specific application. In particular, their ends are blunt and/or polished to prevent injury.

In particular, the fibres have a length ranging from 1 μm to 10 mm, preferably from 0.1 mm to 5 mm and better still from 0.3 mm to 3.5 mm. Their cross section may be within a circle of diameter ranging from 2 nm to 500 μm, preferably ranging from 100 nm to 100 μm and better still from 1 μm to 50 μm. The weight or yarn count of the fibres is often given in denier or decitex, and represents the weight in grams per 9 km of yarn. In particular, the fibres according to the invention may have a yarn count chosen in the range from 0.15 to 30 denier and better still from 0.18 to 18 denier.

The fibres that may be used in the composition of the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the composition according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in the composition according to the invention in a content ranging from 0.01% to 10% by weight, in particular from 0.1% to 5% by weight and more particularly from 0.3% to 3% by weight relative to the total weight of the composition.

Cosmetic Active Agents

As cosmetic active agents that may be used in the compositions in accordance with the invention, mention may be made especially of antioxidants, preserving agents, fragrances, neutralizers, emollients, moisturizers, vitamins and screening agents, in particular sunscreens.

Needless to say, a person skilled in the art will take care to select the optional additional additives and/or the amount thereof such that the advantageous properties of the composition according to the invention are not, or are not substantially, adversely affected by the envisaged addition.

Assembly

The assembly according to the present invention comprises at least one applicator for the composition in accordance with the invention.

The composition is applied using the applicator, also known as the application means, described more particularly hereinbelow. In the embodiments that will be described hereinbelow, it is the applicator that is coupled to a vibrating member to make the composition vibrate, simultaneously with its application to the eyelashes, or after it has been applied.

The assembly according to the invention is preferably in the form of a single packaging. It may thus be in the form of a container delimiting at least one compartment or reservoir that comprises the composition according to the invention, the compartment optionally being closed by means of a closing member, and at least one vibrating application means for the composition.

The closing member may be coupled to the container by screwing. Alternatively, the coupling between the closing member and the container takes place other than by screwing, especially via a bayonet mechanism, by click-fastening or by tightening. The term "click-fastening" in particular means any system involving the passing of a rim or bead of material by elastic deformation of a portion, especially of the closing member, followed by return to the elastically unstressed position of the portion after the rim or bead has been passed.

The container may be at least partly made of thermoplastic material. Examples of thermoplastic materials that may be mentioned include polypropylene and polyethylene.

Alternatively, the container is made of a non-thermoplastic material, especially of glass or metal (or alloy).

The container is preferably equipped with a drainer located in the region of the aperture of the container. Such a drainer makes it possible to wipe the applicator and, optionally, the stem to which it may be solidly attached. Such a drainer is described, for example, in patent FR 2 792 618. The drainer may comprise, for example, a block of an alveolar material such as an open-cell or closed-cell foam, with or without flocking. As a variant, the drainer may comprise an optionally flocked, non-alveolar material, for example an elastomer or a polyolefin. In this case especially, the drainer may comprise, for example, at least one slit and/or may comprise a lip arranged to wipe the stem.

According to one particularly preferred embodiment, the makeup assembly comprises a reservoir comprising the composition according to the invention, the reservoir being equipped with the application means (or applicator) for the composition described hereinbelow.

According to one alternative, the reservoir has a capacity of less than or equal to 20 ml.

According to another alternative, the reservoir has a capacity strictly greater than 20 ml.

Application Means

The application means, or applicator, may be used to apply the composition to an area to be made up.

The applicator may also be used for finishing the makeup, on an area that has been made up or loaded with product by means of another applicator.

Advantageously, it is also used for making the composition vibrate at the time of its application or thereafter.

The composition according to the invention may be taken up in a container by immersing the application member therein. During the uptake, the application member may be subjected to the vibrations of the vibrating source, which may make it possible to obtain, where appropriate, more uniform loading of product onto the application member.

When the container comprises a wiping member through which the application is withdrawn, the application member may also be subjected to vibrations at the moment of passage through the wiping member, which may make it possible to obtain more uniform loading of product onto the application member.

When the container comprises a wiping member through which the application member is withdrawn, the application member may also be subjected to vibrations at the moment of passage through the wiping member, which may make it possible to obtain draining of the application member different from that which exists in the absence of vibration of the application member. The user may thus, for example, choose between at least two degrees of draining of the application member, depending on whether or not the application member vibrates at the moment of passing through the wiping member.

It may also prove to be more advantageous to make the applicator vibrate rather than the wiping member, since the vibrations of the applicator may be useful for the application also.

The wiping member may have an aperture that is markedly wider than the stem on which the application member may be borne.

The process for making up or caring for the eyelashes according to the invention may include the adjustment by the user of a vibration frequency and/or the adjustment of a vibration amplitude, for example by adjusting a control member.

The vibration amplitude of the application member during application is, for example, less than or equal to 5 mm, better still less than or equal to 3 mm, microvibrations of the application member being preferable to vibrations of larger amplitude.

The amplitude of the vibrations is optionally larger during uptake of the composition in a container or during passage through a wiping member.

According to one particular embodiment of the invention, the maximum amplitude of the vibrations (as typically imposed by the amplitude of the movement of the flyweight associated with the motor) is between 0.4 and 5 mm, preferably between 0.5 and 3 mm and, for example, around 0.5 mm, including 0.6, 0.7, 0.8, 0.9, 1, 1.1, 1.2, 1.3, 1.4, 1.5, 1.6, 1.7, 1.8, 1.9, 2, etc. mm.

The vibrations may be obtained in different ways, mechanically, hydraulically, pneumatically, electronically or electromechanically.

The vibrating source may comprise, for example, a motor driving a flyweight, an eccentric, an electromagnet or a piezoelectric or mechanical vibrator.

The contact between the vibrating source and the application part may be intermittent or extended, depending, for example, on the amplitude, the frequency and the orientation of the vibrations.

The vibrating source may generate vibrations, in particular sinusoidal vibrations, for example with a frequency of between 1 and 500 Hz, better still between 10 and 300 Hz and even better still between 50 and 200 Hz, including 30, 40, 60, 80, 100, 120, 140, 160, and 180 Hz.

The vibration frequency is, for example, greater than or equal to 20 Hz.

The vibrating source may comprise an electrical source, for example a 1.5 V battery. The motor may, for example, be arranged such that, when it is connected to a 1.5 V battery, it runs at a speed of between 5000 and 12 000 rpm.

According to one particular embodiment, the motor runs at a speed of between 5000 and 9000 rpm.

The vibrating system may be configured in such a way as to generate vibrations which are either principally perpendicular to the axis of the stem at the end of which the applicator is mounted (in accordance with what is described in patent application US2006/0032512 mentioned above), or principally longitudinal to the axis of the stem. The direction of the vibrations is taken to mean the direction of the vibrations when the application member (the brush) is charged with composition (mascara) and when it is brought into engagement with the eyelashes, i.e. when it is under the application condition.

According to one preferred embodiment of the invention, the vibrations are oriented principally longitudinally to the axis of the stem at the end of which the application means are attached. This orientation is found to be beneficial to the quality of the makeup obtained, in particular with regard to the smoothing out and separation of the eyelashes. Such a direction of vibration can be obtained by configuring the vibrating system in the manner represented in FIG. 35 of patent application FR2919476. In this configuration, the axis of rotation of the motor, in the form of a flat disc at the periphery of which one or more flyweights are distributed equidistantly, is substantially perpendicular to the axis of the stem at the end of which the application means are attached. With this configuration, the vibratory movement of the applicator is substantially in one plane (the plane of the flat disc). Within this plane, when the brush, charged with mascara, is brought into engagement with the fringe of eyelashes, the predominant component of the vibratory movement of the brush is along the axis of the stem.

According to one particular embodiment, the vibrating unit is mounted so as to be removable relative to the rest of the application unit. This makes it possible to use a vibrating unit in combination with different application parts in order, for example, to treat differently depending on the selected application parts.

The application part may optionally comprise a member for closing a container containing the composition according to the invention.

The process for applying the composition according to the invention to the eyelashes may also include the following:

i) forming a deposit of the cosmetic composition on the eyelashes, ii) simultaneously with the formation of the deposit or after deposition, subjecting this deposit to a vibrational motion, iii) leaving the deposit on the eyelashes, for it to be able to dry.

The application member is arranged to apply a product to the eyelashes, and may comprise, for example, a brush or a comb.

The brush may comprise a twisted core and bristles held between the turns of the core, or may be made in some other way.

The comb is, for example, made in a single block by moulding a plastic material.

The application member may be magnetic.

In certain embodiments, the application member is mounted at the end of a stem, which may be flexible, thus possibly contributing towards increasing the amplitude of the vibrations of the application member and/or improving the comfort during application.

The applicator may or may not comprise a reservoir containing the composition.

When the applicator does not comprise a reservoir containing the composition, the composition is, for example, contained in a container and the application member is, for example, loaded with composition by being at least partially introduced into this container. The container may or may not comprise a wiping member.

The vibrating source may be present on the applicator or, as a variant, forming part of a vibrating unit that may be removably mounted on an application part of the applicator.

The assembly may thus comprise a vibrating unit and several application parts associated with different application members or products.

The assembly comprises, for example, a vibrating unit and at least two application parts chosen from application parts intended for making up or caring for the eyelashes.

The reservoir may or may not be removably mounted on the applicator. When the reservoir is mounted on the applicator, to feed it with product, the wall of the reservoir serves, for example, for holding the applicator.

The assembly according to the invention may also comprise at least two different application members that may be selectively mounted on the applicator, this applicator comprising a vibrating source.

The assembly comprises, for example, several different application parts and a removable vibrating unit or several application members arranged to be mounted on a part of the applicator containing the vibrating source.

Application and vibration assemblies that may be used for implementing the invention are described especially in patent application WO 2006/090 343. Others are also described in patent applications WO 2006/020 577, WO 2006/130 644, WO 2006/130 643 and WO 2006/130 642, or US 2007/0 272 269. The content of these patent applications is incorporated into the present application by way of reference.

Figure 1:
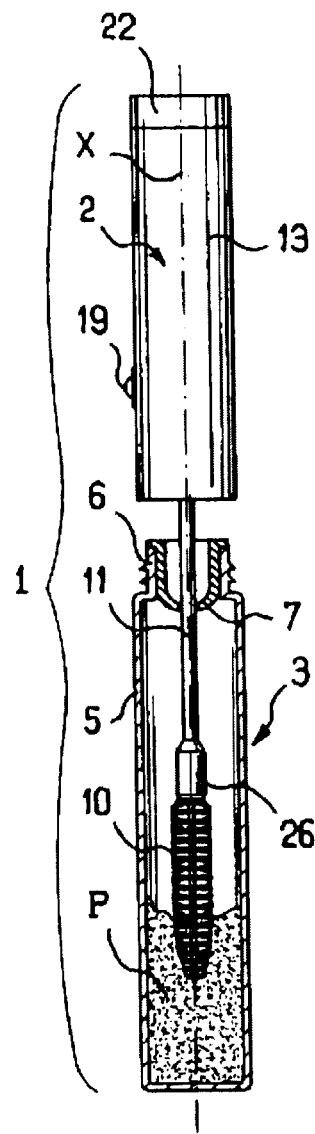
FIG. 1 schematically shows, with partial longitudinal cross section, a conditioning and application device in accordance with one embodiment of the invention.

The assembly may be understood more clearly on reading the detailed description that follows, of non-limiting examples of use thereof, and on inspection of the attached drawings, in which:

FIG. 1 schematically shows, with partial longitudinal cross section, a conditioning and application device in accordance with one embodiment of the invention, FIG. 2 shows in isolation the applicator of FIG. 1, with partial and schematic longitudinal cross section.

FIGS. 1 and 2 to which reference is made illustrate a conditioning and application device 1 in accordance with one embodiment described in patent application WO 2006/090 343. According to this embodiment, the conditioning and application assembly comprises an applicator 2 and a container 3 containing a reserve of a makeup product P, in the present case a composition according to the invention, for example mascara.

The container 3 comprises a body 5 provided with an externally threaded neck 6. A wiping member 7 is mounted in the neck 6.

The applicator 2 comprises an application member 10 formed, in the example under consideration, by a mascara brush. The application member 10 is mounted at the end of a stem 11, the other end of which is attached to a case 13 comprising an end part 14 arranged so as to screw onto the neck 6 and thus sealably close the container 3.

The case 13 houses a vibrating source for making the application member 10 vibrate during the application of the makeup product and/or during the uptake of product in the container and/or the extraction of the application member.

In the example under consideration, the vibrating source comprises a vibrator 16 composed of a motor 17 and a flyweight 18 driven in rotation by the motor, and the centre of gravity of which is eccentric relative to the axis of rotation. The motor 17 is powered electrically by a power source 20, for instance a battery stick, housed in the case 13 in the example under consideration and electrically connected to the motor via a switch 19.

The case 13 comprises a removable lid 22 for inserting and replacing the battery 20 and for providing an electrical contact therewith.

In the example under consideration, the axis of rotation of the motor 17 substantially coincides with the longitudinal axis X of the applicator, such that the vibrations are produced substantially perpendicularly to the axis X.

These vibrations are propagated along the stem 11 and cause the application member 10 to vibrate substantially perpendicularly to the axis X during the application of the product to the eyelashes.

In this figure, the brush has been represented very schematically to illustrate clearly the fact that the invention is not limited to a particular application member.

The brush 10 comprises, for example, bristles whose ends are arranged in helical layers. Oscillation of the brush 10 makes it possible to obtain a relative movement of the bristles of the brush 10 along the eyelashes C and thus to smooth out the product on the surface of the eyelashes and/or to orient fibres that may be contained in the product P. The vibrations of the brush 10 may also facilitate the separation of the eyelashes.

The motor 17 may be switched on during the application of the product to the eyelashes, whether it is during the initial application of the product or thereafter, to finish the makeup application.

The user can also make the brush vibrate when it is dipped into the container 3 so as, for example, to facilitate the loading of the brush with product, for example to obtain more uniform loading.

The user can also make the brush 10 vibrate when it passes the wiping member 7.

The stem may be made with a constant or variable cross section.

Preferably, the stem 11 is flexible, which may increase the amplitude of the vibrations of the brush 10, a person skilled in the art being able to select the dimensions of the stem as a function, for example, of the nature of the application member, of the product and of the treatment to be performed.

When the application member is configured in the form of a comb, this comb may be in accordance with what is described especially in applications US 2003-0 089 379-A1, U.S. Pat. No. 6,655,390, U.S. Pat. No. 6,814,084, U.S. Pat. No. 6,675,814, U.S. Pat. No. 6,581,610, U.S. Pat. No. 6,546,937, U.S. Pat. No. 6,539,950, U.S. Pat. No. 6,412,496 or U.S. Pat. No. 6,343,607, this list not being limiting.

The invention is not limited to a particular application member, and this member may especially be equipped with a means for heating the product and/or the eyelashes during application.

Besides the fact of making the composition vibrate, the vibrating applicator may also allow the composition to be heated, especially so as to modify its rheology during application. In this case, the switch may, for example, take several positions, one of them corresponding, for example, to heating only, and the others to vibrating only or to heating and vibrating simultaneously.

Various modifications may be made to the implementation examples that have just been described, without departing from the context of the present invention.

For example, the vibrating source may comprise a vibrator other than an electrical motor driving a flyweight in rotation and other than a piezoelectric vibrator. The vibrating source may especially comprise any pneumatic, hydraulic, mechanical, electronic or electromechanical system capable of producing vibrations.

The vibrating source may comprise vibration control means other than a simple on/off switch and may especially comprise mechanical or electronic control means, for adjusting the amplitude and/or frequency of the vibrations. The control means may, for example, comprise a potentiometer or a rotary or linear selector switch, for selecting at least two rotation speeds of the electrical motor when the vibrator comprises such a motor.

The vibrating source may comprise more than one vibrator, for example two vibrators arranged so as to produce oscillations in different directions. In this case, the vibrating source may also comprise, for example, a selector for selecting the vibrator(s) that it is desired to switch on.

The vibrating source may be, where appropriate, oriented by the user so as to make the application member vibrate with vibrations of desired orientation.

The vibrating source may comprise a power source that may be other than a battery, and may especially comprise one or more accumulators or condensers. Where appropriate, the vibrating source may be arranged so as to be able to be recharged with electricity by standing on a base.

Where appropriate, the vibrating source may be powered by the electrical mains via an optional transformer.

The vibrating source may be mounted in various ways in a corresponding housing of the applicator, and the mounting of the vibrating source is, for example, designed so as to promote the transfer of vibrations to the application member.

The vibrating source may be brought into service in ways other than those that have just been described.

A switch in the form of a pen grip may be used, as may any other contactor located on the side or at the end, depending on the type of application.

The application members may be of any type, especially with capillary slits or the like.

The application members may be made in various ways, especially by moulding, injection-moulding, staple fastening or twisting.

The application members may be intended for single use, where appropriate.

The application members may be mounted by any means onto the application part, especially by bonding, welding, punching, click-fastening, screwing, with magnets, by friction, by attachment of Velcro® type, or by gripping between jaws or the arms of pincers.

The power voltage of the vibrator, when it is electrical, is, for example, between 1 V and 9 V.

The application member may be driven in rotation, where appropriate, for example as described in U.S. Pat. No. 4,937,326, U.S. Pat. No. 4,922,934 and U.S. Pat. No. 6,565,276, the contents of which are incorporated herein by way of reference.

Making a mascara brush vibrate when it rotates may reduce the risk of the eyelashes becoming stuck in the bristles.

The application of the product may take place, especially when the invention is performed to apply a product to the eyelashes, after having heated the product, for example by placing it in a microwave oven.

The present invention is illustrated by the examples that follow. Unless otherwise mentioned, the amounts indicated are expressed as mass percentages relative to the total weight of the composition.

In all the examples that follow, the protocol for measuring the viscosity of the compositions is as follows:

Preparation of the Samples:

The vibrating brush according to the invention is immersed in the mascara and is then, once withdrawn from the mascara, subjected to:
  no vibration
  vibration for 3 minutes (brush held by the gripping means without being engaged with the eyelashes)
  vibration for 10 minutes (brush held by the gripping means without being engaged with the eyelashes).

A vibration having an amplitude of approximately 0.5 mm is used, the vibration being obtained by means of a motor having a rotational speed of 7000 rpm+/−2000, in the form of a flat disc, the axis of rotation of which is substantially perpendicular to the axis of the stem. The related frequency is about 117 Hz+/−33.

Mascara is then taken up on the brush using a spatula and placed on the lower plate of a rheometer (standing time between the end of vibration and the start of measurement ~2 minutes).

Rheology Measurement Protocol:
Rheometer RS600
20 mm plate/plate spindle—0.2 mm gap
Measurements taken at 25° C.
Speed of raising of the lower plate to be positioned at a gap of 0.2 mm: 1.25 mm/minute.

After positioning the sample on the spindle, standing time of 30 seconds.
60-second increase ramp from 0 to 1000 $s^{-1}$.
60-second decrease ramp from 1000 to 0 $s^{-1}$.

For each formulation, the measurement is repeated three times (on a new sample each time).

Results:

On each curve, the viscosity values are taken in poises at 100 $s^{-1}$, 400 $s^{-1}$ and 900 $s^{-1}$ on the shear increase. For the same sample, the mean viscosity value is calculated at these different shears.

The percentage variation in viscosity at the three different shears is calculated for each formulation that has undergone the vibrations relative to the same formula at rest.

A viscosity variation is said to be significant (significance threshold defined relative to the uncertainty associated with the reproducibility of the tests, such that the threshold is greater than any variation that might be attributed to the reproducibility) if it is greater than or equal to 10% in absolute value according to the protocol described above, for at least one of the measurements taken at 100 $s^{-1}$, 400 $s^{-1}$ and 900 $s^{-1}$ on the shear increase, after 3 and/or 10 minutes of vibration. The compositions having a variation in viscosity of greater than or equal to 10% in absolute value, preferably greater than or equal to 15% in absolute value and better still greater than or equal to 20% in absolute value, will be preferred according to the invention for use with a vibrating applicator.

According to a first embodiment, the preferred compositions may exhibit a decrease in viscosity of at least 10% (i.e. a negative variation of at least 10% compared with the control without vibration) when they are used with a vibrating applicator.

According to another embodiment, the preferred compositions may exhibit an increase in viscosity of at least 10% (i.e. a positive variation of at least 10% compared with the control without vibration) when they are used with a vibrating applicator.

This protocol therefore makes it possible to select or detect any mascara composition sensitive to shear and, consequently, any one indicated for use with a vibrating applicator according to the invention.

The present invention therefore also relates to an assembly for making up and/or caring for keratin materials, especially the eyelashes or the eyebrows, comprising:
- a container delimiting at least one compartment containing at least one composition for making up and/or caring for the keratin materials;
- at least one applicator comprising an application member for applying the composition to the keratin materials; and
- a vibrating source for, before, simultaneously with or after its application to the keratin materials, making the makeup composition vibrate, characterized in that the composition is as defined above and exhibits a variation in viscosity of at least 10% in absolute value, when it is subjected to a vibrating source with an amplitude of 0.5 mm, the vibration being obtained by a motor having a rotational speed of 7000 rpm+/−2000, in the form of a flat disc, the axis of rotation of which is substantially perpendicular to the axis of the stem (frequency 117 Hz+/−33), relative to the same composition at rest (without vibration), the variation in viscosity of the composition being measured using an RS600 rheometer according to the following protocol:

a) the vibrating applicator is immersed in the composition and is then, once withdrawn therefrom, subjected to no vibration (control), vibration for 3 minutes or vibration for 10 minutes;

b) the composition is taken up using a spatula and placed on the lower plate of an RS600 rheometer (20 mm plate/plate spindle—0.2 mm gap; speed of raising of the lower plate to be positioned at a gap of 0.2 mm: 1.25 mm/min;

c) shear curves are plotted using a 60-second increase ramp from 0 to 1000 s$^{-1}$/60-second decrease ramp from 1000 to 0 s$^{-1}$ d) the viscosity values are measured in poises at 100 s$^{-1}$, 400 s$^{-1}$ and 900 s$^{-1}$ on the shear increase;

e) the percentage variation in viscosity at the 3 different shears is calculated for each formulation that has undergone the vibrations relative to the same formulation at rest.

The present invention also relates to a process for selecting or detecting a composition that can be used with a vibrating applicator according to the invention, comprising the following:

a) the vibrating applicator (vibrating source with an amplitude of 0.5 mm, the vibration being obtained by means of a motor having a rotational speed of 7000 rpm+/−2000, in the form of a flat disc, the axis of rotation of which is substantially perpendicular to the axis of the stem, ie frequency 117 Hz+/−33) is immersed in the composition, and is then, once withdrawn therefrom, subjected to no vibration (control), vibration for 3 minutes or vibration for 10 minutes;

b) the composition is taken up using a spatula and placed on the lower plate of an RS600 rheometer (20 mm plate/plate spindle—0.2 mm gap; speed of raising of the lower plate to be positioned at a gap of 0.2 mm: 1.25 mm/min;

c) shear curves are plotted using a 60-second increase ramp from 0 to 1000 s$^{-1}$/60-second decrease ramp from 1000 to 0 s$^{-1}$;

d) the viscosity values are measured in poises at 100 s$^{-1}$, 400 s$^{-1}$ and 900 s$^{-1}$ on the shear increase;

e) the percentage variation in viscosity at the 3 different shears is calculated for each formulation that has undergone the vibrations relative to the same formulation at rest;

f) the compositions for which a variation in viscosity of at least 10% in absolute value, relative to the control, is obtained are selected.

EXAMPLE 1

Mascara According to the Invention Containing an Oily Continuous Phase with Platelet-Shaped Lipophilic Clay The following composition is prepared:

| | |
|---|---|
| Carnauba wax | 4.7 |
| | 8.3 |
| Paraffin | 2.8 |
| Hydrogenated jojoba oil | 0.1 |
| Rice bran wax | 2.8 |
| Microdispersion of carnauba wax with 10% ethanol (Mexoryl SAP from Chimex) | 7 |
| Black iron oxides | 4.2 |
| Preserving agents | qs |
| Hydrogenated C36 diacid/ethylenediamine condensate, esterified with stearyl alcohol (Uniclear 100 VG) | 1 |
| Polyvinyl laurate (Mexomer PP from Chimex) | 2.2 |
| Vinyl acetate/allyl stearate copolymer (65/35) (Mexomer PQ from Chimex) | 3.3 |
| Vinylpyrrolidone/eicosene copolymer (Antaron V220 from ISP) | 2 |
| Ethanol | 2 |
| Propylene carbonate | 1.9 |
| Isododecane | qs 100 |
| Distearyldimethylammonium-modified hectorite (Bentone 38 VCG) | 5.8 |
| Talc | 1 |

EXAMPLE 2

Measurement of the Impact of Vibration on the Mascara of Example 1

Protocol: see above
Results: the following results are obtained.

| | Viscosity (during increase) | | |
|---|---|---|---|
| | Viscosity @ 100 s$^{-1}$ Poise | Viscosity @ 400 s$^{-1}$ Poise | Viscosity @ 900 s$^{-1}$ Poise |
| Control | 107.67 | 24.17 | 10.30 |
| 3 min vibration | 113.00 | 26.00 | 10.90 |
| % vs control | 4.95 | 7.59 | 5.83 |
| 10 min vibration | 129 | 36.67 | 13.97 |
| % vs control | 19.81 | 51.72 | 35.60 |

The mascara according to Example 1 is thus particularly sensitive to vibration (minimum differences of 20% after 10 minutes of vibration): its viscosity is significantly increased when the vibration time increases.

EXAMPLE 3

Measurement of the Impact of Vibration on the Mascara Neutrogena Weightless Volume Wax Free The mascara Neutrogena Weightless Volume Wax Free is sold by Johnson & Johnson and comprises as ingredients, according to the full ingredient labelling:
WATER
MICA
POLYISOBUTENE CYCLOPENTASILOXANE
DIMETHICONE COPOLYOL POLYACRYLATE
GLYCERIN
POLYSORBATE 20
POLYURETHANE-1
HYDROXYETHYLCELLULOSE
DIMETHICONE
PROPYLENE GLYCOL
DIPROPYLENE GLYCOL
PANTOTHENIC ACID
ASCORBIC ACID
RETINYL PALMITATE
HYDROLYZED WHEAT PROTEIN
TOCOPHERYL ACETATE
SIMETHICONE
MATRICARIA (CHAMOMILLA RECUTITA) EXTRACT
GERANIUM MACULATUM EXTRACT
POLYSILICONE-11
PVP/HEXADECENE COPOLYMER
POLYMETHYL METHACRYLATE
ETHANOL
CITRIC ACID
PHENOXYETHANOL
ISOPROPYLPARABEN
ISOBUTYLPARABEN
BUTYLPARABEN
METHYLPARABEN
May contain: IRON OXIDES This mascara thus especially comprises mica as platelet-shaped filler, and also polysorbate-20 as nonionic surfactant.

Protocol: the viscosity measurement protocol is identical to that described above.

Results: the following results are obtained:

|  | Viscosity (during increase) | | |
| --- | --- | --- | --- |
|  | Viscosity @ 100 s$^{-1}$ Poise | Viscosity @ 400 s$^{-1}$ Poise | Viscosity @ 900 s$^{-1}$ Poise |
| Control | 130.00 | 34.67 | 19.47 |
| 3 min vibration | 133.33 | 43.80 | 22.50 |
| % vs control | 2.56 | 26.35 | 15.58 |
| 10 min vibration | 131.67 | 44.03 | 23.33 |
| % vs control | 1.28 | 27.02 | 19.86 |

The mascara Neutrogena Weightless Volume Wax Free is thus particularly sensitive to vibration (minimum differences of 15% after 3 or 10 minutes of vibration at 400 and 900 s$^{-1}$): its viscosity is significantly increased when the vibration time increases.

EXAMPLE 4

Mascara According to the Invention Containing an Aqueous Continuous Phase with an Oily Structuring Agent (Polyamide Silicone Polymer)

The following composition is prepared:

| EDTA | 0.2 |
| --- | --- |
| C18-C38 alkyl hydroxystearoyl stearate (Kester Wax K82P from Koster Keunen) | 5 |
| Isononyl isononanoate | 10.46 |
| Black iron oxides | 7.14 |
| Sodium dehydroacetate | 0.2 |
| Preserving agents | qs |
| Talc | 3 |
| Non-stabilized monopotassium monocetyl phosphate (Amphisol K) | 3.21 |
| Sorbitan tristearate (Span 65V from Croda) | 0.96 |
| PEG-40 stearate (Myrj 52 P from Croda) | 2.25 |
|  | 0.19 |
| Nylon-611/dimethicone copolymer (and) PPG-3 myristyl ether (Dow Corning 2-8178 Gellant from Dow Corning) | 19.26 |
| Acrylic and styrene/acrylic copolymers as an aqueous 40% emulsion in a water/butylene glycol/protected sodium lauryl ether sulfate mixture (Syntran 5760 from Interpolymer) | 5 |
| Hydroxyethylcellulose | 0.88 |
| Gum arabic | 3.38 |
| 1,3-Butylene glycol | 2.5 |
| Water | qs 100 |

EXAMPLE 5

Measurement of the Impact of Vibration on the Mascara of Example 4

Protocol: the viscosity measurement protocol is identical to that described above.

Results: the following results are obtained:

|  | Viscosity (during increase) | | |
| --- | --- | --- | --- |
|  | Viscosity @ 100 s$^{-1}$ Poise | Viscosity @ 400 s$^{-1}$ Poise | Viscosity @ 900 s$^{-1}$ Poise |
| Control | 139.33 | 34.13 | 20.67 |
| 3 min vibration | 141.00 | 34.67 | 21.27 |
| % vs control | 1.20 | 1.56 | 2.90 |
| 10 min vibration | 166.67 | 38.30 | 24.27 |
| % vs control | 19.62 | 12.21 | 17.42 |

The mascara according to Example 4 is thus sensitive to vibration (minimum differences of 12% after 10 minutes of vibration): its viscosity is significantly increased when the vibration time increases.

EXAMPLE 6

Mascara According to the Invention Containing an Aqueous Continuous Phase with an Oily Structuring Agent (Semi-Crystalline Polymer)

A mascara having the following proportions is prepared:

| Fatty phase | 35% |
| --- | --- |
| Stearic acid | 5.82% |
| Neutralizers | 2.9% |
| Black iron oxide | 8% |
| Hydroxyethylcellulose | 0.91% |
| Gum arabic | 3.45% |
| Additives, preserving agents, water | qs | in which the fatty phase is formed by the following mixture:

Fatty phase=mixture of polybutene (1)/stearyl acrylate N-vinylpyrrolidone (2) copolymer (40/60) with a melting point of 56° C.

(1): Indopol H 100 from the company Amoco (2): Basic polymer with a melting point of 56° C. prepared according to the following procedure:

120 g of cyclohexane are placed in a 1 liter reactor equipped with a central paddle stirrer, a condenser and a thermometer, and are heated from room temperature to 80° C. over 45 minutes. At 80° C., the mixture $C_1$ below is introduced over 2 hours:

40 g of cyclohexane+4 g of Trigonox 141 [2,5-bis(2-ethylhexanoylperoxy)-2,5-dimethylhexane].

30 minutes after the start of addition of mixture $C_1$, mixture $C_2$ is introduced over 1 hour 30 minutes, this mixture being formed from:

190 g of stearyl acrylate+10 g of N-vinylpyrrolidone+400 g of cyclohexane.

At the end of the two additions, the mixture is left to act for a further 3 hours at 80° C., and all the cyclohexane present in the reaction medium is then distilled off at atmospheric pressure.

The polymer containing 100% by weight of active material is then obtained.

Its weight-average molecular mass $M_w$ is 38 000 expressed as polystyrene equivalent and its melting point m.p. is 56° C., measured by DSC.

EXAMPLE 7

Measurement of the Impact of Vibration on the Mascara of Example 6

Protocol: the viscosity measurement protocol is identical to that described above.

Results: the following results are obtained:

|  | Viscosity (during increase) | | |
|---|---|---|---|
|  | Viscosity @ 100 s$^{-1}$ Poise | Viscosity @ 400 s$^{-1}$ Poise | Viscosity @ 900 s$^{-1}$ Poise |
| Control | 97.67 | 35.87 | 17.20 |
| 3 min vibration | 102.00 | 36.10 | 17.67 |
| % vs control | 4.44 | 0.65 | 2.71 |
| 10 min vibration | 99.33 | 39.93 | 21.30 |
| % vs control | 1.71 | 11.34 | 23.84 |

The mascara according to Example 6 is thus sensitive to vibration (minimum difference of 20% after 10 minutes of vibration at 900 s$^{-1}$): its viscosity is significantly increased when the vibration time increases.

EXAMPLE 8

Measurement of the Impact of Vibration on the Mascara Magnascopic

The mascara Magnascopic is sold by Estée Lauder and comprises as ingredients, according to the full ingredient labelling:
WATER
ISODODECANE
ETHYLENEDIAMINE/STEARYL DIMER TALLATE COPOLYMER (UNICLEAR)
CYCLOMETHICONE
KAOLIN
STEARIC ACID
STEARAMIDE MEA STEARATE
AMMONIUM SHELLACATE
POLYSORBATE 20
SILICA
SORBITAN TRISTEARATE
GLYCERYL STEARATE
PEG-100 STEARATE
MAGNESIUM ALUMINUM SILICATE
HYDROXYETHYLCELLULOSE
PVP
TOCOPHERYL ACETATE
ACACIA SENEGAL GUM
PTFE
COFFEE (COFFEA ARABICA) SEED EXTRACT
PANTOTHENIC ACID POLYPEPTIDE
HYDROLYZED JOJOBA PROTEIN
SILK AMINO ACIDS
AMINOMETHYL PROPANEDIOL
PROPYLENE GLYCOL
TETRADIBUTYL PENTAERYTHRITYL HYDROXYHYDROCINNAMATE
ISOPROPYL ALCOHOL
DISODIUM EDTA
CHLORPHENESIN
SORBIC ACID
PHENOXYETHANOL
METHYLPARABEN
BUTYLPARABEN
ETHYLPARABEN
PROPYLPARABEN
ISOBUTYLPARABEN
May contain:
MICA
TITANIUM DIOXIDE
IRON OXIDES
BRONZE POWDER
BLUE 1
ALUMINUM POWDER
YELLOW 5
FERRIC FERROCYANIDE
YELLOW 5 LAKE
ULTRAMARINES
CARMINE
CHROMIUM HYDROXIDE GREEN
CHROMIUM OXIDE GREENS
BISMUTH OXYCHLORIDE
BLUE 1 LAKE This mascara thus especially comprises Uniclear (polyamide polymer) as fatty-phase rheological agent.

Protocol: see above.

Results: the following results are obtained:

|  | Viscosity | | |
|---|---|---|---|
|  | Viscosity @ 100 s$^{-1}$ (Poise) | Viscosity @ 400 s$^{-1}$ (Poise) | Viscosity @ 900 s$^{-1}$ (Poise) |
| Control | 96.00 | 24.93 | 10.66 |
| 3 min vibration | 69.75 | 22.11 | 9.58 |
| % vs control | −27.35 | −11.31 | −10.13 |
| 10 min vibration | 69.3 | 22.48 | 9.83 |
| % vs control | −27.82 | −9.83 | −7.79 |

The mascara Magnascopic is thus particularly sensitive to vibration (differences of greater than 10% after 3 minutes of vibration, and after 10 minutes of vibration at 100 s$^{-1}$): its viscosity is significantly reduced when the vibration time increases.

EXAMPLE 9

Measurement of the Impact of Vibration on a Mascara According to the Invention Containing Platelet-Shaped Fillers of Mica-Titanium Dioxide-Black Iron Oxide Type Composition of the Test Mascara

| | |
|---|---|
| Mica-titanium oxide-black iron oxide (58/18/24) (CI: 77019 + 77891 + 77499) Colorona Patina Silver ® from the company Merck | 22% |
| Acrylates/Steareth-20 methacrylate copolymer (Aculyn 22 Polymer ® from Rohm & Haas) | 35% |
| Microdispersion of carnauba wax (Mexoryl SAP ® from Chimex) | 20% |
| Preserving agents | qs |
| Water | qs 100% |

| | Viscosity | | |
|---|---|---|---|
| | Viscosity @ 100 s$^{-1}$ (Poise) | Viscosity @ 400 s$^{-1}$ (Poise) | Viscosity @ 900 s$^{-1}$ (Poise) |
| Control | 194.00 | 2.03 | 0.41 |
| 3 min vibration | 105.00 | 0.64 | 0.23 |
| % vs control | −45.88 | −68.64 | −43.90 |
| 10 min vibration | 117.33 | 0.79 | 0.28 |
| % vs control | −39.52 | −61.25 | −32.52 |

This composition is thus particularly sensitive to vibration (differences of greater than 30% after 3 and 10 minutes of vibration): its viscosity is significantly reduced.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. The term "mentioned" notes exemplary embodiments, and is not limiting to certain species.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. An assembly for making up and/or caring for keratin material, comprising:
   a container delimiting at least one compartment containing at least one composition for making up and/or caring for the keratin material;
   at least one applicator comprising an application member for applying the composition to the keratin material; and
   a vibrator capable of making the makeup composition vibrate before, simultaneously with or after its application to the keratin material,
   wherein the composition comprises platelet-shaped particles that are gelling agents or fillers.

2. The assembly according to claim 1, wherein the platelet-shaped particles are chosen from lipophilic and hydrophilic clays, talc, mica, barium sulfate, kaolin, lauroyllysine, starch, boron nitride, precipitated calcium carbonate, magnesium carbonate, magnesium hydrogen carbonate, hydroxyapatite, montmorillonite, polytetrafluoroethylene wax particles, calcium sulfate, pumice powder, bismuth oxychloride, bismuth oxychloride and zinc oxide powder, perlite, glass particles about 10 microns in size and about 0.4 micron thick or about 25 microns in size and about 0.4 micron thick, silica and titanium dioxide sol/gel particles, mica and titanium dioxide particles, metal soaps derived from organic carboxylic acids containing from 8 to 22 carbon atoms, and multilayer platelet-shaped reflective particles, and mixtures thereof.

3. The assembly for making up and/or caring for keratin material according to claim 1, wherein the composition further comprises at least one nonionic surfactant and/or at least one ionic surfactant and/or at least one polymeric surfactant.

4. The assembly according to claim 3, wherein the composition comprises at least one nonionic surfactant.

5. The assembly according to claim 3, wherein the composition comprises at least one nonionic surfactant and at least one anionic surfactant.

6. The assembly for making up and/or caring for keratin material according to claim 1, wherein the composition further comprises at least one oil structured with at least one fatty-phase rheological agent chosen from:
   crystalline polymers;
   mineral lipophilic structuring agents;
   polymers of lipophilic polyamide type;
   polymers of lipophilic polyurea or polyurethane type;
   silicone polymers comprising at least one hydrocarbon-based unit comprising groups capable of establishing hydrogen interactions, chosen from ester, amide, sulfonamide, carbamate, thiocarbamate, urea, urethane, thiourea, oxamido, guanidino and biguanidino groups and combinations thereof;
   organogelling agents;
   block polymers;
   cholesterol-based liquid-crystal agents;
   and mixtures thereof.

7. The assembly according to claim 6, wherein the composition comprises less than 10% by weight of wax.

8. The assembly according to claim 6, wherein the fatty-phase rheological agent is chosen from semi-crystalline polymers, polyamides and silicone polymers comprising at least one hydrocarbon-based unit comprising two amide groups.

9. The assembly for making up and/or caring for keratin material according to claim 1, wherein the composition further comprises at least one oil structured with at least one fatty-phase rheological agent and less than 10% by weight of wax.

10. The assembly according to claim 9, wherein the fatty-phase rheological agent is chosen from semi-crystalline polymers, polyamides and silicone polymers comprising at least one hydrocarbon-based unit comprising two amide groups.

11. The assembly according to claim 1, wherein the vibrator is coupled to the application member so as to allow this member to vibrate before application of the composition to the fibres, during application of the composition to the fibres, or thereafter.

12. The assembly according to claim 1, wherein the application member especially comprises a brush or a comb.

13. The assembly according to claim 1, wherein the application member is mounted at the end of a stem.

14. The assembly according to claim 1, wherein the vibrator generates vibrations with a frequency of greater than or equal to 20 Hz.

15. The assembly according to claim 1, wherein the vibrator generates vibrations that have an amplitude of less than or equal to 5 mm.

16. The assembly according to claim 1, wherein the container comprises a thermoplastic material.

17. The assembly according to claim 1, wherein the container comprises a non-thermoplastic material.

18. A process for making up and/or caring for keratin material, comprising:
applying to the keratin material at least one coat of a makeup and/or care composition,
making the composition vibrate before and/or simultaneously with and/or after its application to the keratin material,
wherein the composition:
comprises platelet-shaped particles that are gelling agents or fillers, and one or more of
(A) at least one nonionic surfactant, at least one ionic surfactant, at least one polymeric surfactant, or a combination thereof;
(B) at least one oil structured with at least one fatty-phase rheological agent chosen from:
crystalline polymers;
mineral lipophilic structuring agents;
polymers of lipophilic polyamide type;
polymers of lipophilic polyurea or polyurethane type;
silicone polymers comprising at least one hydrocarbon-based unit comprising groups capable of establishing hydrogen interactions, chosen from ester, amide, sulfonamide, carbamate, thiocarbamate, urea, urethane, thiourea, oxamido, guanidino and biguanidino groups and combinations thereof;
organogelling agents;
block polymers;
cholesterol-based liquid-crystal agents;
and mixtures thereof, or
(C) at least one oil structured with at least one fatty-phase rheological agent and less than 10% by weight of wax.

* * * * *